(12) United States Patent
Voegtli et al.

(10) Patent No.: US 12,083,169 B2
(45) Date of Patent: Sep. 10, 2024

(54) ALKALINE PHOSPHATASE POLYPEPTIDES AND METHODS OF USE THEREOF

(71) Applicant: Alexion Pharmaceuticals, Inc., Boston, MA (US)

(72) Inventors: Walter C. Voegtli, Boston, MA (US); Yuhong Wu, Boston, MA (US); Jonathan Monteleone, Boston, MA (US); Tatyana Mezhebovsky, Boston, MA (US); Eric Falcone, Boston, MA (US); Yang Guo, Boston, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 74 days.

(21) Appl. No.: 17/669,275

(22) Filed: Feb. 10, 2022

(65) Prior Publication Data
US 2022/0265784 A1   Aug. 25, 2022

Related U.S. Application Data

(60) Provisional application No. 63/149,090, filed on Feb. 12, 2021.

(51) Int. Cl.
| | |
|---|---|
| A61K 38/46 | (2006.01) |
| A61K 47/00 | (2006.01) |
| A61K 47/02 | (2006.01) |
| A61K 47/22 | (2006.01) |
| A61K 47/26 | (2006.01) |
| A61P 19/08 | (2006.01) |
| C07K 14/47 | (2006.01) |
| C12N 9/16 | (2006.01) |

(52) U.S. Cl.
CPC ............ *A61K 38/465* (2013.01); *A61K 47/02* (2013.01); *A61K 47/22* (2013.01); *A61K 47/26* (2013.01); *A61P 19/08* (2018.01); *C12N 9/16* (2013.01); *C12Y 301/03001* (2013.01); *C07K 2319/30* (2013.01)

(58) Field of Classification Search
CPC ........ A61K 38/46; A61K 47/00; C07K 14/47; C12N 9/16
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,112,341 B1 | 9/2006 | Nagarajan et al. |
| 7,179,903 B2 | 2/2007 | McArthur et al. |
| 7,256,253 B2 | 8/2007 | Bridon et al. |
| 7,271,149 B2 | 9/2007 | Glaesner et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Alonso et al., J. Bone Miner. Res., 2020, vol. 35(4):657-661.*
Rodriguez et al., Ann. Rheum. Dis., 2023; vol. 82:428-429.*
Ali et al., "Isolation and characterization of calcifying matrix vesicles from epiphyseal cartilage," Proc Natl Acad Sci USA. 67(3):1513-20 (1970).
Anderson et al., "Pyrophosphate stimulation of calcium uptake into cultured embryonic bones. Fine structure of matrix vesicles and their role in calcification," Dev Biol. 34:211-227 (1973).

(Continued)

*Primary Examiner* — Xiaozhen Xie

(74) *Attorney, Agent, or Firm* — Clark & Elbing LLP

(57) ABSTRACT

Featured are pharmaceutical compositions that include a soluble alkaline phosphatase for treating bone mineralization disorders, such as hypophosphatasia (HPP), and symptoms thereof. The polypeptides include a soluble alkaline phosphatase (sALP) or fragment thereof, which is derived from a naturally occurring alkaline phosphatase (ALP).

29 Claims, 16 Drawing Sheets

Specification includes a Sequence Listing.

(56) References Cited

U.S. PATENT DOCUMENTS

| | | | |
|---|---|---|---|
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,650,412 B2 | 5/2017 | Konstantinov et al. |
| 9,650,413 B2 | 5/2017 | Konstantinov et al. |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 10,603,361 B2 | 3/2020 | Odrijin |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0022728 A1 | 1/2009 | Lin |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0004096 A1 | 1/2014 | Nichols |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0015784 A1 | 1/2016 | Shaw et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |
| 2019/0099473 A1 | 4/2019 | Fujita et al. |
| 2020/0224182 A1 | 7/2020 | Rajendran et al. |
| 2021/0169994 A1 | 6/2021 | Voegtli et al. |
| 2021/0317425 A1 | 10/2021 | Godawat et al. |
| 2022/0154155 A1 | 5/2022 | Godawat et al. |

FOREIGN PATENT DOCUMENTS

| | | |
|---|---|---|
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |

(56) References Cited

FOREIGN PATENT DOCUMENTS

| | | |
|---|---|---|
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 1985697 A1 | 10/2008 |
| EP | 2158319 | 3/2010 |
| EP | 1759001 B1 | 4/2011 |
| EP | 2158319 B1 | 12/2011 |
| EP | 3250227 A2 | 12/2017 |
| JP | 8-70875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2014-181229 A | 9/2014 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079400 A2 | 7/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/133511 A2 | 11/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2013/169397 A1 | 11/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |
| WO | WO-2021/119218 A1 | 6/2021 |

OTHER PUBLICATIONS

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).

Anderson et al., "The role of matrix vesicles in growth plate development and biomineralization," Front Biosci. 10:822-37 (2005).

(56) References Cited

OTHER PUBLICATIONS

Beertsen et al., "Root development in mice lacking functional tissue non-specific alkaline phosphatase gene: Inhibition of acellular cementum formation," J Dent Res. 78(6):1221-1229 (1999) (10 pages).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-25 (1978).
Bonilla, "Pharmacokinetics of immunoglobulin administered via intravenous or subcutaneous routes," Immunol Allergy Clin N Am. 28:803-19 (2008).
Byers et al., "Effect of enzyme replacement therapy on bone formation in a feline model of mucopolysaccharidosis type VI," Bone. 21(5):425-31 (1997).
Cameron et al., "Minireview: Natriuretic peptides during development of the fetal heart and circulation," Endocrinology. 144(6):2191-4 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for European Patent Application No. 08757088.3, executed Jan. 14, 2011 (6 pages).
Engel et al., "Characterization of the hormone binding site of natriuretic peptide receptor-C," FEBS Lett. 360(2):169-72 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-26 (1999) (19 pages).
Garg, "Investigation of the role of FcRn in the absorption, distribution, and elimination of monoclonal antibodies," Dissertation: State University of New York at Buffalo, 2007 (Abstract only) (2 pages).
Greenberg et al., "A homoallelic Gly$^{317}$ to Asp mutation in ALPL causes the perinatal (lethal) form of hypophosphatasia in Canadian Mennonites," Genomics. 17:215-7 (1993).
Harmey et al., "Concerted regulation of inorganic pyrophosphate and osteopontin by Akp2, Enpp1, and Ank," Am J Pathol. 164(4):1199-209 (2004).
Harmey et al., "Elevated skeletal osteopontin levels contribute to the hypophosphatasia phenotype in Akp2$^{-/-}$ mice," J Bone Miner Res. 21(9):1377-86 (2006).
Hawrylak et al., "The solubilization of tetrameric alkaline phosphatase from human liver and its conversion into various forms by phosphatidylinositol phospholipase C or proteolysis," J Biol Chem. 263(28):14368-73 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-8 (1992).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9 (2002).
Jansonius, "Structure, evolution and action of vitamin B$_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & Peptide Drug Delivery—Third International Conference: Minimally invasive delivery methods, Sep. 22-23, Philadelphia, PA, USA," IDrugs. 6(11):1043-5 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millán, *Mammalian Alkaline Phosphatases: From Biology to Applications in Medicine and Biotechnology*, Wiley-VCH Verlag GmbH & Co., Weinheim, Germany (2006) (324 pages).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516, <http://www.ncbi.nlm.nih.gov/protein/AAF64516>, retrieved Apr. 16, 2013 (2 pages).
NCBI Protein Database Accession No. AAC33858, <http://www.ncbi.nlm.nih.gov/protein/AAC33858>, retrieved Apr. 16, 2013 (1 page).
NCBI Protein Database Accession No. AAH21289, <http://www.ncbi.nlm.nih.gov/protein/AAH21289>, retrieved Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321(Pt 2)(Pt 2):297-303 (1997).
Ramachandran et al., "Treatment of an anabolic bone deficiency in neurofibromatosis with bone morphogenetic proteins and its poten-

(56) References Cited

OTHER PUBLICATIONS tial application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharm Res. 14(7): 911-6 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33(2):405-412 (1983).
Wang et al., "A mouse model for achondroplasia produced by targeting fibroblast growth factor receptor 3," Proc Natl Acad Sci USA. 96(8):4455-4460 (1999).
Wang et al., "Structure-based chemical modification strategy for enzyme replacement treatment of phenylketonuria," Mol Genet Metab. 86(1-2):134-140 (2005).
Weiss et al., "A missense mutation in the human liver/bone/kidney alkaline phosphatase gene causing a lethal form of hypophosphatasia," Proc Natl Acad Sci USA. 85(20):7666-7669 (1988).
Whyte et al., "Enzyme-replacement therapy in life-threatening hypophosphatasia," N Engl J Med. 366(10):904-13 (2012).
Whyte et al., "Markedly increased circulating pyridoxal-5'-phosphate levels in hypophosphatasia," J Clin Invest. 76(2):752-756 (1985).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Zierhut et al., "Population PK-PD model for Fc-osteoprotegerin in healthy postmenopausal women," J Pharmacokinet Pharmacodyn. 35(4):379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, mailed Nov. 15, 2012 (9 pages).
International Search Report and Written Opinion for International Patent Application No. PCT/US2012/039004, mailed Nov. 2, 2012 (22 pages).
Invitation to Pay Additional Fees for International Patent Application No. PCT/US2012/039004, mailed Aug. 29, 2012 (2 pages).
Oikawa et al., "Enzyme replacement therapy on hypophosphatasia mouse model," J Inherit Metab Dis. 37(2):309-17 (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell. 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int. 60(3):309-15 (1997).
Ciancaglini et al., "Contribution of matrix vesicles and alkaline phosphatase to ectopic bone formation," Braz J Med Biol Res. 39(5):603-10 (2006).
Crawley et al., "Enzyme replacement therapy in a feline model of Maroteaux-Lamy syndrome," J Clin Invest. 97(8):1864-73 (1996).

Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al. "Protein tolerance to random amino acid change," Proc Natl Acad Sci USA. 101(25):9205-10 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Millán et al., "Enzyme replacement therapy for murine hypophosphatasia," J Bone Miner Res. 23(6):777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Infantile hypophosphatasia: enzyme replacement therapy by intravenous infusion of alkaline phosphatase-rich plasma from patients with Paget bone disease," J Pediatr. 101(3):379-86 (1982).

(56) References Cited

OTHER PUBLICATIONS

Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte, "Hypophosphatasia," in The Metabolic and Molecular Bases of Inherited Disease (8th ed.), pp. 5313-5329, 2001 (McGraw-Hill Book Company) (epub pp. 1-41).
Whyte, Chapter 18: Heritable Forms of Rickets and Osteomalacia. *Connective Tissue and Its Heritable Disorders*. Wiley-Liss, Inc., eds. R.M. Royce and B. Steinmann, 765-87 (2002).
Whyte et al., "Marrow cell transplantation for infantile hypophosphatasia," J Bone Miner Res. 18(4):624-36 (2003).
Yamamoto et al., "Prolonged survival and phenotypic correction of Akp2$^{-/-}$ hypophosphatasia mice by lentiviral gene therapy," J Bone Miner Res. 26(1):135-42 (2011).
Communication from Examining Division for European Application No. 05739065.0, dated Jun. 18, 2009 (6 pages).
Communication from Examining Division for European Application No. 05739065.0, dated Jun. 11, 2010 (5 pages).
Office Action for U.S. Appl. No. 12/793,517, mailed Aug. 16, 2010 (9 pages).
Office Action for U.S. Appl. No. 13/071,445, mailed Feb. 6, 2012 (12 pages).
Supplementary European Search Report for European Application No. 05739065, mailed Dec. 2, 2008 (3 pages).
Choe et al., "Substrate profiling of cysteine proteases using a combinatorial peptide library identifies functionally unique specificities," J Biol Chem. 281(18):12824-32 (2006).
Official Action and Translation for Japanese Application No. 2013-544989, mailed Oct. 27, 2015 (6 pages).
Harris, "The human alkaline phosphatases: what we know and what we don't know," Clin Chim Acta. 186(2):133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, mailed Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).
Advisory Action for U.S. Appl. No. 11/484,870, mailed Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," Am J Pathol. 164(3):841-7 (2004).
Barranger et al., "Lessons learned from the development of enzyme therapy for Gaucher disease," J Inherit Metab Dis. 24(Suppl. 2):89-96 (2001).
Bobé et al., "Fas-mediated liver damage in MRL hemopoietic chimeras undergoing lpr-mediated graft-versus-host disease," J Immunol. 159(9):4197-4204 (1997).
Boskey, "Amorphous calcium phosphate: The contention of bone," J Dent Res. 76(8):1433-1436 (1997).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).

Cleland et al., "Emerging protein delivery methods," Curr Opin Biotechnol. 12:212-9 (2001).
Communication from Examining Division for European Application No. 08757088.3, dated Apr. 20, 2011 (4 pages).
Data Sheet for pFUSE-SEAP-hFc "Plasmid designed for the expression of a SEAP-Fc Fusion protein," Invivogen, San Diego, CA (1 page) (1989).
Extended European Search Report for European Application No. 11774253.6, dated Oct. 14, 2013 (8 pages).
Extended European Search Report for European Application No. 11000196.3, mailed Jun. 22, 2011 (6 pages).
Extended European Search Report for European Application No. 11004496.3, mailed Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-38 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-17 (1992).
Hult et al., "Engineered enzymes for improved organic synthesis," Curr Opin Biotechnol. 14:395- 400 (2003).
Hunter et al., "Modulation of crystal formation by bone phosphoproteins: structural specificity of the osteopontin-mediated inhibition of hydroxyapatite formation," Biochem J. 300:723-8 (1994).
Ikezawa, "Glycosylphosphatidylinositol (GPI)-anchored proteins," Biol Pharm Bull. 25(4):409-17 (2002).
International Search Report and Written Opinion for International Patent Application No. PCT/CA2005/000615, mailed Aug. 18, 2005 (14 pages).
International Search Report and Written Opinion for International Patent Application No. PCT/CA2008/000923, mailed Sep. 12, 2008 (11 pages).
International Search Report and Written Opinion for International Patent Application No. PCT/CA2011/050258, mailed Jul. 29, 2011 (14 pages).
Kasugai et al., "Selective drug delivery system to bone: small peptide (Asp)$_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231(1):1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization, " J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).

(56) References Cited

OTHER PUBLICATIONS

NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).
Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, mailed Dec. 4, 2008 (7 pages).
Office Action for U.S. Appl. No. 11/111,664, mailed May 14, 2008 (8 pages).
Office Action for U.S. Appl. No. 11/111,664, mailed Oct. 4, 2007 (11 pages).
Office Action for U.S. Appl. No. 11/484,870, mailed Aug. 11, 2009 (15 pages).
Office Action for U.S. Appl. No. 11/484,870, mailed Feb. 2, 2009 (16 pages).
Office Action for U.S. Appl. No. 11/484,870, mailed Jan. 25, 2007 (15 pages).
Office Action for U.S. Appl. No. 11/484,870, mailed Jul. 5, 2007 (13 pages).
Office Action for U.S. Appl. No. 11/484,870, mailed Jun. 25, 2008 (16 pages).
Office Action for U.S. Appl. No. 11/484,870, mailed Oct. 1, 2007 (12 pages).
Office Action for U.S. Appl. No. 12/405,920, mailed Aug. 9, 2010 (7 pages).
Office Action for U.S. Appl. No. 12/405,920, mailed Dec. 17, 2009 (14 pages).
Office Action for U.S. Appl. No. 13/071,445, mailed May 25, 2012 (14 pages).
Official Notification and Search Report for Eurasian Patent Application No. 201291138, dated Jul. 16, 2013 (3 pages).
Patti et al., "Critical residues in the ligand-binding site of the *Staphylococcus aureus* collagen-binding adhesin (MSCRAMM)," J Biol Chem. 270(20):12005-11 (1995).
Reply to Final Office Action for U.S. Appl. No. 13/071,445, dated Oct. 25, 2012 (14 pages).
Reply to Final Office Action for U.S. Appl. No. 11/111,664, dated Sep. 10, 2008 (32 pages).
Restriction Requirement for U.S. Appl. No. 12/599,679, mailed Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961- 969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).

Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Supplementary European Search Report for European Application No. 08757088, dated Jun. 7, 2010 (5 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Chapter 70: Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Science. 290(5491):471-3 (2000).
Skolnick et al., "From genes to protein structure and function: novel applications of computational approaches in the genomic era," Trends Biotechnol. 18(1):34-9 (2000).
The Japanese Journal of Dermatology. 115(6): 843-7 (2005) (11 pages).
Bocciardi et al., "Overexpression of the C-type natriuretic peptide (CNP) is associated with overgrowth and bone anomalies in an individual with balanced t(2;7) translocation," Hum Mutat. 28(7):724-31 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-25 (1999).
Chusho et al., "Dwarfism and early death in mice lacking C-type natriuretic peptide," Proc Natl Acad Sci USA. 98(7):4016-21 (2001).
Daggubati et al., "Adrenomedullin, endothelin, neuropeptide Y, atrial, brain, and C-natriuretic prohormone peptides compared as early heart failure indicators," Cardiovasc Res. 36:246-55 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(6):847-57 (1998).
Furuya et al., "Structural requirements of C-type natriuretic peptide for elevation of cyclic GMP in cultured vascular smooth muscle cells," Biochem Biophys Res Commun. 183(3):964-9 (1992).
Hagiwara et al., "Autocrine regulation of rat chondrocyte proliferation by natriuretic peptide C and its receptor, natriuretic peptide receptor-B," J Biol Chem. 269(14):10729-33 (1994).
Hagiwara et al., "cGMP produced in response to ANP and CNP regulates proliferation and differentiation of osteoblastic cells," Am J Physiol Cell Physiol. 270:C1311-18 (1996) (9 pages).
Horton et al., "Achondroplasia," Lancet. 370:162-72 (2007).
Inoue et al., "Four functionally distinct C-type natriuretic peptides found in fish reveal evolutionary history of the natriuretic peptide system," Proc Natl Acad Sci USA. 100(17):10079-84 (2003).
International Search Report and Written Opinion for International Patent Application No. PCT/CA2011/050807, mailed Apr. 13, 2012 (18 pages).

(56) References Cited

OTHER PUBLICATIONS

International Search Report for International Patent Application No. PCT/US2012/060869, mailed Mar. 25, 2013 (5 pages).
Invitation to Pay Additional Fees for International Patent Application No. PCT/CA2011/050807, mailed Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Millán, Chapter 7: The in vivo role of TNAP. Mammalian alkaline phosphatases: From Biology to Applications in Medicine and Biotechnology. Wiley-VCH Verlag GmbH & Co., 107-185 (2006).
Miyazawa et al., "Cyclic GMP-dependent protein kinase II plays a critical role in C-type natriuretic peptide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31(1):101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274(5295):2082-2086 (1996).
Potter et al., "Natriuretic peptides, their receptors, and cyclic guanosine monophosphate- dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223(1):1-6 (1996).
Takano et al., "Molecular evolution of shark C-type natriuretic peptides," Zoolog Sci. 11(3):451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319(2):171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Whyte, Chapter 207: Hypophosphatasia. *The Online Metabolic and Molecular Bases for Inherited Disease*. McGraw-Hill Book Company, Valle et al. (eds.) (2001) (41 pages).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).

Husain et al., "Fc site-specific labeling of immunoglobulins with calf intestinal alkaline phosphatase," Bioconjug Chem. 5(5):482-90 (1994).
Mayer, "Chapter 4: Immunoglobulins: Structure and Function," *Microbiology and Immunology On-line*, University of South Carolina School of Medicine, <http://pathmicro.med.sc.edu/mayer/IgStruct2000.htm> (2009) (12 pages).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, mailed Mar. 25, 2014 (3 pages).
International Preliminary Report on Patentability for International Patent Application No. PCT/US2012/060869, issued Apr. 22, 2014 (7 pages).
International Preliminary Report on Patentability for International Patent Application No. PCT/US2012/039004, issued Apr. 22, 2014 (8 pages).
Siris et al., "Paget's disease of bone," Trends Endocrinol Metab. 2(6):207-12 (1991).
Extended European Search Report for European Patent Application No. 12842640.0, mailed Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal pancraniosynostosis in a patient with infantile hypophosphatasia," Cleft Palate Craniofac J. 53(6):741-4, doi: 10.1597/15-027 (2016).
International Search Report and Written Opinion for International Patent Application No. PCT/US2015/058498, mailed Jan. 22, 2016 (12 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Product Monograph, Including Patient Medication Information. Strensiq™ (asfotase alfa), Solution for Injection 40 mg/mL & 100 mg/mL," <http://alexionpharma.ca/documents/Strensiq-PM-asfotase-alfa-14Aug2015.aspx>, prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
Center for Drug Evaluation and Research, "Application No. 125513Orig1s000," <http://www.accessdata.fda.gov/drugsatfda_docs/nda/2015/125513Orig1s000MedR.pdf>, review completed Oct. 20, 2015; retrieved on Jun. 1, 2016 (254 pages).
International Search Report and Written Opinion for International Patent Application No. PCT/US2016/025721, mailed Aug. 17, 2016 (18 pages).
Invitation to Pay Additional Fees for International Patent Application No. PCT/US2016/015366, mailed Jun. 1, 2016 (7 pages).
Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).
Highlights of Prescribing Information for Strensiq™ (asfotase alfa) Injection, Alexion Pharmaceuticals, Inc., <http://www.alexion.com/Documents/strensiq_pi-10-2015.aspx> (2015) (19 pages).
Phillips et al., "Gait assessment in children with childhood hypophosphatasia: impairments in muscle strength and physical

(56) References Cited

OTHER PUBLICATIONS function," The Endocrine Society's 97th Annual Meeting & Expo, Mar. 5-8, San Diego, California. Poster LBS-039 (2015) (2 pages).
"View of NCT02235493 on 2015_11_19," ClinicalTrials.gov archive, updated Nov. 19, 2015, retrieved Jan. 27, 2017 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
International Search Report and Written Opinion for International Patent Application No. PCT/US2016/039595, mailed Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, dated Oct. 9, 2015 (101 pages).
Reply Brief as Filed in U.S. Appl. No. 12/638,527, dated Apr. 22, 2016 (4 pages).
Examiner's Answer to Appeal Brief for U.S. Appl. No. 12/638,527, mailed Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, mailed Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts," J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).

Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Wickramasinghe et al., "A case of hypophosphatasia," Ceylon Med J. 48(3):94-5 (2003) (2 pages).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, mailed Aug. 10, 2017 (10 pages).
International Search Report and Written Opinion for International Patent Application No. PCT/US2017/047527, mailed Nov. 6, 2017 (10 pages).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2016).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl-/- mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26):1003-7 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).

(56) References Cited

OTHER PUBLICATIONS

Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 Å resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq@, 2018 (8 pages).
European Collection of Authenticated Cell Cultures (ECACC), General Cell Collection: NS0, Catalogue No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57 (2015).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5 (2018).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Chapter 15: Recombinant enzyme replacement therapy in hypophosphatasia," *Neuronal Tissue-Nonespecific Alkaline Phosphatase (TNAP): Subcellular Biochemistry*. Caroline Fonta and Laszlo Negyessy, 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Chapter 2: Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017) (1 page).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).

(56) References Cited

OTHER PUBLICATIONS

Takahashi et al., "Parental serum alkaline phosphatase activity as an auxiliary tool for prenatal diagnosis of hypophosphatasia," Prenat Diagn. 37(5):491-6 (2017).

Tenorio et al., "Molecular and clinical analysis of ALPL in a cohort of patients with suspicion of hypophosphatasia," Am J Med Genet A. 173(3):601-10 (2017).

Tsiantouli et al., "Hypophosphatasia," Rev Med Suisse. 13(559):855-8 (2017) (Article in French) (English Abstract Included).

Weber et al., "Burden of disease in adult patients with hypophosphatasia: Results from two patient-reported surveys," Metabolism. 65(10):1522-30 (2016).

Whyte, "Hypophosphatasia—aetiology, nosology, pathogenesis, diagnosis and treatment," Nat Rev Endocrinol. 12(4):233-46 (2016).

Whyte, "Hypophosphatasia: an overview for 2017," Bone. 102:15-25 (2017).

Whyte et al., "Hypophosphatasia: natural history study of 101 affected children investigated at one research center," Bone. 93:125-138 (2016).

Whyte et al., "Hypophosphatasia: validation and expansion of the clinical nosology for children from 25 years experience with 173 pediatric patients," Bone. 75:229-39 (2015).

International Search Report and Written Opinion for International Patent Application No. PCT/US2016/054013, mailed Dec. 13, 2016 (19 pages).

Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).

International Search Report and Written Opinion for International Patent Application No. PCT/US2018/020859, mailed Jun. 19, 2018 (14 pages).

López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).

Matsumoto et al., "Rescue of severe infantile hypophosphatasia mice by AAV-mediated sustained expression of soluble alkaline phosphatase," Hum Gene Ther. 22(11):1355-64 (2011).

Hofmann et al., "Clinical aspects of hypophosphatasia: an update," Clinic Rev Bone Miner Metab. 11(2):60-70 (2013).

Taketani et al., "Clinical and genetic aspects of hypophosphatasia in Japanese patients," Arch Dis Child. 99(3):211-5 (2014) (6 pages).

Whyte, "Physiological role of alkaline phosphatase explored in hypophosphatasia," Ann N Y Acad Sci. 1192:190-200 (2010).

Hofmann et al., "Compound heterozygosity of two functional null mutations in the ALPL gene associated with deleterious neurological outcome in an infant with hypophosphatasia," Bone. 55:150-7 (2013).

De Roo et al., "Infantile hypophosphatasia without bone deformities presenting with severe pyridoxine-resistant seizures," Mol Genet Metab. 111(3):404-7 (2014).

International Search Report and Written Opinion for International Patent Application No. PCT/US2015/064003, mailed Mar. 31, 2016 (13 pages).

Lazdunski et al., "Structure-function relationships for some metalloalkaline phosphatases of *E. coli*," Eur J Biochem. 8(4):510-7 (1969).

Bobyr et al., "High-resolution analysis of Zn(2+) coordination in the alkaline phosphatase superfamily by EXAFS and x-ray crystallography," J Mol Biol. 415(1):102-17 (2012).

International Search Report and Written Opinion for International Patent Application No. PCT/US2017/036133, mailed Aug. 24, 2017 (10 pages).

International Search Report and Written Opinion for International Patent Application No. PCT/US2018/025206, mailed Jul. 3, 2018 (25 pages).

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).

International Search Report and Written Opinion for International Patent Application No. PCT/US2017/025618, mailed Jul. 11, 2017 (22 pages).

Li et al., "Standard reference for the six-minute-walk test in healthy children aged 7 to 16 years," Am J Respir Crit Care Med. 176(2):174-80 (2007).

Park et al., "Ex vivo assessment of contractility, fatigability and alternans in isolated skeletal muscles," J Vis Exp. 69:e4198 (2012) (8 pages).

Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).

Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012) (1 page).

Sugano et al., "Successful gene therapy in utero for lethal murine hypophosphatasia," Hum Gene Ther. 23(4):399-406 (2012).

International Search Report and Written Opinion for International Patent Application No. PCT/US2015/039973, mailed Oct. 5, 2015 (12 pages).

Johnson et al., "Motor proficiency in children with neurofibromatosis type 1," Pediatr Phys Ther. 22(4):344-8 (2010).

Gates et al., "Effects of age, sex, and comorbidities on the pediatric outcomes data collection instrument (PODCI) in the general population," J Pediatr Orthop. 35(2):203-9 (2015).

International Search Report and Written Opinion for International Patent Application No. PCT/US2016/049983, mailed Nov. 29, 2016 (12 pages).

International Search Report and Written Opinion for International Patent Application No. PCT/US2016/015366, mailed Aug. 9, 2016 (14 pages).

Extended European Search Report for European Application No. 18173111.8, dated Aug. 21, 2018 (9 pages).

National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).

Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <http://abstracts.eurospe.org/hrp/0086/hrp0086FC2.5.htm> (2016) (4 pages).

International Search Report and Written Opinion for International Application No. PCT/US18/26868, mailed Sep. 7, 2018 (30 pages).

International Preliminary Report on Patentability for International Patent Application No. PCT/US2016/049983, issued Sep. 11, 2018 (9 pages).

"Sequence 4," SCORE Search Results for U.S. Appl. No. 12/599,679, retrieved Nov. 17, 2018 (2 pages).

Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).

Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).

Barcia et al., "Infantile hypophosphatasia: treatment options to control hypercalcemia, hypercalciuria, and chronic bone demineralization," J Pediatr. 130(5):825-8 (1997).

Barvencik et al., "Skeletal mineralization defects in adult hypophosphatasia—a clinical and histological analysis," Osteoporosis Int. 22(10):2667-75 (2011).

Baumgartner-Sigl et al., "Pyridoxine-responsive seizures as the first symptom of infantile hypophosphatasia caused by two novel mis-

(56) References Cited

OTHER PUBLICATIONS sense mutations (c.677T>C, p.M226T; c.1112C>T, p.T371l) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8):984-91 (2008).
Chan et al., "Endoscope-assisted versus open repair of craniosynostosis: a comparison of perioperative cost and risk," J Craniofac Surg. 24(1):170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3(Suppl 3):S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliova et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c. 1559delT in ALPL, a common mutation resulting in the perinatal (lethal) form of hypophosphatasia in Japanese and effects of the mutation on heterozygous carriers," J Hum Genet. 56(2):166-8 (2011).

(56) References Cited

OTHER PUBLICATIONS

Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KIGGS)," Gesundheitsberichterstattung des Bundes, Robert Koch Institute (2009) (136 pages).
Communication pursuant to Rule 164(2)(b) and Article 94(3) EPC for European Patent Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).

Extended European Search Report for European Application No. 15907550.6, dated Jun. 4, 2019 (7 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (6 pages).
Official Action for Russian Patent Application No. 2017123540, dated Jul. 8, 2019 (15 pages).
Di Rocco et al. "Craniosynostosis and hypophosphatasia," Arch Pediatr. 24(5S2):5S89-5S92 (2017).
Official Action and Translation for Japanese Application No. 2017-539393, mailed Sep. 17, 2019 (14 pages).
Whyte et al. "Natural history of perinatal and infantile hypophosphatasia: a retrospective study," J Pediatr. 209:116-124.e4 (2019) (13 pages).
Leung et al. "Outcome of perinatal hypophosphatasia in Manitoba Mennonites: a retrospective cohort analysis," JIMD Rep. 11:73-78 (2013).
Taketani et al. Chapter 9: Hypophosphatasia. *Human Pathobiochemistry*. T. Oohashi et al. (eds.), 91-100 (2019).
Morrison et al. "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Whyte et al. "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Mornet, "The tissue nonspecific alkaline phosphatase gene mutations database," <www.sesep.uvsq.fr/03_hypo_mutations.php>, last updated Nov. 28, 2019 (14 pages).
Hancarova et al. "Hypophosphatasia due to uniparental disomy," Bone. 81:765-766 (2015).
Carden et al. "Tracheomalacia and tracheobronchomalacia in children and adults: an in-depth review," Chest. 127(3):984-1005 (2005).
Murgu et al. "Tracheobronchomalacia and excessive dynamic airway collapse," Respirology. 11(4):388-406 (2006).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Park et al. "The effect of alendronate loaded biphasic calcium phosphate scaffolds on bone regeneration in a rat tibial defect model," Int J Mol Sci. 16(11):26738-53 (2015) (17 pages).
Li et al. "Timing of the initiation of bisphosphonates after surgery for fracture healing: a systematic review and meta-analysis of randomized controlled trials," Osteoporos Int. 26(2):431-41 (2015) (11 pages).
International Search Report and Written Opinion for International Application No. PCT/US2019/045963, mailed Jan. 30, 2020 (26 pages).
Rodionova et al., "Hypophosphatasia in adults: clinical cases and literature review," Osteoporosis and Bone Diseases. 18(2):25-7 (2015) (4 pages).
Search Report and Translation for Russian Application No. 2018109368, dated Feb. 5, 2020 (4 pages).
Wang et al. "The effects of tissue-non-specific alkaline phosphatase gene therapy on craniosynostosis and craniofacial morphology in the FGFR2$^{C342Y/+}$ mouse model of Crouzon craniosynostosis," Orthod Craniofac Res. 18 Suppl. 1(01):196-206 (2015).
Abrams et al., "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Notice of Reasons for Rejection for Japanese Application No. 2018-508754, mailed Jun. 30, 2020 (11 pages).
Phillips et al., "Gait Assessment in Children with Childhood Hypophosphatasia: Impairments in Muscle Strength and Physical

(56) References Cited

OTHER PUBLICATIONS

Function," The Endocrine Society's 97th Annual Meeting & Expo, Mar. 5-8, San Diego, CA (2015) (2 pages).
Communication pursuant to Article 94(3) EPC for European Patent Application No. 16739617.5, dated May 11, 2020 (10 pages).
Office Action for Russian Patent Application No. 2018137822, mailed Jul. 24, 2020 (20 pages).
Bishop et al., "Life-threatening hypophosphatasia (HPP): Results of up to two years bone-targeted Enzyme Replacement Therapy (ERT) in infants and young children," Bone. 48:S82 (2011) (1 page) (Abstract only).
Little et al., "Lineage tracking of myogenic progenitors in surgical models of tibial bone repair," Bone. 48(2):S82 (2011).
Kim et al., "Comparison of phenylketonuria (PKU) patients' height, weight and body mass index (BMI) to the general population," Mol Genet Metab. 105:328-329 (2012).
Whyte et al., "Treatment of children with hypophosphatasia (HPP) with ENB-0040: radiographic and DXA outcomes after 6 months of therapy," Horm Res Paediatr. 76(Suppl 2):26 (2011) (Abstract only).
Kim et al., "Comparison of phenylketonuria (PKU) patients' height, weight and body mass index (BMI) to the general population," Molecular Genetics and Metabolism. 105:328-329 (2012).
Notice of Reasons for Rejection for Japanese Patent Application No. 2018-515934, mailed Jul. 28, 2020 (7 pages).
Dbfetch, "Bone targeted alkaline phosphatase, kits and methods of use thereof," Database No. HI520929, last updated Nov. 2, 2010 (1 page).
Seefried et al., "Long-term Effectiveness of Asfotase Alfa Treatment in Adults with Pediatric-onset Hypophosphatasia in Routine Clinical Practice," 2020 American Society for Bone and Mineral Research Virtual Conference, Sep. 11-15, 2020 (1 page).
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020) (1 page).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020) (1 page).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020) (1 page).
Seefried et al., "Bone Turnover and Mineral Metabolism in Adult Patients with Pediatric-Onset Hypophosphatasia Treated With Asfotase Alfa," 2020 World Congress on Osteoporosis, Osteoarthritis, and Muscoloskeletal Diseases, Aug. 20-23, Barcelona, Spain (2020) (1 page).
"Scale-up of CHO fed-batch cultures in HyClone (TM) ActiPro (TM) medium supplemented with Cell Boost (TM) 7a and 7b," GE Healthcare Bio-Sciences AB, dated Sep. 2016 (4 pages).
Fu-Hang et al., "Preliminary study on the effect of $Zn^{2+}$ on the activities of peptidase and alkaline phosphatase," Marine Sciences. 27(3):64-65 (2003) (Abstract only).
Office Action for Chinese Patent Application No. 201680048588.5, issued Jan. 18, 2021 (28 pages).
Dutta et al., "Men and mice: Relating their ages," Life Sci. 152:244-8 (2016) (5 pages).
Zhang et al., "Engineering *E. coli* Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).
"Data file 29-0929-25 AA. Xcellerex™ XDR cell culture bioreactor systems," GE Healthcare Life Sciences, published Feb. 2014 (4 pages).

Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Protein Database Accession No. NM_000478.2, retrieved on Feb. 23, 2021 (7 pages).
Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).
Abbruzzese, "The Tinetti Performance-Oriented Mobility Assessment Tool," Am J Nursing. 98(12):16J-16L (1998) (3 pages).
International Search Report and Written Opinion for International Patent Application No. PCT/US20/64140, mailed Apr. 23, 2021 (70 pages).
Kishnani et al., "Five-year efficacy and safety of asfotase alfa therapy for adults and adolescents with hypophosphatasia," Bone. 121:149-162 (2019).
Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, <https://www.clinicaltrials.gov/ct2/show/NCT00739505>, last updated Mar. 29, 2019 (8 pages).
Alexion Pharmaceuticals, "Safety and Efficacy Study of Asfotase Alfa in Adolescents and Adults With Hypophosphatasia (HPP)," ClinicalTrials.gov. NCT01163149, <https://clinicaltrials.gov/ct2/show/NCT01163149>, last updated Mar. 13, 2019 (9 pages).
Alexion Pharmaceuticals, "Strensiq (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BWE>, dated Nov. 5, 2015 (1 page).
European Medicines Agency, "Strensiq: Asfotase Alfa," <www.ema.europa.eu/en/medicines/human/EPAR/strensiq>, last updated Mar. 25, 2021 (8 pages).
Hofmann et al., "Efficacy and safety of asfotase alfa in infants and young children with hypophosphatasia: a phase 2 open-label study," J Clin Endocrinol Metab. 104(7): 2735-2747 (2019) (14 pages).
Examination Report No. 1 for Australian Patent Application No. 2016308624, dated Aug. 27, 2021 (6 pages).
Kim et al., "CHO cells in biotechnology for production of recombinant proteins: current state and further potential," Appl Microbiol Biotechnol. 93(3):917-30 (2012).
Office Action for Chinese Patent Application No. 201780021666.7, issued Jul. 21, 2021 (34 pages).
McCormack et al., "Is bigger better? An argument for very low starting doses," CMAJ. 183(1):65-9 (2011).
Rush, "Childhood hypophosphatasia: to treat or not to treat," Orphanet J Rare Dis. 13(1):116 (2018) (5 pages).
Phillips et al., "Clinical Outcome Assessments: Use of Normative Data in a Pediatric Rare Disease," Value Health. 21(5):508-514 (2018).
Office Action for Japanese Patent Application No. 2018-551309, mailed Nov. 2, 2021 (11 pages).
Office Action for Russian Patent Application No. 2019134794, mailed on Dec. 7, 2021 (11 pages).
Examination Report for Canadian Patent Application No. 2,967,851, dated Dec. 21, 2021 (4 pages).
Communication pursuant to Article 94(3) EPC for European Patent Application No. 16852428.8, dated Dec. 8, 2021 (4 pages).
"Scale-up of CHO fed-batch cultures in HyClone™ ActiPro™ medium supplemented with Cell Boost™ 7a and 7b," GE Healthcare Bio-Sciences AB, dated Sep. 2016 (4 pages).
Decision on Rejection for Chinese Patent Application No. 201680048588.5, issued on Jan. 20, 2022 (19 pages).
Communication pursuant to Article 94(3) EPC for European Patent Application No. 16758322.8, dated Jan. 25, 2022 (3 pages).
Communication pursuant to Article 94(3) EPC for European Patent Application No. 18775045.0, dated Jan. 25, 2022 (6 pages).

(56) References Cited

OTHER PUBLICATIONS

Office Action for Japanese Patent Application No. 2019-548417 mailed on Jan. 18, 2022 (8 pages).
"Effects of feeding strategy on CHO cell performance in fed-batch cultures using HyClone ActiPro medium and Cell Boost 7a and 7b supplements," Cytiva, <http://www.processdevelopmentforum.com/posters/effects-of-feeding-strategy-on-cho-cell-performance-in-fed-batch-cultures/>. 2017 (5 pages).
Examination Report No. 2 for Australian Patent Application No. 2016308624 issued Apr. 7, 2022 (4 pages).
Examination Report for Canadian Patent Application No. 2,973,883 issued Mar. 24, 2022 (6 pages).
Office Action for Chinese Patent Application No. 201780021666.7 issued on Mar. 9, 2022 (23 pages).
Witkowski et al., "Conversion of a beta-ketoacyl synthase to a malonyl decarboxylase by replacement of the active-site cysteine with glutamine," Biochemistry. 38(36):11643-50 (1999).
Whisstock et al., "Prediction of protein function from protein sequence and structure," Q Rev Biophys. 36(3):307-40 (2003).
An et al., "IgG2m4, an engineered antibody isotype with reduced Fc function," mAbs. 1(6): 572-579 (2009).
Komaru et al., "Molecular and cellular basis of hypophosphatasia," J Oral Biosci. 61(3):141-148 (Sep. 2019).
Sharma et al., "Alkaline Phosphatase: An Overview," Indian J Clin Biochem. 29(3):269-278 (2014).
Office Action for U.S. Appl. No. 17/117,099, dated Nov. 28, 2022 (200 pages).
Luo et al., "Lower ultrafiltration temperature improves membrane performance and emulsifying properties of milk protein concentrates," Dairy Sci. & Technol. 95(1):15-31 (Sep. 2014).
Klidaras et al., "Fracture Healing in Two Adult Patients With Hypophosphatasia After Asfotase Alfa Therapy," JBMR Plus. 2(5):304-307 (May 2018).
Evans et al., "Vaccine therapy for cancer—fact or fiction?," QJM. 92(6):299-307 (1999).
Cuzick et al., "Overview of the main outcomes in breast-cancer prevention trials," Lancet. 361(9354):296-300 (2003).
Schiffman et al., "The promise of global cervical-cancer prevention," N Engl J Med. 353(20):2101-2104 (2005).
Komenaka et al., "Immunotherapy for melanoma," Clin Dermatol. 22(3):251-265 (2004).
Hernandez-Ledesma et al., "Lunasin, a novel seed peptide for cancer prevention," Peptides. 30(2):426-430 (2009).
Whyte et al., "Supplemental Data: Asfotase alfa therapy for children with hypophosphatasia," JCI Insight. 1(9):e85971 (Jun. 2016) (33 pages).
"Strensiq: Assessment Report," European Medicines Agency, dated Jun. 25, 2015 (92 pages).
"Pharmaceutical and Food Safety Bureau Examination and Management Division / Pharmaceuticals and Medical Devices Agency, Review Report," published Oct. 26, 2015 (English Abstract) (64 pages).
Notice of Final Rejection for Korean Patent Application No. 10-2018-7028255, dated Apr. 21, 2022 (7 pages).
Communication pursuant to Article 94(3) EPC for European Patent Application No. 15825878.0, dated Apr. 4, 2022 (5 pages).
Notice of Reasons for Rejection for Japanese Patent Application No. 2019-553247, mailed Apr. 20, 2022 (5 pages).
Office Action for Chinese Patent Application No. 201780021666.7, issued on Jun. 20, 2022 (22 pages).
Notice of Final Rejection for Korean Patent Application No. 10-2018-7028255, dated Aug. 18, 2022 (7 pages).
Office Action for Brazilian Patent Application No. BR112018070243-9, dated Sep. 7, 2022 (10 pages).
International Search Report and Written Opinion of the International Searching Authority for International Application No. PCT/US2020/064140, mailed Apr. 23, 2021 (12 pages).
GenBank NM_000478.2, "*Homo sapiens* alkaline phosphatase, liver/bone/kidney (ALPL), mRNA," <https://www.ncbi.nlm.nih.gov/nuccore/NM_000478.2>, dated Sep. 17, 2006, retrieved on Feb. 23, 2021 (7 pages).
International Search Report and Written Opinion for International Patent Application No. PCT/US2022/016031, mailed May 3, 2022 (9 pages).
Office Action for Japanese Patent Application No. 2021-506690, dated May 30, 2023 (10 pages).
Miller et al., "Genetic diversity and population structure of the endangered marsupial Sarcophilus harrisii (Tasmanian devil)," Proc Natl Acad Sci U S A. 108(30):12348-53 (Jul. 2011).
Partial Supplementary European Search Report for European Application No. 20898477.3, dated Dec. 6, 2023 (25 pages).
UniProtKB Accession No. G3WYY8. Retrieved Nov. 16, 2011 (4 pages).
Official Action for Japanese Application No. 2021-506690, dated Nov. 7, 2023 (10 pages).
International Search Report and Written Opinion for International Patent Application No. PCT/US2021/055991, mailed Jan. 25, 2022 (8 pages).
Official Action for Eurasian Application No. 202391228, dated Dec. 13, 2023 (5 pages).

\* cited by examiner

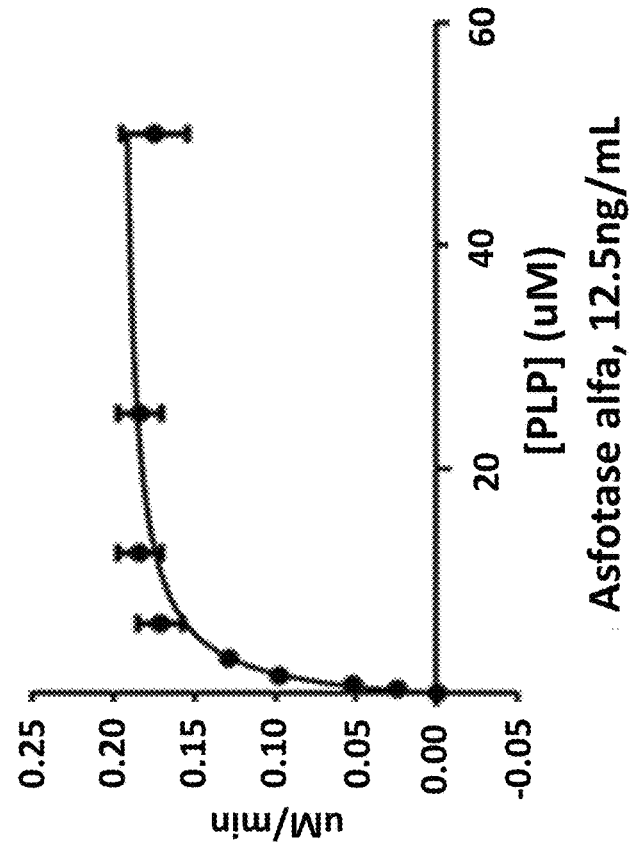
FIG. 2
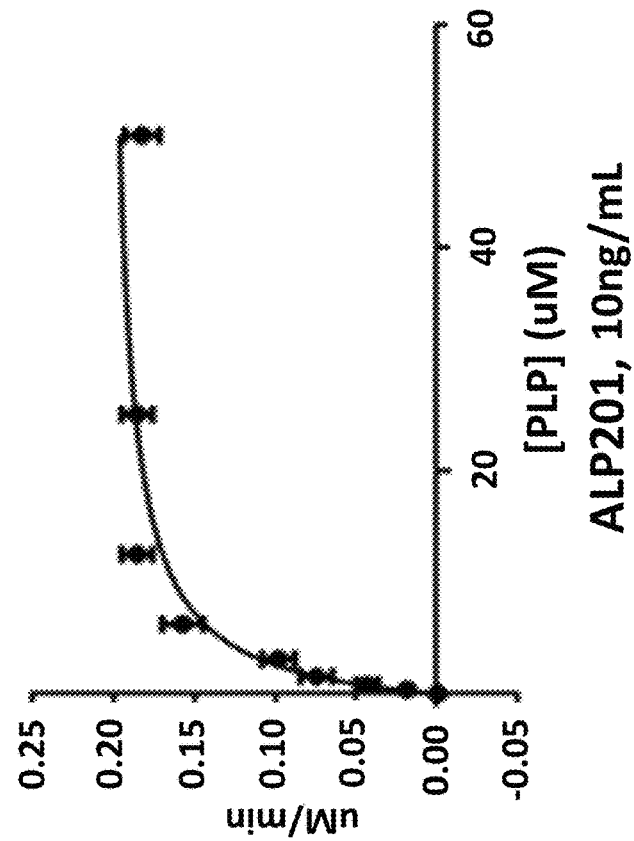

SEQUENCE LISTING

```
<160> NUMBER OF SEQ ID NOS: 6

<210> SEQ ID NO 1
<211> LENGTH: 507
<212> TYPE: PRT
<213> ORGANISM: Homo sapiens

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175
```

```
Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Ala Gly Ser Leu Ala Gly Pro Leu Leu Leu
                485                 490                 495

Ala Leu Ala Leu Tyr Pro Leu Ser Val Leu Phe
            500                 505

<210> SEQ ID NO 2
<211> LENGTH: 485
<212> TYPE: PRT
<213> ORGANISM: Artificial Sequence
<220> FEATURE:
<223> OTHER INFORMATION: Synthetic Construct

<400> SEQUENCE: 2

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30
```

```
Val Ala Lys Asn Val Ile Met Phe Leu Gly Asp Gly Met Gly Val Ser
         35                  40                  45

Thr Val Thr Ala Ala Arg Ile Leu Lys Gly Gln Leu His His Asn Pro
 50                  55                  60

Gly Glu Glu Thr Arg Leu Glu Met Asp Lys Phe Pro Phe Val Ala Leu
 65                  70                  75                  80

Ser Lys Thr Tyr Asn Thr Asn Ala Gln Val Pro Asp Ser Ala Gly Thr
                 85                  90                  95

Ala Thr Ala Tyr Leu Cys Gly Val Lys Ala Asn Met Gly Thr Val Gly
                100                 105                 110

Val Ser Ala Ala Thr Glu Arg Ser Arg Cys Asn Thr Thr Gln Gly Asn
                115                 120                 125

Glu Val Thr Ser Ile Leu Arg Trp Ala Lys Asp Ala Gly Lys Ser Val
        130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
                180                 185                 190

His Asn Ile Arg Asp Ile Asp Val Ile Met Gly Gly Gly Arg Lys Tyr
        195                 200                 205

Met Tyr Pro Lys Gln Lys Thr Asp Val Glu Tyr Glu Ser Asp Glu Lys
        210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
                260                 265                 270

Phe Glu Pro Gly Asp Met Gln Tyr Glu Leu Asn Arg Asn Gln Val Thr
        275                 280                 285

Asp Pro Ser Leu Ser Glu Met Val Val Ala Ile Gln Ile Leu Arg
        290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
                340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
                420                 425                 430

Arg His Glu Thr His Gly Gly Glu Asp Val Ala Val Phe Ser Lys Gly
        435                 440                 445
```

```
Pro Met Ala His Leu Leu His Gly Val His Glu Gln Asn Tyr Val Pro
    450                 455                 460
His Val Met Ala Tyr Ala Ala Cys Ile Gly Ala Asn Leu Gly His Cys
465                 470                 475                 480
Ala Pro Ala Ser Ser
                485

<210> SEQ ID NO 3
<211> LENGTH: 491
<212> TYPE: PRT
<213> ORGANISM: Artificial Sequence
<220> FEATURE:
<223> OTHER INFORMATION: Synthetic Construct

<400> SEQUENCE: 3

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Met Gly Thr Val Gly
                100                 105                 110

Val Ser Ala Ala Thr Glu Arg Ser Arg Cys Asn Thr Thr Gln Gly Asn
            115                 120                 125

Glu Val Thr Ser Ile Leu Arg Trp Ala Lys Asp Ala Gly Lys Ser Val
130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
                180                 185                 190

His Asn Ile Arg Asp Ile Asp Val Ile Met Gly Gly Gly Arg Lys Tyr
            195                 200                 205

Met Tyr Pro Lys Gln Lys Thr Asp Val Glu Tyr Glu Ser Asp Glu Lys
210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
                260                 265                 270

Phe Glu Pro Gly Asp Met Gln Tyr Glu Leu Asn Arg Asn Gln Val Thr
            275                 280                 285

Asp Pro Ser Leu Ser Glu Met Val Val Val Ala Ile Gln Ile Leu Arg
290                 295                 300

Lys Asn Pro Lys Gly Phe Phe Leu Leu Val Glu Gly Gly Arg Ile Asp
305                 310                 315                 320
```

```
His Gly His His Glu Gly Lys Ala Lys Gln Ala Leu His Glu Ala Val
            325                 330                 335
Glu Met Asp Arg Ala Ile Gly Gln Ala Gly Ser Leu Thr Ser Ser Glu
        340                 345                 350
Asp Thr Leu Thr Val Val Thr Ala Asp His Ser His Val Phe Thr Phe
    355                 360                 365
Gly Gly Tyr Thr Pro Arg Gly Asn Ser Ile Phe Gly Leu Ala Pro Met
370                 375                 380
Leu Ser Asp Thr Asp Lys Lys Pro Phe Thr Ala Ile Leu Tyr Gly Asn
385                 390                 395                 400
Gly Pro Gly Tyr Lys Val Val Gly Gly Glu Arg Glu Asn Val Ser Met
                405                 410                 415
Val Asp Tyr Ala His Asn Asn Tyr Gln Ala Gln Ser Ala Val Pro Leu
            420                 425                 430
Arg His Glu Thr His Gly Gly Glu Asp Val Ala Val Phe Ser Lys Gly
        435                 440                 445
Pro Met Ala His Leu Leu His Gly Val His Glu Gln Asn Tyr Val Pro
    450                 455                 460
His Val Met Ala Tyr Ala Ala Cys Ile Gly Ala Asn Leu Gly His Cys
465                 470                 475                 480
Ala Pro Ala Ser Ser Ala Gly Ser Leu Ala Ala
                485                 490

<210> SEQ ID NO 4
<211> LENGTH: 223
<212> TYPE: PRT
<213> ORGANISM: Artificial Sequence
<220> FEATURE:
<223> OTHER INFORMATION: Synthetic Construct

<400> SEQUENCE: 4

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
            20                  25                  30
Pro Glu Val Thr Cys Val Val Asp Val Ser Gln Glu Asp Pro Glu
        35                  40                  45
Val Gln Phe Asn Trp Tyr Val Asp Gly Val Glu Val His Asn Ala Lys
    50                  55                  60
Thr Lys Pro Arg Glu Glu Gln Phe Asn Ser Thr Tyr Arg Val Val Ser
65                  70                  75                  80
Val Leu Thr Val Leu His Gln Asp Trp Leu Asn Gly Lys Glu Tyr Lys
                85                  90                  95
Cys Lys Val Ser Asn Lys Gly Leu Pro Ser Ser Ile Glu Lys Thr Ile
            100                 105                 110
Ser Lys Ala Lys Gly Gln Pro Arg Glu Pro Gln Val Tyr Thr Leu Pro
        115                 120                 125
Pro Ser Gln Glu Glu Met Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Asp Ser
                165                 170                 175
Asp Gly Ser Phe Phe Leu Tyr Ser Arg Leu Thr Val Asp Lys Ser Arg
            180                 185                 190
```

```
Trp Gln Glu Gly Asn Val Phe Ser Cys Ser Val Met His Glu Ala Leu
            195                 200                 205

His Asn His Tyr Thr Gln Lys Ser Leu Ser Leu Ser Leu Gly Lys
    210                 215                 220
```

<210> SEQ ID NO 5
<211> LENGTH: 724
<212> TYPE: PRT
<213> ORGANISM: Artificial Sequence
<220> FEATURE:
<223> OTHER INFORMATION: Synthetic Construct

<400> SEQUENCE: 5

```
Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Met Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Gln Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Gln Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335
```

```
Glu Met Asp Arg Ala Ile Gly Gln Ala Gly Ser Leu Thr Ser Ser Glu
                340                 345                 350

Asp Thr Leu Thr Val Val Thr Ala Asp His Ser His Val Phe Thr Phe
            355                 360                 365

Gly Gly Tyr Thr Pro Arg Gly Asn Ser Ile Phe Gly Leu Ala Pro Met
        370                 375                 380

Leu Ser Asp Thr Asp Lys Lys Pro Phe Thr Ala Ile Leu Tyr Gly Asn
385                 390                 395                 400

Gly Pro Gly Tyr Lys Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Ala Gly Ser Leu Ala Ala Val Glu Cys Pro Pro
                485                 490                 495

Cys Pro Ala Pro Pro Val Ala Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser Gln Glu Asp Pro Glu Val Gln Phe Asn Trp
530                 535                 540

Tyr Val Asp Gly Val Glu Val His Asn Ala Lys Thr Lys Pro Arg Glu
545                 550                 555                 560

Glu Gln Phe Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Gly Leu Pro Ser Ser Ile Glu Lys Thr Ile Ser Lys Ala Lys Gly
        595                 600                 605

Gln Pro Arg Glu Pro Gln Val Tyr Thr Leu Pro Pro Ser Gln Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Arg Leu Thr Val Asp Lys Ser Arg Trp Gln Glu Gly Asn
        675                 680                 685

Val Phe Ser Cys Ser Val Met His Glu Ala Leu His Asn His Tyr Thr
    690                 695                 700

Gln Lys Ser Leu Ser Leu Ser Leu Gly Lys Asp Asp Asp Asp Asp Asp
705                 710                 715                 720

Asp Asp Asp Asp

<210> SEQ ID NO 6
<211> LENGTH: 726
<212> TYPE: PRT
<213> ORGANISM: Artificial Sequence
```

<220> FEATURE:
<223> OTHER INFORMATION: Synthetic Construct

<400> SEQUENCE: 6

```
Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
            85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
            115                 120                 125

Glu Val Thr Ser Ile Leu Arg Trp Ala Lys Asp Ala Gly Lys Ser Val
            130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
            195                 200                 205

Met Tyr Pro Lys Asn Lys Thr Asp Val Glu Tyr Glu Ser Asp Glu Lys
210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
            275                 280                 285

Asp Pro Ser Leu Ser Glu Met Val Val Val Ala Ile Gln Ile Leu Arg
            290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
            355                 360                 365

Gly Gly Tyr Thr Pro Arg Gly Asn Ser Ile Phe Gly Leu Ala Pro Met
            370                 375                 380

Leu Ser Asp Thr Asp Lys Lys Pro Phe Thr Ala Ile Leu Tyr Gly Asn
385                 390                 395                 400
```

```
Gly Pro Gly Tyr Lys Val Val Gly Gly Glu Arg Glu Asn Val Ser Met
                405             410             415

Val Asp Tyr Ala His Asn Asn Tyr Gln Ala Gln Ser Ala Val Pro Leu
            420             425             430

Arg His Glu Thr His Gly Gly Glu Asp Val Ala Val Phe Ser Lys Gly
        435             440             445

Pro Met Ala His Leu Leu His Gly Val His Glu Gln Asn Tyr Val Pro
    450             455             460

His Val Met Ala Tyr Ala Ala Cys Ile Gly Ala Asn Leu Gly His Cys
465             470             475             480

Ala Pro Ala Ser Ser Leu Lys Asp Lys Thr His Thr Cys Pro Pro Cys
            485             490             495

Pro Ala Pro Glu Leu Leu Gly Gly Pro Ser Val Phe Leu Phe Pro Pro
            500             505             510

Lys Pro Lys Asp Thr Leu Met Ile Ser Arg Thr Pro Glu Val Thr Cys
            515             520             525

Val Val Val Asp Val Ser His Glu Asp Pro Glu Val Lys Phe Asn Trp
    530             535             540

Tyr Val Asp Gly Val Glu Val His Asn Ala Lys Thr Lys Pro Arg Glu
545             550             555             560

Glu Gln Tyr Asn Ser Thr Tyr Arg Val Val Ser Val Leu Thr Val Leu
            565             570             575

His Gln Asp Trp Leu Asn Gly Lys Glu Tyr Lys Cys Lys Val Ser Asn
            580             585             590

Lys Ala Leu Pro Ala Pro Ile Glu Lys Thr Ile Ser Lys Ala Lys Gly
            595             600             605

Gln Pro Arg Glu Pro Gln Val Tyr Thr Leu Pro Pro Ser Arg Glu Glu
    610             615             620

Met Thr Lys Asn Gln Val Ser Leu Thr Cys Leu Val Lys Gly Phe Tyr
625             630             635             640

Pro Ser Asp Ile Ala Val Glu Trp Glu Ser Asn Gly Gln Pro Glu Asn
            645             650             655

Asn Tyr Lys Thr Thr Pro Pro Val Leu Asp Ser Asp Gly Ser Phe Phe
            660             665             670

Leu Tyr Ser Lys Leu Thr Val Asp Lys Ser Arg Trp Gln Gln Gly Asn
            675             680             685

Val Phe Ser Cys Ser Val Met His Glu Ala Leu His Asn His Tyr Thr
    690             695             700

Gln Lys Ser Leu Ser Leu Ser Pro Gly Lys Asp Ile Asp Asp Asp Asp
705             710             715             720

Asp Asp Asp Asp Asp
                725
```

ALKALINE PHOSPHATASE POLYPEPTIDES AND METHODS OF USE THEREOF

SEQUENCE LISTING

The instant application contains a Sequence Listing which has been submitted electronically in ASCII format and is hereby incorporated by reference in its entirety. Said ASCII copy, created Feb. 10, 2022, is named 50694-094WO2_Sequence_Listing_2_4_22_ST25 and is 27,753 bytes in size.

BACKGROUND

Hypophosphatasia (HPP) is a rare, heritable skeletal disease with an incidence of 1 per 100,000 births for the most severe forms of the disease. The disorder typically results from loss-of-function mutations in the gene coding for tissue-nonspecific alkaline phosphatase (TNSALP). HPP exhibits a remarkable range of symptoms and severity, from premature tooth loss to almost complete absence of bone mineralization in utero. The presentation of HPP varies markedly among subjects and also varies markedly between subject ages. Many subjects with HPP display skeletal changes, short stature, chronic pain, painful lower limbs, gait disturbance, and premature, atraumatic tooth loss. Asfotase alfa (STRENSIQ®, Alexion Pharmaceuticals, Inc.), a recombinantly produced enzyme replacement therapy (ERT) that includes a soluble fragment of TNSALP, is the first ERT available to HPP subjects. Asfotase alfa has shown transformative effects on the most severe form of HPP, as evidenced by improvements in bone mineralization and density, as well as respiratory and motor function, cognitive development, and muscle strength (Whyte et al., *New Engl. J. Med.* 366:904-913, 2012).

SUMMARY

A first aspect features a pharmaceutical composition containing an alkaline phosphatase polypeptide with at least 80% (e.g., at least 85%, 90%, 95%, 97%, 99%, or 100%) sequence identity to SEQ ID NO: 5 and a pharmaceutically acceptable carrier. The polypeptide may include at least one mutation selected from E108M, N213Q, and N286Q relative to the amino acid sequence of SEQ ID NO: 1 (e.g., the polypeptide may contain two or all three of these mutations). For example, the polypeptide has at least 80% (e.g., at least 85%, 90%, 95%, 97%, 99%, or 100%) sequence identity to the amino acid sequence of SEQ ID NO: 5 and contains at least one, two, or all three of the mutations selected from E108M, N213Q, and N286Q. The pharmaceutically acceptable carrier may include one or more of phosphate, proline, and sucrose. For example, the polypeptide may include or consist of the amino acid sequence of SEQ ID NO: 5.

In some embodiments, the alkaline phosphatase portion of polypeptide has at least 80% (e.g., at least 85%, 90%, 95%, 97%, 99%, or 100%) sequence identity to SEQ ID NO: 3. This polypeptide may further be connected to an Fc region (e.g., a IgG1, IgG2, IgG3, or IgG4 Fc region) and/or a polyaspartate region. In some embodiments, the polypeptide includes an IgG2/4 Fc region, e.g., having have at least 80% (e.g., at least 85%, 90%, 95%, 97%, 99%, or 100%) identify to SEQ ID NO: 4. The polyaspartate may include, e.g., 3, 4, 5, 6, 7, 8, 9, 10, 11, 12, 13, 14, 15, 16, 17, 18, 19, or 20 aspartate residues. In some embodiments, the polyaspartate includes ten aspartate residues (D10).

The composition may be formulated to contain a dosage of the alkaline phosphatase polypeptide of from about 0.1 mg/mL to about 200 mg/mL (e.g., about 1, 10, 20, 25, 50, 75, 100, 125, 150, 175, or 200 mg/mL. The composition may be formulated in a volume of about 0.1 mL to about 50 mL (e.g., about 0.1 to about 10 mL, e.g., about 0.1 mL, 0.2 mL, 0.3 mL, 0.4 mL, 0.5 mL, 0.6 mL, 0.7 mL, 0.8 mL, 0.9 mL, or 1.0 mL, e.g., about 1 mL to about 10 mL, e.g., about 2 mL, 3 mL, 4 mL, 5 mL, 6 mL, 7 mL, 8 mL, 9 mL, or 10 mL). In some embodiments, the composition is formulated in about 1 mL). For example, the composition may contain 100 mg/mL of an alkaline phosphatase polypeptide with at least 80% (e.g., at least 85%, 90%, 95%, 97%, or 99%) sequence identity to, or the sequence of, SEQ ID NO: 5 (e.g., the polypeptide contains at least one, two, or all three of the mutations selected from E108M, N213Q, and N286Q of SEQ ID NO: 5) and a pharmaceutically acceptable carrier.

The composition may include phosphate (e.g., sodium phosphate), e.g., in a concentration of from about 1 mM to about 100 mM, or from about 5 mM to about 20 mM, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, or 100 mM, e.g., about 10 mM. The composition may further include proline and/or sucrose. The composition may further include proline. The composition may further include sucrose. For example, the composition may include from about 1 mM to about 500 mM proline, e.g., from about 70 mM to about 280 mm, e.g., from about 50 mM to about 200 mM, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 300 mM, 400 mM, or 500 mM, e.g., about 140 mM proline and/or from about 1 mM to about 500 mM sucrose, e.g., from about 70 mM to about 280 mm, e.g., from about 50 mM to about 200 mM, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210, mM, 220 mM, 230 mM, 240 mM, 250 mM, 260 mM, 270 mM, 280 mM, 290 mM, 300 mM, 350 mM, 400 mM, 450 mM, or 500 mM, e.g., about 140 mM sucrose or about 210 mM sucrose. In some embodiments, the composition includes a molar ratio of proline:sucrose of about 1:0 to about 1:3, e.g., about 1:1. In some embodiments, the formulation includes from about 1 mM to about 500 mM proline (e.g., about 50 mM to about 200 mM proline, e.g., about 140 mM proline) and from about 1 mM to about 500 mM sucrose (e.g., about 40 mM to about 280 mM, e.g., about 50 mM to about 200 mM sucrose, e.g., about 140 mM or about 210 mM sucrose). In some embodiments, the formulation includes about 140 mM proline. In some embodiments, the formulation includes about 140 mM sucrose. In some embodiments, the formulation includes about 210 mM sucrose. In some embodiments, the formulation includes about 210 mM sucrose and does not include proline. In some embodiments, the formulation includes about 140 mM proline and about 140 mM sucrose. In some embodiments, the formulation includes about 140 mM proline and about 140 mM sucrose and about 10 mM phosphate (e.g., sodium phosphate). In some embodiments, the formulation includes about 210 mM sucrose and about 10 mM phosphate (e.g., sodium phosphate). The formulation may further include from about 0.01% to about 0.5% polyoxyethylene (20) sorbitan monooleate), e.g., from about 0.01% to about 0.1% polyoxyethylene (20) sorbitan monooleate, such as, e.g., about 0.05% polyoxyethylene (20) sorbitan monooleate. The polyoxyethylene (20) sorbitan monooleate may be, e.g., polysorbate 80 (PS80). In some embodiments, the composition is formulated at a pH of about pH 7.0 to about pH 7.6 (e.g., about pH 7.1, 7.2, 7.3, 7.4, 7.5, or 7.6, e.g., about pH 7.3). In some embodiments, the composition includes about 10 mM phosphate, about 140 mM proline, about 140 mM sucrose, and about 0.05% polyoxyethylene (20) sorbitan monooleate (e.g., PS80) at a pH of about 7.3.

The composition may be a pharmaceutical composition formulated as a solution containing the polypeptide (e.g., the polypeptide of SEQ ID NO: 5 and variants thereof with at least about 85% sequence identity thereto (e.g., the polypeptide is one that contains one, two, or all three of the mutations selected from E108M, N213Q, and N286Q of SEQ ID NO: 5)). The pharmaceutical composition may contain the polypeptide in an amount of, e.g., about 0.1 mg/mL to about 200 mg/mL, such as about 100 mg/mL. The pharmaceutical composition may be formulated for subcutaneous administration, e.g., at a dosage of the polypeptide of from about 0.1 mg/mL to about 10 mg/mL. The composition may be formulated in a solution in a volume of about 0.1 mL to about 50 mL (e.g., about 0.1 to about 10 mL, e.g., about 0.1 mL, 0.2 mL, 0.3 mL, 0.4 mL, 0.5 mL, 0.6 mL, 0.7 mL, 0.8 mL, 0.9 mL, or 1.0 mL, e.g., about 1 mL to about 10 mL, e.g., about 2 mL, 3 mL, 4 mL, 5 mL, 6 mL, 7 mL, 8 mL, 9 mL, or 10 mL). In some embodiments, the composition is formulated in about 1 mL. The solution may contain about 10 mM phosphate, about 140 mM proline, about 140 mM sucrose, and about 0.05% polyoxyethylene (20) sorbitan monooleate (e.g., PS80) at a pH of about 7.3.

Also featured is a vial containing the pharmaceutical composition as described herein. The vial may contain a solution (e.g., about 10 mM sodium phosphate, about 140 mM proline, about 140 mM sucrose, and about 0.05% polyoxyethylene (20) sorbitan monooleate (e.g., PS80) at a pH of about 7.3) containing the polypeptide (e.g., in an amount of about 0.1 mg to about 1.0 g (e.g., about 10 mg to about 200 mg)) in a volume of, e.g., from about 0.1 mL to about 10 mL (e.g., about 1 mL). The vial may contain the polypeptide in an amount of, e.g., about 0.1 mg/mL to about 500 mg/mL, about 1 mg/mL to about 200 mg/mL, about 50 mg/mL to about 150 mg/mL, or about 100 mg/mL. The polypeptide may have the amino acid sequence of SEQ ID NO: 5 or a variant thereof with at least 85% sequence identity thereto (e.g., the polypeptide is one that contains one, two, or all three of the mutations selected from E108M, N213Q, and N286Q of SEQ ID NO: 5).

A second aspect features a method of treating a bone mineralization disorder or a disease with bone manifestations (e.g., a disease selected from the group consisting of hypophosphatasia (HPP), bone fracture, osteoporosis, sclerosteosis, chondrocalcinosis, hypotonia, Duchenne's muscular dystrophy, tracheobronchomalacia, seizure, neurofibromatosis (e.g., NF-1), and craniosynostosis, or one or more symptoms thereof, in a subject (e.g., a human subject) in need thereof by administering to the subject the pharmaceutical composition of the first aspect. The composition may be administered in an amount and for a duration sufficient to treat the disease or to alleviate one or more symptoms thereof. The treatment may enhance bone formation in the subject. The polypeptide may be used to treat muscle weakness.

The polypeptide or a pharmaceutical composition containing the same may be administered at a dosage of from about 0.01 mg/kg to about 60 mg/kg (e.g., from about 0.1 mg/kg to about 50 mg/kg, e.g., from about 0.1 mg/kg to about 20 mg/kg, or, e.g., from about 0.1 mg/kg to about 10 mg/kg). The polypeptide may be administered once per day, week, month, or year (e.g., once per week). In some embodiments, the polypeptide is administered one or more times every 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The polypeptide may be administered once a week, once every two weeks, once every three weeks, once every four weeks or longer. The polypeptide may be administered at a dosage of from about 0.01 mg/kg/week to about 50 mg/kg/week (e.g., from about 0.01 mg/kg/week to about 40 mg/kg/week, e.g., from about 0.1 mg/kg/week to about 20 mg/kg/week, or, e.g., from about 0.1 mg/kg/week to about 10 mg/kg/week). The polypeptide may be administered for at least one day, one week, one month, one year, or longer (e.g., for the life of the subject).

The polypeptide or a pharmaceutical composition containing the same may be administered subcutaneously, intravenously, intramuscularly, sublingually, intrathecally, or intradermally. In particular, the polypeptide, or a composition containing the polypeptide, may be administered by subcutaneous or intravenous administration.

In some embodiments, the pharmaceutical composition is administered subcutaneously (e.g., in the abdomen or thigh). For example, from about 10 mg to about 100 mg (e.g., 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, e.g., about 15 mg, 45 mg, or 90 mg, such as about 15 mg, 45 mg, or 90 mg) may be administered to the subject subcutaneously, e.g., once or twice per week, e.g., for at least 1, 2, 3, 4, 5, 6, 7, 8, 9, 10, or more weeks, or for longer (e.g., for the life of the subject). The composition may be administered in a volume of, e.g., about 5 mL or less (e.g., 4.0 mL, 3.0 mL, 2.0 mL, 1.0 mL, 0.9 mL, 0.8 mL, 0.7 mL, 0.6 mL, 0.5 mL, 0.4 mL, 0.3 mL, 0.2 mL, or 0.1 mL, or in a volume in a range of from about 5 mL to about 0.1 mL).

In some embodiments, the pharmaceutical composition is administered intravenously (IV). For example, from about 10 mg to about 100 mg (e.g., about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, such as, e.g., about 15 mg, 45 mg, or 90 mg) may be administered to the subject intravenously, e.g., once or twice per week, e.g., for at least 1, 2, 3, 4, 5, 6, 7, 8, 9, 10, or more weeks (e.g., for 3 weeks), or for longer (e.g., for the life of the subject). For example, the pharmaceutical composition is administered by IV in a volume of about 5 mL or less (e.g., 4.0 mL, 3.0 mL, 2.0 mL, 1.0 mL, 0.9 mL, 0.8 mL, 0.7 mL, 0.6 mL, 0.5 mL, 0.4 mL, 0.3 mL, 0.2 mL, or 0.1 mL, or in a volume in a range of from about 5 mL to about 0.1 mL).

In some embodiments, the pharmaceutical composition is administered intravenously and subcutaneously (e.g., in the abdomen or thigh). For example, the pharmaceutical composition is administered in a treatment regimen that combines intravenous and subcutaneous (e.g., in the abdomen or thigh) administration. For example, the composition may first be administered to a subject intravenously in a single dose in an amount of from about 10 mg to about 100 mg (e.g., about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, such as, e.g., about 15 mg, 45 mg, or 90 mg) followed by subcutaneous administration (e.g., in the abdomen or thigh) to the subject in one or more doses over time. For example, the subcutaneous dose may be from about 10 mg to about 100 mg (e.g., about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, e.g., about 15 mg, 45 mg, or 90 mg, such as about 15 mg, 45 mg, or 90 mg). The subcutaneous doses may be administered, e.g., once or twice per week, once every two weeks, once every three weeks, or once every four weeks, e.g., for at least 1, 2, 3, 4, 5, 6, 7, 8, 9, 10, 20, 30, 40, or 50 or more weeks, or for longer (e.g., for 1-10 years, or for the life of the subject). The intravenous and subcutaneous doses may be administered in a volume of, e.g., about 5 mL or less (e.g., 4.0 mL, 3.0 mL, 2.0 mL, 1.0 mL, 0.9 mL, 0.8 mL, 0.7 mL, 0.6 mL, 0.5 mL, 0.4 mL, 0.3 mL, 0.2 mL, or 0.1 mL, or in a volume in a range of from about 5 mL to about 0.1 mL).

The subject may be a human subject, such as a neonate, an infant, a child, an adolescent, or an adult.

In some embodiments, the TSAC of the recombinant alkaline phosphatase polypeptide is about 1.0 mol/mol to about 6.0 mol/mol. In some embodiments, the TSAC is about 1.2 mol/mol to about 6.0 mol/mol recombinant alkaline phosphatase. In some embodiments, the TSAC is about 1.5 mol/mol to about 6.0 mol/mol recombinant alkaline phosphatase. In some embodiments, the TSAC is about 3.0 mol/mol to about 6.0 mol/mol recombinant alkaline phosphatase. In some embodiments, the TSAC is about 3.2 mol/mol to about 5.9 mol/mol recombinant alkaline phosphatase. In some embodiments, the TSAC is about 0.9 mol/mol, about 1.0 mol/mol, about 1.1 mol/mol, about 1.2 mol/mol, about 1.3 mol/mol, about 1.4 mol/mol, about 1.5 mol/mol, about 1.6 mol/mol, about 1.7 mol/mol, about 1.8 mol/mol, about 1.9 mol/mol, about 2.0 mol/mol, about 2.1 mol/mol, about 2.2 mol/mol, about 2.3 mol/mol, about 2.4 mol/mol, about 2.5 mol/mol, about 2.6 mol/mol, about 2.7 mol/mol, about 2.8 mol/mol, about 2.9 mol/mol, about 3.0 mol/mol, about 3.1 mol/mol, about 3.2 mol/mol, about 3.3 mol/mol, about 3.4 mol/mol, about 3.5 mol/mol, about 3.6 mol/mol, about 3.7 mol/mol, about 3.8 mol/mol, about 3.9 mol/mol, about 4.0 mol/mol, about 4.1 mol/mol, about 4.2 mol/mol, about 4.3 mol/mol, about 4.4 mol/mol, about 4.5 mol/mol, about 4.6 mol/mol, about 4.7 mol/mol, about 4.8 mol/mol, about 4.9 mol/mol, about 5.0 mol/mol, about 5.1 mol/mol, about 5.2 mol/mol, about 5.3 mol/mol, about 5.4 mol/mol, about 5.5 mol/mol, about 5.6 mol/mol, about 5.7 mol/mol, about 5.8 mol/mol, about 5.9 mol/mol, or about 6.0 mol/mol recombinant alkaline phosphatase. In some embodiments, the TSAC is about 3.2 mol/mol recombinant alkaline phosphatase. In some embodiments, the TSAC is about 5.0 mol/mol recombinant alkaline phosphatase. In some embodiments, the TSAC is about 5.9 mol/mol recombinant alkaline phosphatase.

In some embodiments, the composition includes about 10 mM phosphate, about 140 mM proline, about 140 mM sucrose, about 0.05% polyoxyethylene (20) sorbitan monooleate (e.g., PS80) at a pH of about 7.3, and a TSAC value of from about 3.0 mol/mol to about 6.0 mol/mol.

In some embodiments, the method produces an $AUC_{0-168h}$ of from about 50 μg×hour/mL to about 4000 μg×hour/mL in the blood of the subject. For example, the method may produce an $AUC_{0-168h}$ of from about 1000 μg×hour/mL to about 3000 μg×hour/mL in the blood of the subject. In some embodiments, the method produces a $C_{max}$ of from about 0.5 μg/mL to about 25 μg/mL in the blood of the subject. For example, the method may produce a $C_{max}$ of from about 0.6 μg/mL to about 20 μg/mL in the blood of the subject.

Definitions

The term "about" means ±10% of the recited value. All measurements reported herein are understood to be modified by the term "about," whether or not the term is explicitly used, unless explicitly stated otherwise.

The term "bone-targeting moiety" means an amino acid sequence of at least 3 amino acid residues in length having a sufficient affinity to bone matrix such that the bone-targeting moiety, taken alone, has an in vivo binding affinity to the bone matrix that is at least about $1\times10^{-6}$ M or greater, e.g., about $10^{-6}$ M, about $10^{-7}$ M, about $10^{-8}$ M, about $10^{-9}$ M, or greater).

The term "catalytically competent," as used herein, refers to a sALP that hydrolyzes the bone mineralization inhibitor inorganic pyrophosphate (PPi) to provide inorganic phosphate (Pi), thereby decreasing the extracellular concentrations of PPi. Thus, a catalytically competent sALP improves skeletal mineralization by regulating the concentration of PPi.

The term "Fc" means a fragment crystallizable region of an immunoglobulin, e.g., IgG1, IgG2, IgG3, or IgG4, including the CH2 and CH3 domains of the immunoglobulin heavy chain. Fc may also include any portion of the hinge region joining the Fab and Fc regions. The Fc can be derived from any mammal, including a human, and may be post-translationally modified (e.g., by glycosylation or sialylation). In a non-limiting example, Fc can be the fragment crystallizable region of human IgG2/4 of SEQ ID NO: 4.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 500, 600, 700, 800, 900, 1,000, 1100, 1200, 1300, 1400, 1500, 1600, 1700, 1800, 1900, 2000, 2100, or more nucleotides, up to the entire length of the nucleic acid molecule, or 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide.

The terms "hypophosphatasia" and "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNSALP). HPP may be further characterized as infantile HPP, childhood HPP, perinatal HPP (e.g., benign perinatal HPP or lethal perinatal HPP), odonto-HPP, adolescent HPP, or adult HPP. For instance, "childhood HPP" describes a subject having HPP that is from about 5 years of age to about 12 years, "adolescent HPP" describes a subject having HPP that is from about 13 years of age to about 17 years, and "adult HPP" describes a subject having HPP that is about 18 years of age or older. The term "adult HPP," as used herein, refers to a condition or phenotype characterized by the presence of one or more of the following symptoms:

elevated blood and/or urine levels of inorganic pyrophosphate (PPi), hypomineralization, hypercalciuria, one or more skeletal deformities, hypotonia, muscle weakness, rheumatoid complications, waddling gait, ambulatory difficulties, bone pain, pain, bone fracture, calcium pyrophosphate dihydrate crystal deposition, pseudogout, arthritis, pyrophosphate arthropathy, chondrocalcinosis, calcific periarthritis, and pseudofracture. The term "adolescent HPP," as used herein, refers to a condition or phenotype characterized by the presence of one or more of the following symptoms: elevated blood or urine levels of PPi, PEA, or PLP; osteomalacia, one or more skeletal deformities, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay. The term "childhood HPP," as used herein, refers to refers to a condition or phenotype characterized by the presence of one or more of the following symptoms: elevated blood or urine levels of PPi, PEA, or PLP; rickets, rachitic ribs, one or more skeletal deformities, hypotonia, muscle weakness, rheumatoid complications, arthritis, pseudogout, waddling gait, ambulatory difficulties, bone pain, pain, premature loss of teeth, hypomineralization, delayed motor development, seizures, hypercalciuria, short stature, bone fracture, pseudofracture, and growth delay.

The term "nucleic acid" or "nucleic acid molecule" means a polymeric molecule, e.g., RNA or DNA, having a sequence of two or more covalently bonded, naturally occurring or modified, nucleotides. The nucleic acid molecule may be, e.g., single or double stranded, and may include modified or unmodified nucleotides, or mixtures or combinations thereof. Various salts, mixed salts, and free acid forms of nucleic acid molecules are also included.

By "treating," "treat," and "treatment" is meant the medical management of a subject with the intent to cure, ameliorate, stabilize, reduce the likelihood of, or prevent a disease condition, such as HPP (e.g., child, adolescent, or adult HPP), or one or more symptoms thereof and/or the management of a subject exhibiting or likely to have a disease condition, such as HPP, e.g., by administering a pharmaceutical composition (e.g., an sALP as described herein). Treating (and the other forms used herein) includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a subject who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

The terms "peptide," "polypeptide," and "protein" are used interchangeably and refer to any chain of two or more natural or unnatural amino acid residues, regardless of post-translational modification (e.g., glycosylation, sialylation, or phosphorylation), constituting all or part of a naturally-occurring or non-naturally occurring polypeptide or peptide, as is described herein.

The terms "sALP," "soluble alkaline phosphatase," and "extracellular domain of an alkaline phosphatase" are used interchangeably (unless the context indicates otherwise) to mean a soluble, non-membrane-bound alkaline phosphatase or a biologically active fragment or variant thereof. sALPs include, for example, an alkaline phosphatase lacking a C-terminal GPI signal sequence, and additional variants and analogs thereof which retain alkaline phosphatase activity, e.g., the ability to hydrolyze PPi or other natural or artificial substrate(s). This includes soluble fragments corresponding to the extracellular domains of TNSALP, PALP, GLALP, and IALP and biologically active fragments or variants thereof, unless specified otherwise. A mature sALP lacks the GPI membrane anchor and the signal peptide, which is cleaved during processing.

The terms "ALP" and "alkaline phosphatase" refer to a naturally occurring alkaline phosphatase, such as TNSALP, PALP, GLALP, and IALP, which is able to hydrolyze PPi or other natural or artificial substrates.

The term "pharmaceutically acceptable carrier" or "pharmaceutically acceptable excipient" is meant a carrier or excipient that is physiologically acceptable to the treated subject while retaining the therapeutic properties of the compound with which it is administered. One exemplary pharmaceutically acceptable carrier substance is physiological saline. Other physiologically acceptable carriers and their formulations are known to those skilled in the art and described, for example, in *Remington's Pharmaceutical Sciences* (Remington: The Science and Practice of Pharmacy, 22nd Ed., Allen, Ed. 2012).

The term "pharmaceutical composition" means a composition containing a polypeptide or nucleic acid molecule as described herein formulated with a pharmaceutically acceptable excipient, and includes those that are manufactured or sold with the approval of a governmental regulatory agency as part of a therapeutic regimen for the treatment or prevention of a disease or event in a subject. Pharmaceutical compositions can be formulated, for example, for subcutaneous administration (e.g., in the abdomen or thigh), intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The term "subject" means a mammal, including, but not limited to, a human or non-human mammal, such as a bovine, equine, canine, ovine, or feline.

The term "therapeutically effective amount" means an amount of a polypeptide or nucleic acid molecule described herein that is sufficient to substantially treat, prevent, delay, suppress, or arrest any symptom of a disease or condition described herein, particularly HPP. A therapeutically effective amount of a composition described herein may depend on the severity of the disorder being treated and the condition, weight, and general state of the subject and can be determined by an ordinarily-skilled artisan with consideration of such factors. A therapeutically effective amount of a composition described herein can be administered to a subject in a single dose or in multiple doses administered over a period of time.

The terms "Total Sialic Acid Content" or "TSAC," as used herein, refer to the amount of sialic acid (a carbohydrate) on a particular protein molecule. It is expressed as moles sialic acid incorporated per mole of protein, or "mol/mol." TSAC concentration is measured during the purification process. For example, one method of TSAC quantitation is where TSAC is released from the alkaline phosphatase using acid hydrolysis, and the released TSAC is subsequently detected via electrochemical detection using high-performance anion-exchange chromatography with pulsed amperometric detection technique ("HPAE-PAD").

The term "sialic acid" refers generally to N- or O-substituted derivatives of neuraminic acid, a monosaccharide with a nine-carbon backbone. Sialic acid may also refer specifically to the compound N-acetylneuraminic acid and is sometimes abbreviated as Neu5Ac or NANA. Presence of sialic acid may affect absorption, serum half-life, and clearance of glycoproteins from the serum, as well as physical, chemical, and immunogenic properties of the glycoprotein. In some embodiments of the present disclosure, sialic acid associated with alkaline phosphatases, e.g., ALP201, impacts in vivo exposure and the half-life of the molecule in physiological conditions. In some embodiments, precise and predictable control of total sialic acid content (TSAC) of an alkaline phosphatase serves as a quality control attribute.

As used herein, when a polypeptide or nucleic acid sequence is referred to as having "at least X % sequence identity" to a reference sequence, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, Advances in Applied Mathematics, 482-489, 1981) as incorporated into GENEMATCHER PLUS™ (Schwarz and Dayhof, *Atlas of Protein Sequence and Structure*, Dayhoff, M. O., Ed., pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

The words "preferred" and "preferably" refer to embodiments of the disclosed compounds, compositions and methods that may afford certain benefits, under certain circumstances. However, other embodiments may also be preferred, under the same or other circumstances. Furthermore, the recitation of one or more preferred embodiments does not imply that other embodiments are not useful, and the use of this term is not intended to exclude other embodiments from the scope of the disclosure.

For any method disclosed herein that includes discrete steps, the steps may be conducted in any feasible order; also, as appropriate, any combination of two or more steps may be conducted simultaneously.

The above summary is not intended to describe each disclosed embodiment or every implementation of disclosed compounds, compositions and methods. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

BRIEF DESCRIPTION OF THE DRAWINGS

FIG. 2 is a set of saturation curves showing the relationship of increasing PLP levels with rate of PLP hydrolysis for ALP201 (left) and asfotase alfa (right).

DETAILED DESCRIPTION

Figure 1:
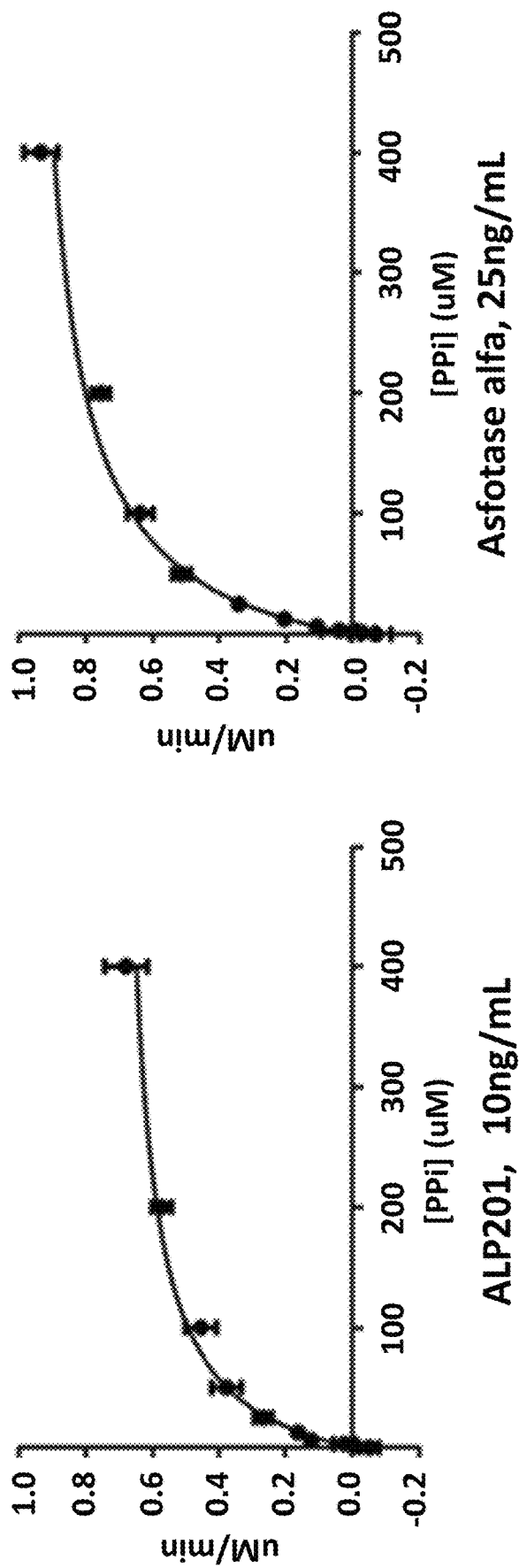
FIG. 1 is a set of saturation curves showing the relationship of increasing PPi levels with rate of PPi hydrolysis for ALP201 (SEQ ID NO: 5; left) and asfotase alfa (SEQ ID NO: 6; right).

Featured are soluble alkaline phosphatases polypeptides (e.g., those having the sequence of SEQ ID NO: 5 and variants thereof with up to 80% or more sequence identity thereto, in which the polypeptides contain one, two, or all three of the mutations selected from E108M, N213Q, and N286Q of SEQ ID NO: 5), fragments thereof, and fusion proteins thereof, nucleic acid molecules encoding the same, and methods of using the polypeptides and nucleic acid molecules for treating a disease, such as a bone mineralization disorder, for example hypophosphatasia (HPP), or one or more symptoms thereof. The polypeptides include a soluble alkaline phosphatase (sALP) or fragment thereof, which is derived from a naturally occurring alkaline phosphatase (ALP). Alkaline phosphatases include various isozymes that are differentially expressed in different tissues. Four major ALP isozymes include tissue non-specific alkaline phosphatase (TNSALP), placental alkaline phosphatase (PALP), germ line alkaline phosphatase (GLALP), and intestinal alkaline phosphatase (IALP). Accordingly, featured are proteins derived from these ALP isozymes.

The polypeptides described herein are formulated into pharmaceutical compositions containing for example, one or more of phosphate, proline, and sucrose. These components impart beneficial features for the polypeptide, such as improved stability, reduced aggregation, reduction of truncated protein products, and increased purity of desired protein products in the formulation.

HPP is a rare, heritable skeletal disease with an incidence of 1 per 100,000 births for the most severe forms of the disease. The disorder typically results from loss-of-function mutations in the gene coding for TNSALP. HPP exhibits a remarkable range of symptoms and severity, from premature tooth loss to almost complete absence of bone mineralization in utero. The presentation of HPP varies markedly among subjects and also varies markedly between subject ages. Many subjects with HPP display skeletal changes, short stature, chronic pain, painful lower limbs, gait disturbance, and premature, atraumatic tooth loss. Due to the loss-of-function mutation in the endogenous TNSALP, a subject with HPP requires functional ALP activity of the polypeptides described herein to restore the native ALP activity and provide normal bone matrix mineralization.

Soluble Alkaline Phosphatase Polypeptides

The polypeptides described herein include a soluble alkaline phosphatase (sALP), such as a mutant tissue nonspecific alkaline phosphatase (TNSALP) or fragment thereof. The sALP may be fused to an Fc region and a polyaspartate of sequence n ("Dn", in which n equals, e.g., 3-20) (sALP-Fc-Dn). The polypeptide may include a human TNSALP, such as a soluble fragment of a human TNSALP (e.g., residues 1-491 or 1-485 of SEQ ID NO: 1). The polypeptide may include one, two, or all three of the mutations E108M, N213Q, and/or N286Q relative to SEQ ID NO: 1. For example, the sALP may have at least 80% (e.g., at least 85%, 90%, 95%, 97%, 99%, or 100%) identify to SEQ ID NO: 2 or 3. The Fc region may be an IgG2/4 Fc region. For example, the Fc region may have at least 80% (e.g., at least 85%, 90%, 95%, 97%, 99%, or 100%) identify to SEQ ID NO: 4. The polyaspartate may include, e.g., 3, 4, 5, 6, 7, 8, 9, 10, 11, 12, 13, 14, 15, 16, 17, 18, 19, or 20 aspartate residues. In some embodiments, the polyaspartate includes ten aspartate residues (D10). In some embodiments, the polypeptide has at least 80% (e.g., at least 85%, 90%, 95%, 97%, 99%, or 100%) identify to SEQ ID NO: 5. For example, the polypeptide may include or consist of the polypeptide of SEQ ID NO: 5. The polypeptide may consist of SEQ ID NO: 5.

In some embodiments, the alkaline phosphatase portion of polypeptide has at least 80% (e.g., at least 85%, 90%, 95%, 97%, 99%, 01100%) sequence identity to SEQ ID NO: 3. This polypeptide may further be connected to an Fc region (e.g., a IgG1, IgG2, IgG3, or IgG4 Fc region) and/or a polyaspartate region. In some embodiments, the polypeptide includes an IgG2/4 Fc region, e.g., having have at least 80% (e.g., at least 85%, 90%, 95%, 97%, 99%, or 100%) identify to SEQ ID NO: 4. The polyaspartate may include, e.g., 3, 4, 5, 6, 7, 8, 9, 10, 11, 12, 13, 14, 15, 16, 17, 18, 19, or 20 aspartate residues. In some embodiments, the polyaspartate includes ten aspartate residues (D10).

```
Human TNSALP lacking a signal peptide
(UniProt P05186.4)
                                      SEQ ID NO: 1
LVPEKEKDPKYVVRDQAQETLKYALELQKLNTNVA

KNVIMFLGDGMGVSTVTAARILKGQLHHNPGEETR

LEMDKFPFVALSKTYNTNAQVPDSAGTATAYLCGV

KANEGTVGVSAATERSRCNTTQGNEVTSILRWAKD

AGKSVGIVTTTRVNHATPSAAYAHSADRDWYSDNE

MPPEALSQGCKDIAYQLMHNIRDIDVIMGGGRKYM

YPKNKTDVEYESDEKARGTRLDGLDLVDTVVKSFK

PRYKHSHFIWNRTELLTLDPHNVDYLLGLFEPGDM

QYELNRNNVTDPSLSEMVVVAIQILRKNPKGFFLL

VEGGRIDHGHHEGKAKQALHEAVEMDRAIGQAGSL

TSSEDTLTVVTADHSHVFTFGGYTPRGNSIFGLAP

MLSDTDKKPFTAILYGNGPGYKVVGGERENVSMVD

YAHNNYQAQSAVPLRHETHGGEDVAVFSKGPMAHL

LHGVHEQNYVPHVMAYAACIGANLGHCAPASSAGS

LAAGPLLLALALYPLSVLF

Human TNSALP (1-485; E108M, N213Q, N286Q)
                                      SEQ ID NO: 2
LVPEKEKDPKYWRDQAQETLKYALELQKLNTNVAK

NVIMFLGDGMGVSTVTAARILKGQLHHNPGEETRL

EMDKFPFVALSKTYNTNAQVPDSAGTATAYLCGVK

ANMGTVGVSAATERSRCNTTQGNEVTSILRWAKDA

GKSVGIVTTTRVNHATPSAAYAHSADRDWYSDNEM

PPEALSQGCKDIAYQLMHNIRDIDVIMGGGRKYMY

PKQKTDVEYESDEKARGTRLDGLDLVDTWKSFKPR

YKHSHFIWNRTELLTLDPHNVDYLLGLFEPGDMQY

ELNRNQVTDPSLSEMVVVAIQILRKNPKGFFLLVE

GGRIDHGHHEGKAKQALHEAVEMDRAIGQAGSLTS

SEDTLTVVTADHSHVFTFGGYTPRGNSIFGLAPML

SDTDKKPFTAILYGNGPGYKVVGGERENVSMVDYA
```

-continued

HNNYQAQSAVPLRHETHGGEDVAVFSKGPMAHLLH

GVHEQNYVPHVMAYAACIGANLGHCAPASS

Human TNSALP (1-491; E108M, N213Q, N286Q)
SEQ ID NO: 3
LVPEKEKDPKYWRDQAQETLKYALELQKLNTNVAK

NVIMFLGDGMGVSTVTAARILKGQLHHNPGEETRL

EMDKFPFVALSKTYNTNAQVPDSAGTATAYLCGVK

ANMGTVGVSAATERSRCNTTQGNEVTSILRWAKDA

GKSVGIVTTTRVNHATPSAAYAHSADRDWYSDNEM

PPEALSQGCKDIAYQLMHNIRDIDVIMGGGRKYMY

PKQKTDVEYESDEKARGTRLDGLDLVDTWKSFKPR

YKHSHFIWNRTELLTLDPHNVDYLLGLFEPGDMQY

ELNRNQVTDPSLSEMVVVAIQILRKNPKGFFLLVE

GGRIDHGHHEGKAKQALHEAVEMDRAIGQAGSLTS

SEDTLTVVTADHSHVFTFGGYTPRGNSIFGLAPML

SDTDKKPFTAILYGNGPGYKVVGGERENVSMVDYA

HNNYQAQSAVPLRHETHGGEDVAVFSKGPMAHLLH

GVHEQNYVPHVMAYAACIGANLGHCAPASSAGSLA

A

IgG2/4 Fc
SEQ ID NO: 4
VECPPCPAPPVAGPSVFLFPPKPKDTLMISRTPEV

TCVVVDVSQEDPEVQFNWYVDGVEVHNAKTKPREE

QFNSTYRVVSVLTVLHQDWLNGKEYKCKVSNKGLP

SSIEKTISKAKGQPREPQVYTLPPSQEEMTKNQVS

LTCLVKGFYPSDIAVEWESNGQPENNYKTTPPVLD

SDGSFFLYSRLTVDKSRWQEGNVFSCSVMHEALHN

HYTQKSLSLSLGK

ALP201
SEQ ID NO: 5
LVPEKEKDPKYWRDQAQETLKYALELQKLNTNVAK

NVIMFLGDGMGVSTVTAARILKGQLHHNPGEETRL

EMDKFPFVALSKTYNTNAQVPDSAGTATAYLCGVK

ANMGTVGVSAATERSRCNTTQGNEVTSILRWAKDA

GKSVGIVTTTRVNHATPSAAYAHSADRDWYSDNEM

PPEALSQGCKDIAYQLMHNIRDIDVIMGGGRKYMY

PKQKTDVEYESDEKARGTRLDGLDLVDTWKSFKPR

YKHSHFIWNRTELLTLDPHNVDYLLGLFEPGDMQY

ELNRNQVTDPSLSEMVVVAIQILRKNPKGFFLLVE

GGRIDHGHHEGKAKQALHEAVEMDRAIGQAGSLTS

SEDTLTVVTADHSHVFTFGGYTPRGNSIFGLAPML

SDTDKKPFTAILYGNGPGYKVVGGERENVSMVDYA

HNNYQAQSAVPLRHETHGGEDVAVFSKGPMAHLLH

GVHEQNYVPHVMAYAACIGANLGHCAPASSAGSLA

AVECPPCPAPPVAGPSVFLFPPKPKDTLMISRTPE

VTCVVVDVSQEDPEVQFNWYVDGVEVHNAKTKPRE

EQFNSTYRVVSVLTVLHQDVVLNGKEYKCKVSNKG

LPSSIEKTISKAKGQPREPQVYTLPPSQEEMTKNQ

VSLTCLVKGFYPSDIAVEVVESNGQPENNYKTTPP

VLDSDGSFFLYSRLTVDKSRWQEGNVFSCSVMHEA

LHNHYTQKSLSLSLGKDDDDDDDDDD asfotase alfa
SEQ ID NO: 6
LVPEKEKDPKYVVRDQAQETLKYALELQKLNTNVA

KNVIMFLGDGMGVSTVTAARILKGQLHHNPGEETR

LEMDKFPFVALSKTYNTNAQVPDSAGTATAYLCGV

KANEGTVGVSAATERSRCNTTQGNEVTSILRWAKD

AGKSVGIVTTTRVNHATPSAAYAHSADRDVVYSDN

EMPPEALSQGCKDIAYQLMHNIRDIDVIMGGGRKY

MYPKNKTDVEYESDEKARGTRLDGLDLVDTVVKSF

KPRYKHSHFIWNRTELLTLDPHNVDYLLGLFEPGD

MQYELNRNNVTDPSLSEMVVVAIQILRKNPKGFFL

LVEGGRIDHGHHEGKAKQALHEAVEMDRAIGQAGS

LTSSEDTLTVVTADHSHVFTFGGYTPRGNSIFGLA

PMLSDTDKKPFTAILYGNGPGYKVVGGERENVSMV

DYAHNNYQAQSAVPLRHETHGGEDVAVFSKGPMAH

LLHGVHEQNYVPHVMAYAACIGANLGHCAPASSLK

DKTHTCPPCPAPELLGGPSVFLFPPKPKDTLMISR

TPEVTCVVVDVSHEDPEVKFNWYVDGVEVHNAKTK

PREEQYNSTYRVVSVLTVLHQDWLNGKEYKCKVSN

KALPAPIEKTISKAKGQPREPQVYTLPPSREEMTK

NQVSLTCLVKGFYPSDIAVEWESNGQPENNYKTTP

PVLDSDGSFFLYSKLTVDKSRWQQGNVFSCSVMHE

ALHNHYTQKSLSLSPGKDIDDDDDDDDDD

Total Sialic Acid Content

As described herein, TSAC may impact the half-life of the recombinant alkaline phosphatase in physiological conditions. Thus, the TSAC level may serve as a quality attribute for recombinantly-produced alkaline phosphatases such as, e.g., ALP201. Control of the TSAC range during manufacturing of the polypeptide can improve reproducibility batch to batch and can reduce heterogeneity in the produced polypeptides. In some embodiments, the TSAC is about 0.8 mol/mol to about 8.0 mol/mol of the recombinant alkaline phosphatase. In some embodiments, the TSAC is about 0.9 mol/mol to about 7.0 mol/mol of the recombinant alkaline phosphatase. In some embodiments, the TSAC is about 1.0 mol/mol to about 6.0 mol/mol of the recombinant alkaline phosphatase. In some embodiments, the TSAC is about 1.2 mol/mol to about 6.0 mol/mol of the recombinant alkaline phosphatase. In some embodiments, the TSAC is about 1.5 mol/mol to about 6.0 mol/mol of the recombinant alkaline phosphatase. In some embodiments, the TSAC is about 2.0 mol/mol to about 6.0 mol/mol of the recombinant alkaline phosphatase. In some embodiments, the TSAC is about 3.2 mol/mol to about 5.9 mol/mol of the recombinant alkaline phosphatase. In some embodiments, the TSAC is about 0.9 mol/mol, about 1.0 mol/mol, about 1.1 mol/mol, about 1.2 mol/mol, about 1.3 mol/mol, about 1.4 mol/mol, about 1.5 mol/mol, about 1.6 mol/mol, about 1.7 mol/mol, about 1.8 mol/mol, about 1.9 mol/mol, about 2.0 mol/mol, about 2.1 mol/mol, about 2.2 mol/mol, about 2.3 mol/mol, about 2.4 mol/mol, about 2.5 mol/mol, about 2.6 mol/mol, about 2.7 mol/mol, about 2.8 mol/mol, about 2.9 mol/mol, about 3.0 mol/mol, about 3.1 mol/mol, about 3.2 mol/mol, about 3.3 mol/mol, about 3.4 mol/mol, about 3.5 mol/mol, about 3.6 mol/mol, about 3.7 mol/mol, about 3.8 mol/mol, about 3.9 mol/mol, about 4.0 mol/mol, about 4.1 mol/mol, about 4.2 mol/mol, about 4.3 mol/mol, about 4.4 mol/mol, about 4.5 mol/mol, about 4.6 mol/mol, about 4.7 mol/mol, about 4.8 mol/mol, about 4.9 mol/mol, about 5.0 mol/mol, about 5.1 mol/mol, about 5.2 mol/mol, about 5.3 mol/mol, about 5.4 mol/mol, about 5.5 mol/mol, about 5.6 mol/mol, about 5.7 mol/mol, about 5.8 mol/mol, about 5.9 mol/mol, or about 6.0 mol/mol of the recombinant alkaline phosphatase. In some embodiments, the TSAC is about 3.2 mol/mol of the recombinant alkaline phosphatase. In some embodiments, the TSAC is about 5.0 mol/mol of the recombinant alkaline phosphatase. In some embodiments, the TSAC is about 5.9 mol/mol of the recombinant alkaline phosphatase.

Pharmaceutical Compositions

A polypeptide described herein (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or SEQ ID NO: 5)) can be formulated as a pharmaceutical composition by a variety of methods known in the art.

The composition may include one or more, or all, of phosphate, proline, and sucrose. The composition may include, for example, phosphate and sucrose. For example, the composition may include phosphate (e.g., sodium phosphate), at a concentration of, e.g., from about 1 mM to about 100 mM, or from about 5 mM to about 20 mM phosphate, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, or 100 mM, or, e.g., about 10 mM. The composition may further include proline and/or sucrose. The composition may further include proline. The composition may further include sucrose. For example, the composition may include from about 1 mM to about 500 mM proline, e.g., from about 70 mM to about 280 mM, e.g., from about 50 mM to about 200 mM, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 300 mM, 400 mM, or 500 mM, e.g., about 140 mM proline and/or from about 1 mM to about 500 mM sucrose, e.g., from about 70 mM to about 280 mM, e.g., from about 50 mM to about 200 mM, e.g., about 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, 220 mM, 230 mM, 240 mM, 250 mM, 260 mM, 270 mM, 280 mM, 290 mM, 300 mM, 350 mM, 400 mM, 450 mM, or 500 mM, e.g., about 140 mM sucrose or about 210 mM sucrose. In some embodiments, the composition includes a molar ratio of proline:sucrose of about 1:0 to about 1:3, e.g., about 1:1. In some embodiments, the composition includes about 140 mM proline. In some embodiments, the formulation includes about 140 mM sucrose. In some embodiments, the formulation includes about 210 mM sucrose. In some embodiments, the formulation includes about 210 mM sucrose and does not include proline. In some embodiments, the composition includes about 210 mM sucrose and about 10 mM phosphate (e.g., sodium phosphate). The formulation may further include from about 0.01% to about 0.5%, e.g., from about 0.01% to about 0.1%, e.g., about 0.05% polyoxyethylene (20) sorbitan monooleate (e.g., polysorbate 80 (PS80)). In some embodiments, the composition is formulated at a pH of about pH 7.0 to about pH 7.6 (e.g., about pH 7.1, 7.2, 7.3, 7.4, 7.5, or 7.6, e.g., about 7.3). In some embodiments, the composition includes about 10 mM phosphate, about 140 mM proline, about 140 mM sucrose, and about 0.05% polyoxyethylene (20) sorbitan monooleate (e.g., PS80) at a pH of about 7.3.

The composition may be formulated as a solution containing the polypeptide in an amount of, e.g., about 0.1 mg/mL to about 200 mg/mL, such as about 100 mg/mL. The composition may be formulated for intravenous or subcutaneous administration, e.g., at a dosage of the polypeptide of from about 0.1 mg/mL to about 10 mg/mL. The composition may be formulated in a solution in a volume of about 0.1 mL to about 50 mL (e.g., about 0.1 to about 10 mL, e.g., about 0.1 mL, 0.2 mL, 0.3 mL, 0.4 mL, 0.5 mL, 0.6 mL, 0.7 mL, 0.8 mL, 0.9 mL, or 1.0 mL, e.g., about 1 mL to about 10 mL, e.g., about 2 mL, 3 mL, 4 mL, 5 mL, 6 mL, 7 mL, 8 mL, 9 mL, or 10 mL). In some embodiments, the composition is formulated in about 1 mL.

The disclosure also features a vial containing a pharmaceutical composition as described herein. The vial may contain a solution in a volume of, e.g., from about 0.1 mL to about 10 mL (e.g., about 1 mL). The vial may contain the polypeptide in an amount of, e.g., about 0.1 mg/mL to about 500 mg/mL, e.g., about 1 mg/mL to about 200 mg/mL, e.g., about 50 mg/mL to about 150 mg/mL, e.g., about 100 mg/mL, of the polypeptide (e.g., a polypeptide of SEQ ID NO: 5 or a variant having at least 85% sequence identity thereto).

For example, the vial may contain a volume of about 0.25 mL, about 0.5 mL, about 0.75 mL, or about 1.0 mL of a solution containing the polypeptide of SEQ ID NO: 5 at a concentration of about 50 to about 100 mg/mL, in which the solution contains about 10 mM phosphate, about 140 mM proline, about 140 mM sucrose, and about 0.05% polyoxyethylene (20) sorbitan monooleate (e.g., PS80) at a pH of about 7.3.

Formulations

The compositions including sALPs and sALP fusion polypeptides (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or SEQ ID NO: 5)) can be formulated according to standard methods. For instance, the sALP composition can be formulated, for example, as a buffered solution at a suitable concentration and suitable for storage at 2-8° C. (e.g., 4° C.). The sALP composition can also be formulated for storage at a temperature below 0° C. (e.g., −20° C. or −80° C.). The sALP composition can further be formulated for storage for up to 2 years (e.g., one month, two months, three months, four months, five months, six months, seven months, eight months, nine months, 10 months, 11 months, 1 year, 1½ years, or 2 years) at 2-8° C.

(e.g., 4° C.). Thus, the compositions described herein can be formulated to be stable in storage for at least 1 year at 2-8° C. (e.g., 4° C.). A composition can be formulated in a suitable volume, e.g., a volume of about 0.1 mL to about 10 mL.

The compositions including sALPs and sALP fusion polypeptides (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be in liquid form.

For example, compositions intended for systemic or local delivery can be in the form of injectable or infusible solutions. Accordingly, the sALP composition (e.g., a composition containing a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be formulated for administration by a parenteral mode (e.g., subcutaneous, intravenous, intraperitoneal, or intramuscular injection). "Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion. Particular routes of administration include intravenous and subcutaneous administration.

The composition can be prepared as a lyophilized composition. The composition can be rehydrated with a solution (e.g., as described herein) prior to administration.

Dosage

The sALP polypeptide (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1)) described herein can be administered to a subject having or being prone to a bone mineralization disorder, such as HPP, in individual doses ranging, e.g., from 0.01 mg/kg to 500 mg/kg (e.g., from 0.05 mg/kg to 500 mg/kg, from 0.1 mg/kg to 60 mg/kg, from 0.1 mg/kg to 50 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For all dosages or ranges recited herein, the term "about" can be used to modify these dosages by ±10% of the recited values or range endpoints. In particular, compositions (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) in accordance with the present disclosure can be administered to a subject in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be administered to a subject in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 6 or about 9 mg/kg/week). In particular, the sALP can be administered one or more times per week (e.g., 1, 2, 3, 4, 5, 6, 7, or more times per week), one or more times every other week, or one or more times per month (e.g., once every 14 days, 15 days 16 days, 17 days, 18 days, 19 days, 20 days, 21 days, 22 days, 23 days, 24 days, 25 days, 26 days, 27 days, 28 days, 29 days, or 30 days). In some embodiments, the formulation is administered once per week. In some embodiments, the formulation is administered once every two weeks.

In particular, the sALP (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be administered at a dosage of 2 mg/kg three times a week (total dose 6 mg/kg/week), 1 mg/kg six times a week (total dose 6 mg/kg/week), 3 mg/kg three times a week (total dose 9 mg/kg/week), 0.5 mg/kg three times a week (total dose of 1.5 mg/kg/week), or 9.3 mg/kg three times a week (total dose 28 mg/kg/week). The dosage may be adapted by the clinician in accordance with conventional factors such as the extent of the disease and different parameters from the subject having or being prone to a bone mineralization disorder, such as HPP. Alternatively, about 0.1 mg/kg to about 20 mg/kg (e.g., about 0.1 mg/kg to about 9 mg/kg) can be administered one time per week or one time every two weeks. The sALP composition can also be administered 1-10 times (e.g., 1, 2, 3, 4, 5, 6, 7, 8, 9, and 10) per week or per two weeks at a dosage of 1-90 mg per dose (e.g., in a volume of 0.1 mL to 100 mL). In some embodiments, the sALP composition is administered once per week. In some embodiments, the sALP composition is administered once every two weeks.

A composition containing a sALP or a sALP fusion polypeptide (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be administered to a subject in either a single dosage regimen or a multiple dosage regimen. Doses can be administered, e.g., hourly, bi-hourly, daily, bi-daily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, ten times, eleven times, or twelve times per day, week, or month. In particular, the dosing regimen is once, twice, or thrice weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the subject having or being prone to a bone mineralization disorder, such as HPP. The amount, frequency, and duration of dosage can be adapted by the clinician in accordance with conventional factors such as the extent of the disease and different parameters from the subject having or being prone to a bone mineralization disorder, such as HPP.

For example, the dosage of a sALP or sALP fusion polypeptide (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) may be from about 0.1 mg/kg of body weight to about 10 mg/kg of body weight administered subcutaneously or intravenously one or more (e.g., 2, 3, 4, 5, 6, or 7) times per week.

In some particular embodiments, the polypeptide (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) or a pharmaceutical composition containing the same may be administered at a dosage of from about 0.01 mg/kg to about 60 mg/kg (e.g., from about 0.1 mg/kg to about 50 mg/kg, e.g., from about 0.1 mg/kg to about 20 mg/kg, e.g., from about 0.1 mg/kg to about 10 mg/kg). The polypeptide may be administered once per day, week, month, or year (e.g., once per week). In some embodiments, the polypeptide is administered one or more times every 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The polypeptide may be administered at a dosage of from about 0.01 mg/kg/week to about 50 mg/kg/week (e.g., from about 0.01 mg/kg/week to about 40 mg/kg/week, e.g., from about 0.1 mg/kg/week to about 20 mg/kg/week, e.g., from about 0.1 mg/kg/week to about 10 mg/kg/week). The polypeptide may be administered for at least one day, one week, one month, one year, or longer (e.g., for 1-5 years or for the life of the subject).

In some embodiments, the pharmaceutical composition is administered subcutaneously. For example, from about 10 mg to about 100 mg (e.g., about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, e.g., about 15 mg, 45 mg, or 90 mg) may be administered to the subject subcutaneously, e.g., once or twice per week, e.g., for at least 1, 2, 3, 4, 5, 6, 7, 8, 9, 10, or more weeks.

In some embodiments, the pharmaceutical composition is administered intravenously. For example, from about 10 mg to about 100 mg (e.g., about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg, e.g., about 15 mg, 45 mg, or 90 mg) may be administered to the subject intravenously, e.g., once or twice per week, e.g., for at least 1, 2, 3, 4, 5, 6, 7, 8, 9, 10, or more weeks.

In some embodiments, the pharmaceutical composition is administered intravenously and subcutaneously. In some embodiments, the pharmaceutical composition is administered intravenously and subcutaneously at the same time. In some embodiments, the composition is administered intravenously then subcutaneously. In some embodiments, the pharmaceutical composition is administered subcutaneously then intravenously. For example, the pharmaceutical composition may be administered intravenously to the subject in one or more doses (e.g., in a single dose), e.g., as a loading dose, and subsequently administered to the subject one or more times subcutaneously, e.g., as a maintenance dose (e.g., each dose administered about once per week for a duration of the therapy).

Methods of Treatment

Provided herein are methods for treating or ameliorating at least one symptom of a subject with a bone mineralization disorder, such as HPP. Other diseases or disorders, such as bone fracture, osteoporosis, sclerosteosis, chondrocalcinosis, hypotonia, Duchenne's muscular dystrophy, tracheobronchomalacia, seizure, neurofibromatosis 1 (NF-1), and craniosynostosis may also be treated by the compositions and methods described herein. The subject may have muscle weakness. The subject may have a muscle weakness disease, such as calcium pyrophosphate deposition (CPPD) or familial hypophosphatemia. Such treatment may include administering an alkaline phosphatase (e.g., a pharmaceutical composition containing the alkaline phosphatase), or a polypeptide having alkaline phosphatase activity, to decrease the elevated PPi concentration in such subject. For example, a soluble alkaline phosphatase (sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) may be administered to neonates, infants, children, adolescents, or adults.

Subjects may be diagnosed with a bone mineralization disorder (e.g., HPP) prior to administration of an alkaline phosphatase or a polypeptide having alkaline phosphatase activity (e.g., a sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)). Additionally, a subject having or being prone to a bone mineralization disorder, such as HPP, can be a naïve subject that has not been previously treated with a sALP (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)).

One or more symptoms of the disease may first manifest in the subject as a neonate, infant, or child. In other embodiments, one or more symptoms of the disease may first manifest in the subject as an adult. In some embodiments, no detectable symptoms of the disease develop in the subject prior to adulthood. In some embodiments, detectable symptoms of the disease develop in the subject prior to adulthood, but the disease state remains undiagnosed until adulthood.

The method includes administering an alkaline phosphatase or a polypeptide having alkaline phosphatase activity (e.g., a sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) to a subject having or being prone to a bone mineralization disorder, such as HPP, in a single dose or in multiple dosages over a period of time. In particular, a sALP, such as a polypeptide having the sequence of SEQ ID NO: 5, can be administered to a subject previously determined to have elevated inorganic pyrophosphate (PPi) concentration or at least one predetermined biomarker/score for an HPP symptom (e.g., muscle weakness), such as an average BOT-2 strength score of less than 10, an average BOT-2 running speed and agility score of less than 5, an average CHAQ index score greater than about 0.8, and/or an average PODCI score of less than about 40, an average 6MVVT of less than about 80% of the predicted 6MVVT value, a Muscle Strength Grade of less than 5, and/or an average HHD value (e.g., an average HHD muscle or grip strength value) of, e.g., less than about 80% of the predicted HHD value. For example, a sALP can be administered to a subject previously determined to have a concentration of PPi in a sample (e.g., a plasma sample) of greater than about 5.71 µM for an infant or child (e.g., a subject of about 12 years of age or less); greater than about 4.78 µM for an adolescent (e.g., a subject of about 13 to about 18 years of age); or greater than about 5.82 µM for an adult (e.g., a subject of greater than about 18 years of age). In other embodiments, the bone mineralization disorder, such as HPP, described herein is caused by an elevated concentration of at least one alkaline phosphatase substrate (e.g., PPi, PLP, PEA, etc.). Alternatively, an alkaline phosphatase, or a polypeptide having alkaline phosphatase activity, (e.g., a sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be administered to a subject having or being prone to a bone mineralization disorder, such as HPP, prior to determination of muscle weakness score (e.g., using the BOT-2 strength score, BOT-2 running speed and agility score, the CHAQ index score, the BSID-III scaled score, the PDMS-2 standard score, a Muscle Strength score, a 6MVVT value, and/or a HHD value). Treatment with an ALP according to the methods described herein promotes, e.g., an increase in activities of ADL, a decrease in pain, and/or an improvement in motor development.

Additionally, each of the described scores (e.g., the BOT-2 strength score, BOT-2 running speed and agility score, the CHAQ index score, the BSID-III scaled score, the PDMS-2 standard score, 6MWT, the 12-POMA-G, a modified performance-oriented mobility assessment (mPOMA-G, such as the one illustrated in Phillips et al. 2015 Bone Abstracts 4:P136), or the HHD value) of a subject having or being prone to a bone mineralization disorder, such as HPP, described herein can be used singly or in any combination to assess treatment efficacy using a sALP (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)), in which improvements relative to a certain test score demonstrate that the sALP is effective for treating the bone mineralization disorder, such as HPP.

For example, when administration of an alkaline phosphatase or a polypeptide having alkaline phosphatase activity (e.g., a sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) to a subject having or being prone to a bone mineralization disorder, such as HPP, results in an average increase in the BOT-2 strength score to about 10 or greater than about 10, in which the subject previously had an average BOT-2 strength score of less than about 10, then the alkaline phosphatase or a polypeptide having alkaline phosphatase activity treatment is effective at treating, e.g., physical impairments associated with a bone mineralization disorder, such as HPP. Alternatively, when administration of a sALP does not result in an average increase in the BOT-2 strength score to about 10 or greater than about 10, the dosage and/or frequency of alkaline phosphatase or a polypeptide having alkaline phosphatase activity administration can be changed (e.g., increased, for example, for an indefinite term or a short term (e.g., 1-6 months or up to one year or more) in order to determine the effective amount of the alkaline phosphatase or a polypeptide having alkaline phosphatase activity for the subject. For instance, the dosage of the sALP (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be increased from, e.g., from about 0.1-1 mg/kg/week to about 1-2 m/kg/week, from about 0.5-3 mg/kg/week to about 3-6 mg/kg/week or from about 3-6 mg/kg/week to about 6-9 mg/kg/week. Similarly, the frequency of dosage can be increased, e.g., from about once every three weeks to about once every two weeks or from about once every two weeks to about once every week. Alternatively, if improvement in one of the metrics described herein is achieved, the dosage and/or frequency of administration can remain the same or decrease from, e.g., about 6-9 mg/kg/week to about 3-6 mg/kg/week, from about 3-6 mg/kg/week to about 0.5-3 mg/kg/week, or from about 0.5-3 mg/kg/week to about 0.1-1 mg/kg/week. Similarly, the frequency of dosage administration can decrease from about once every week to about once every two weeks or from about once every two weeks to about once every three weeks.

Additionally, when administration of an alkaline phosphatase or a polypeptide having alkaline phosphatase activity (e.g., a sALP, e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) to a subject having or being prone to a bone mineralization disorder, such as HPP, results in an improvement in the Muscle Strength Grade categorization of the subject of one or more (e.g., an improvement to a Muscle Strength Grade of 1, 2, 3, 4, or 5 from a prior, lower Muscle Strength Grade), in which the subject previously had an average Muscle Strength Grade of less than about 5, then the alkaline phosphatase or a polypeptide having alkaline phosphatase activity treatment is effective at treating, e.g., physical impairments associated with a bone mineralization disorder, such as HPP. Alternatively, when administration of a sALP does not result in an improvement in the Muscle Strength Grade categorization of the subject of one or more from a prior, lower Muscle Strength Grade, the dosage and/or frequency of alkaline phosphatase or a polypeptide having alkaline phosphatase activity administration can be changed (e.g., increased) in order to determine the effective amount of the alkaline phosphatase or a polypeptide having alkaline phosphatase activity for the subject. For instance, the dosage of the sALP (e.g., a polypeptide having the sequence of SEQ ID NO: 5 or a variant thereof with at least 85% sequence identity thereto (e.g., a polypeptide that includes one or more, or all, of the mutations E108M, N213Q, and N286Q relative to SEQ ID NO: 1 or 5)) can be increased from, e.g., from about 0.1-1 mg/kg/week to about 1-2 m/kg/week, from about 0.5-3 mg/kg/week to about 3-6 mg/kg/week or from about 3-6 mg/kg/week to about 6-9 mg/kg/week. Similarly, the frequency of dosage can be increased, e.g., from about once every three weeks to about once every two weeks or from about once every two weeks to about once every week. Alternatively, if improvement in one of the metrics described herein is achieved, the dosage and/or frequency of administration can remain the same or decrease from, e.g., about 6-9 mg/kg/week to about 3-6 mg/kg/week, from about 3-6 mg/kg/week to about 0.5-3 mg/kg/week, or from about 0.5-3 mg/kg/week to about 0.1-1 mg/kg/week. Similarly, the frequency of dosage administration can decrease from about once every week to about once every two weeks or from about once every two weeks to about once every three weeks.

Pharmacokinetic (PK) Parameters

In some embodiments, the treatment method produces an $AUC_{0-168h}$ of from about 50 μg×hour/mL to about 4000 μg×hour/mL in the blood of the subject. For example, the method may produce an $AUC_{0-168h}$ of from about 1000 μg×hour/mL to about 3000 μg×hour/mL in the blood of the subject. In some embodiments, the treatment method produces a $C_{max}$ of from about 0.5 μg/mL to about 25 μg/mL in the blood of the subject. For example, the treatment method may produce a $C_{max}$ of from about 0.6 μg/mL to about 20 μg/mL in the blood of the subject.

EXAMPLES

The disclosure is illustrated by the following non-limiting examples. It is to be understood that the particular examples, materials, amounts, and procedures are to be interpreted broadly in accordance with the scope and spirit of the disclosure as set forth herein.

Example 1

ALP201 is a human recombinant TNSALP-Fc-deca-aspartate fusion protein. It is a soluble glycoprotein composed of two polypeptide chains of 724 amino acids made from the catalytic domain of human TNSALP (SwissProt, P05186), the human immunoglobulin (Ig) G2/4 Fc domain (SwissProt, P01859, P01861) (to facilitate purification and extend half-life), and a deca-aspartate peptide (to target the bone).

ALP201 is an ERT for addressing the underlying cause of bone mineralization disorders, such as HPP by replacing a defective alkaline phosphatase enzyme. ALP201 shares some structural similarity to asfotase alfa, also a TNSALP-Fc-deca-aspartate fusion protein ERT, which is the only approved treatment for subjects with pediatric-onset HPP (marketed under the trade name STRENSIQ®).

ALP201 is a next-generation HPP therapy with equivalent potency and improved activity as compared to asfotase alfa. ALP201 also provides increased exposure due to a longer half-life, reduced α-phase clearance, and increased bioavailability. These improved characteristics support lower doses and longer dosing intervals for ALP201, relative to asfotase alfa. Subject experience is expected to improve by reducing injection volumes and dosing frequency, which may also translate to fewer injection site reactions.

ALP201

Physical and Chemical Characteristics

ALP201 is a soluble Fc fusion protein with a molecular weight of about 160 KDa and is composed of two polypeptide chains covalently linked by two disulfide bonds. Each polypeptide chain contains 724 amino acids and is composed of three segments:

The N-terminal region of the polypeptide, amino acids L1-A491, contains the enzyme TNSALP which is the soluble part of the human tissue non-specific alkaline phosphatase enzyme and contains the catalytic function. Within the enzymatic region of each polypeptide chain, a single point mutation (E108M) was introduced to improve enzyme activity and two N-linked glycosylation sites (N213Q and N286Q) removed for process improvements.

The second portion of the polypeptide, amino acids V492-K714, contains the Fc part of the human Immunoglobulin gamma 2/4 (IgG2/4) containing hinge, CH2 and CH3 domains.

The C-terminal region of the polypeptide, amino acids D715-D724, contains ten aspartic acids. This peptide sequence promotes the binding of ALP201 to the mineral phase of bone.

Each polypeptide chain of ALP201 contains four glycosylation sites (N123, N254, N413, and N564) and eleven cysteine (Cys) residues. Cys102 exists as a free cysteine. Each polypeptide chain contains four intra-chain disulfide bonds between Cys122 to Cys184, Cys472 to Cys480, Cys528 to Cys588, and Cys634-Cys692. The two polypeptide chains are connected by two inter-chain disulfide bonds between Cys494-Cys494 and Cys497-Cys497. In addition to these covalent structural features, mammalian alkaline phosphatases generally have four metal binding sites on each polypeptide chain, two sites for zinc, one site for magnesium and one site for calcium.

General Properties of ALP201

Table 1 lists the general properties of ALP201. The theoretical chemical formula and theoretical average molecular weight were calculated assuming that all but two cysteine residues are disulfide bonded.

TABLE 1

General Properties of ALP201

| Characteristic | Result |
| --- | --- |
| Predicted Formula | $C_{7058} H_{10928} N_{1952} O_{2198} S_{58}$ (aglycosylated) |
| Predicted Molecular Weight | 160,154.6 Da (aglycosylated) |
| Number of Amino Acids | 1448 |
| Biologic Activity | Pyrophosphatase (PPi) and pyridoxal 5'-phosphate (PLP) hydrolysis, Hydroxyapatite binding. |

Drug Product

ALP201 100 mg/mL Vial

The ALP201 Drug Product (100 mg/mL) is a sterile, preservative-free formulated liquid solution of ALP201 and excipients contained in a single use 2 mL vial. The drug product does not contain any novel excipient or excipients of animal or human origin. Each 2 mL vial nominally contains 1.2 mL (overfill) of the drug product to deliver 100 mg of ALP201/vial. The drug product is filled into a 2 mL Type I clear glass vial with a 13 mm chlorobutyl stopper with aluminum seal. The quantitative composition of the ALP201 Drug Product is presented in Table 2.

TABLE 2

Composition of ALP201 Drug Product for Subcutaneous or Intravenous Administration

| Ingredient | Quantity per Vial | Function | Standard |
| --- | --- | --- | --- |
| ALP201 | 100 mg/mL | Active ingredient | In-house standard |

TABLE 2-continued

Composition of ALP201 Drug Product for Subcutaneous or Intravenous Administration

| Ingredient | Quantity per Vial | Function | Standard |
|---|---|---|---|
| Sodium phosphate monobasic monohydrate | 0.4 mg/mL | Buffering Agent | Multi-compendial |
| Sodium phosphate dibasic heptahydrate | 1.9 mg/mL | Buffering Agent | Multi-compendial |
| L-proline | 16.1 mg/mL | Stabilizer | Multi-compendial |
| Sucrose | 47.9 mg/mL | Tonicity modifier/ stabilizer | Multi-compendial |
| Polysorbate 80 | 0.5 mg/mL | Adsorption Inhibitor | Multi-compendial |
| Water for Injection | Q.S. | Aqueous vehicle | Multi-compendial |

Abbreviations:
QS = quantity sufficient.

In Vivo Studies

ALP201 was evaluated using in vivo studies to characterize its pharmacology, PK/toxicokinetics (TK), local tolerability, and potential systemic toxicity. The pharmacology studies conducted include repeat dose studies in HPP mouse (Akp2GW (−/−) mouse), to identify the ALP201 minimal efficacious dose. To understand the PK properties of ALP201, single dose PK studies were conducted in mice, rat, and monkeys. The toxicology studies evaluated the systemic toxicity of the administration of SC ALP201 in rat and monkeys; these studies included safety pharmacology endpoints (cardiovascular, respiratory in monkey study and neurofunctional in rat study), TK evaluations, and a recovery period to assess the reversibility of any treatment-related effects.

A summary of the in vivo studies conducted with ALP201 that support its use in humans is provided in Table 3.

TABLE 3

Overview of ALP201 In Vivo Studies

| Study | Test System/ Number of animals | Method of Administration and Dose (mg/kg) | Study Number | Results |
|---|---|---|---|---|
| Pharmacology Studies | | | | |
| 36-Day Multi-Dose Efficacy Study of ALP201 and Asfotase Alfa in HPP Mice | Akp2GW(−/−) Mice | SC: 4.8 mg/kg on qd, q2d, and q1w dosing intervals SC: 4.8 mg/kg (days 1-24), 1.5 mg/kg (days 25-35) | HPP-PoC-01 | ALP201 demonstrated efficacy in bone mineralization index and survival endpoints at lower doses and longer dosing intervals than those used for asfotase alfa efficacious dose. |
| ALP201 Dose Titration to Determine Mineralization ED85 in Akp2GW −/− Mice | Akp2GW(−/−) Mice | SC: 0.15, 0.3, 0.8, or 2.0 mg/kg/dose (q2d dosing) | HPP-MED-01 | ALP201 demonstrated efficacy in bone mineralization index, bone alkaline phosphatase activity, survival, and end of study plasma level endpoints at much lower doses than those used in HPP-PoC-01. Dose response for bone mineralization index observed for ALP201 across doses, with 2.0 mg/kg q2d dose performing slightly better than asfotase alfa at 2.5 mg/kg qd. |
| Pharmacokinetics Studies | | | | |
| Assessment of Single Dose Pharmacokinetics of ALP201 Following IV and SC Administration in Male C57BL/6 Mice | C57BL/6 Mice | IV and SC: 4 mg/kg | HPP-PK-01 | Terminal half-life after IV administration measured 48 hours. Absolute bioavailability following SC administration was high at 96%. PK parameters, including systemic exposure of ALP201 by AUC, was significantly improved relative to asfotase alfa. |
| An Assessment of Pharmacokinetics of ALP201 Following IV and SC Administration in Rats | Sprague-Dawley Rats 2M/2F per cohort | IV bolus: 1, 3, 9, or 27 mg/kg SC: 2 or 27 mg/kg | 20205897 | Following IV or SC administration, the ALP201 PK as measured by enzyme activity was slightly less than proportional over the studied dose range (1 to 27 mg/kg). Terminal half-life averaged about 2 days. Absolute bioavailability following SC administration was 61% and 54% for the 2 and 27 mg/kg dose, respectively. Single dose of ALP201 administered IV or SC (from 1 to 27 mg/kg) was well tolerated in male and female rats. |
| An Assessment of the Pharmacokinetics of ALP201 Following IV and SC Administration in NHP | Cynomolgus Monkeys 3M per cohort | IV bolus: 2, 6, or 20 mg/kg SC: 2 or 20 mg/kg | 20205899 | Following IV or SC administration, the ALP201 PK as measured by enzyme activity was close to dose-proportional over the studied dose range (2 to 20 mg/kg). Terminal elimination half-life averaged about 3 days. Absolute bioavailability following SC administration was 69.6% and 86.9% for the 2 and 20 mg/kg dose, respectively Single dose of ALP201 administered IV or SC (from 2 to 20 mg/kg) was well tolerated in male nonhuman primates. |

TABLE 3-continued

Overview of ALP201 In Vivo Studies

| Study | | Test System/ Number of animals | Method of Administration and Dose (mg/kg) | | Study Number | Results |
|---|---|---|---|---|---|---|
| Nonclinical Safety Studies (Toxicology and Safety-Pharmacology) | | | | | | |
| ALP201: A 28-Day Toxicity Study in Rats with a 28-Day Recovery Period | GLP | Sprague-Dawley Rats | Repeat-dose SC: 0, 2, 10, or 30 mg/kg/dose (q3d; 10 doses total) Single-Dose IV: 0 or 10 mg/kg/dose (to evaluate SC absolute bioavailability) | Charles River Laboratories | 1727-227 | No noteworthy systemic organ toxicity or local tolerability findings were observed at any of the doses evaluated in the study. No noteworthy neurotoxicity findings were observed at any of the doses evaluated in the study. Immunogenicity: (positive ADA) responses were observed at all of the doses evaluated in the study. The high dose of 30 mg/kg/dose evaluated in the study is the NOAEL |
| ALP201: A 28-Day Toxicity Study by Subcutaneous Injection in Cynomolgus Monkeys with a 28-Day Recovery Period | GLP | Cynomolgus Monkeys | Repeat-dose SC: 0, 1, 5, or 20 mg/kg/dose (q3d; 10 doses total) | Charles River Laboratories | 1727-228 | No noteworthy systemic organ toxicity or local tolerability findings were observed at any of the doses evaluated in the study. No noteworthy cardiovascular or respiratory findings were observed at any of the doses evaluated in the study. Immunogenicity: (positive ADA) responses were observed at all of the doses evaluated in the study. The high dose of 20 mg/kg/dose evaluated in the study is the NOAEL |

Abbreviations:
F = female;
GLP = Good Laboratory Practice;
IV = intravenous;
M = male;
NOAEL = no observed adverse effect level;
qd = once a day;
q1w = once a week;
q2d = every other day;
SC = subcutaneous;
TBD = to be determined.

In Vitro Pharmacology

Pyrophosphate (PPi) is a critical natural substrate of TNSALP, and low TNSALP levels in HPP subjects result in elevated circulating PPi blood levels. Elevated pyrophosphate levels prevent proper bone mineralization and lead to abnormal bone manifestations observed in subjects with HPP. Therefore, PPi was viewed as a natural substrate to target with higher enzyme activity levels in an engineered second-generation asfotase alfa molecule.

Substrate saturation curves for pyrophosphate hydrolysis by ALP201 and asfotase alfa are shown in FIG. 1. ALP201 retains a similar Km value (47 mM) for pyrophosphate as asfotase alfa (53 mM), but ALP201 operates with a significantly higher turnover number (kcat=11,619 $min^{-1}$ for ALP201 vs 6,714 $min^{-1}$ for asfotase alfa). Similar Km values for ALP201 and the wildtype TNSALP catalytic domain in asfotase alfa suggest that ALP201 should not be more likely than asfotase alfa to dangerously lower circulating PPi levels when present at equivalent serum alkaline phosphatase activity levels.

Pyridoxyl-5'-phosphate is a second natural substrate of TNSALP with clinical relevance to HPP. TNSALP cleaves PLP to form pyridoxal, the B6 vitamer that is most easily taken in by tissues. When serum alkaline phosphatase levels are very low, systemic Vitamin B6 metabolism can be impaired. In HPP, PLP deficiency in the brain manifests as seizures, and systemic deficiencies in PLP hydrolysis by TNSALP may play a role in the pain, muscle weakness, and hypotonia experienced by some HPP subjects. Therefore, ERT for the treatment of HPP can be used to provide sufficient PLP hydrolysis activity.

Substrate saturation curves for PLP hydrolysis by ALP201 and asfotase alfa are shown in FIG. 2. ALP201 has a slightly weaker Km value (2.76 mM) for PLP compared to asfotase alfa (1.71 mM), but ALP201 operates with a significantly higher turnover number (kcat=3,324 $min^{-1}$ for ALP201 vs 2,623 $min^{-1}$ for asfotase alfa), resulting in very similar PLP activity saturation curves for the two molecules. Substrate kinetic parameters are tabulated in Table 4.

TABLE 4

Kinetic parameters for substrate hydrolysis by ALP201 and asfotase alfa

| Substrate | Construct | Km (µM) | Kcat ($min^{-1}$) |
|---|---|---|---|
| PPi | ALP201 | 46.8 +/− 5.7 | 11,619 +/− 449 |
| | asfotase alfa (Strensiq) STRENSIQ ® | 53.2 +/− 5.5 | 6,714 +/− 226 |
| PLP | ALP201 | 2.76 +/− 0.3 | 3,324 +/− 97 |
| | asfotase alfa (Strensiq) STRENSIQ ® | 1.71 +/− 0.2 | 2,623 +/− 75 |

Abbreviations:
PPi = pyrophosphate;
PLP = Pyridoxyl-5'-phosphate;
Km = Michaelis-Menten Constant;
µM = micromolar;
Kcat = catalytic constant for turnover rate;
min = minute.

In Vivo Pharmacology

Preclinical efficacy studies on ALP201 were performed using the Akp2GW (−/−) mouse, which is an animal model of human HPP. The Akp2GW (−/−) mice share the same HPP-inducing TNSALP mutation used in the Akp2 (−/−)

mice that were previously used in the preclinical evaluation of asfotase alfa. Natural history studies performed at Alexion during the development of the Akp2GW (−/−) mice showed that homozygotic TNSALP activity knockout Akp2GW (−/−) mice displayed a nearly identical bone mineralization and survival phenotype as Akp2 (−/−) mice (Akp2GW-NH-01-02).

In efficacy studies used to evaluate the efficacy of ALP201 using the Akp2GW (−/−) mouse model, doses of test articles were given subcutaneously, beginning on Day 1 after birth until Day 35. Outcomes reported in all studies included overall survival, body weight growth rate, bone mineralization of hind paw bones on Day 36 (or at death if before end-of-study [EOS]), and EOS trough plasma enzyme activity levels (taken on Day 36 in every day [qd] and every week [q1w] groups, and on Day 37 in every 2 days [q2d] dose groups). In some studies, EOS femur and tibia lengths and mouse femur alkaline phosphatase activity were determined.

In previous studies using Akp2 (−/−) mice, asfotase alfa demonstrated efficacy in both bone mineralization and overall survival study endpoints at a dose of 7-10 mg/kg/day for active preparations of asfotase alfa, depending upon the specific activity of the test article. The estimated minimum efficacious dose (MED) of asfotase alfa was defined as the dose that resulted in 85% of measurable mice in a group obtaining normal bone mineralization score by the end of the study or at death, if death occurred prior to the end of the study. An analysis of efficacy data placed this value at roughly 2.0-2.5 mg/kg/day, depending upon the specific activity of the test article.

The efficacy of ALP201 in a murine model of HPP was tested in 2 multi-dose studies at varying SC doses and dosing intervals in Akp2GW (−/−) mice. In these studies, efficacy of ALP201 was compared to efficacy observed in a positive control group dosed with daily SC administration of asfotase alfa.

In a previous study, asfotase alfa was dosed by SC administration at its fully efficacious dose of 9.8 mg/kg/day on a qd dosing schedule. An equivalent 4-MUP activity dose of ALP201 was dosed by SC administration in PBS on qd, q2d, and q1w dosing intervals. In one dose group, the dose of ALP201 was reduced by one-half log after weaning of the mice at Day 25. Subcutaneous administration of PBS on a qd schedule was used as a negative control. Tabulation of these dosing groups can be found in Table 5.

In the HPP-MED-01 study, asfotase alfa was dosed by SC administration at its minimum efficacious dose of 2.5 mg/kg/day on a qd dosing schedule. ALP201 was administered subcutaneously in PBS on a q2d dosing schedule at doses of 2.0, 0.8, 0.3, and 0.15 mg/kg. Subcutaneous administration of PBS on a q2d schedule was used as a negative control. Tabulation of these dosing groups can be found in Table 5.

TABLE 5

Dose-Grouped Study Plans for Akp2GW (−/−) Efficacy Studies

| Study | Test Article | Dose (mg/kg) | Dose (U MUP activity/kg) | Interval | Mouse Genotype |
|---|---|---|---|---|---|
| HPP-PoC-01 | ALP201 | 4.8 | 206 | qd | Akp2GW (−/−) |
| HPP-PoC-01 | ALP201 | 4.8 (days 1-24) 1.5 (days 25-35) | 206 (days 1-24) 62 (days 25-35) | qd | Akp2GW (−/−) |
| HPP-PoC-01 | ALP201 | 4.8 | 206 | q2d | Akp2GW (−/−) |
| HPP-PoC-01 | ALP201 | 4.8 | 206 | q1w | Akp2GW (−/−) |
| HPP-PoC-01 | asfotase alfa | 9.8 | 206 | qd | Akp2GW (−/−) |
| HPP-PoC-01 | PBS | NA | NA | qd | Akp2GW (−/−) |
| HPP-PoC-01 | PBS | NA | NA | qd | Akp2GW (+/+) |
| HPP-MED-01 | ALP201 | 2 | 78 | q2d | Akp2GW (−/−) |
| HPP-MED-01 | ALP201 | 0.8 | 31 | q2d | Akp2GW (−/−) |
| HPP-MED-01 | ALP201 | 0.3 | 11.6 | q2d | Akp2GW (−/−) |
| HPP-MED-01 | ALP201 | 0.15 | 5.8 | q2d | Akp2GW (−/−) |
| HPP-MED-01 | asfotase alfa | 2.5 | 54 | qd | Akp2GW (−/−) |
| HPP-MED-01 | PBS | NA | NA | q2d | Akp2GW (−/−) |
| HPP-MED-01 | PBS | NA | NA | q2d | Akp2GW (+/+) |

Abbreviations:
PBS = phosphate buffer saline;
q1w = once weekly;
q2d = every 2 days;
qd = once daily;
U MUP = Units of activity in 4-methylumbelliferyl phosphate hydrolysis;
NA = not applicable.

Bone Mineralization Outcomes

Day 36/37 bone mineralization outcomes were determined by X-ray analysis of the hind paws of treated Akp2GW (−/−) mice. X-ray visualization of hind paw bone mineralization was compared to Day 36 benchmark X-ray images exemplifying 4 classification categories: Unaffected, Slight Deficit, Moderate Deficit, and Severe Deficit. Detailed description of these classifications can be found in Table 6. Blinded individuals assigned a score to images for each mouse, and once complete, scores were compiled within individual dose groups.

TABLE 6

Classification for Day 36 Hind Paw Bone Mineralization Index Scoring

| Score | Classification of Bone Mineralization Deficit | Description of Severity - Faxitron 2D X-Ray | Description of Severity - CT 3D X-Ray |
|---|---|---|---|
| 1 | Severe | Profound dysmorphology and complete absence of medial and distal phalanges of the digits and complete lack of secondary ossification centers | Profound dysmorphology and complete absence of either proximal and/or medial and distal phalanges of the digits and complete lack of secondary ossification centers with variable metatarsal formation |

TABLE 6-continued

Classification for Day 36 Hind Paw Bone Mineralization Index Scoring

| Score | Classification of Bone Mineralization Deficit | Description of Severity - Faxitron 2D X-Ray | Description of Severity - CT 3D X-Ray |
|---|---|---|---|
| 2 | Moderate | Fully formed digits, but still no apparent secondary ossification centers | Fully formed digits with either no apparent secondary ossification centers or variable emerging secondary center(s), variable sesamoids, and variable metatarsal formation |
| 3 | Slight | Fully formed digits with variable but incomplete secondary ossification centers | Fully formed digits with either missing secondary ossification center(s) or center(s) with variable development, misshapen and missing sesamoid(s) with variable metatarsal formation |
| 4 | Unaffected | Fully formed digits and all secondary ossification centers present | Fully formed digits with all secondary ossification centers present, all sesamoids present with variable morphology and fully formed metatarsals. |

The distribution of observed EOS hind paw bone mineralization index scores for each dosing group can be found in Table 7.

TABLE 7

End of Study Bone Mineralization Index Distribution of Hind Paw Bones in Treated Akp2GW (−/−) Mice Groups

| Dose Group | # in Group | # Unaffected (Score = 4) | # Slight Deficit (Score = 3) | # Moderate Deficit (Score = 2) | # Severe Deficit (Score = 1) |
|---|---|---|---|---|---|
| WT PBS | 20 | 20 (100%) | 0 | 0 | 0 |
| ALP201 4.8 qd | 25 | 25 (100%) | 0 | 0 | 0 |
| ALP201 4.8/1.5 qd | 17 | 17 (100%) | 0 | 0 | 0 |
| ALP201 4.8 q2d | 24 | 24 (100%) | 0 | 0 | 0 |
| ALP201 2.0 q2d | 31 | 29 (93.5%) | 2 (6.5%) | 0 | 0 |
| ALP201 0.8 q2d | 29 | 18 (62.1%) | 11 (37.9%) | 0 | 0 |
| ALP201 0.3 q2d | 31 | 18 (58.1%) | 10 (32.3%) | 1 (3.2%) | 2 (6.5%) |
| ALP201 0.15 q2d | 29 | 14 (48.3%) | 9 (31.0%) | 6 (20.7%) | 0 |
| ALP201 4.8 q1w | 19 | 14 (73.7%) | 2 (10.5%) | 3 (15.8%) | 0 |
| asfotase alfa 9.8 qd | 16 | 16 (100%) | 0 | 0 | 0 |
| asfotase alfa 2.5 qd | 26 | 22 (84.6%) | 4 (15.4%) | 0 | 0 |
| HOM PBS (at death) | 50 | 7 (14.0%) | 12 (24.0%) | 24 (48.0%) | 7 (14.0%) |

Abbreviations:
HOM = homozygous knockout;
PBS = phosphate buffered saline;
qd = every day;
q2d = every 2 days;
q1w = once weekly;
WT = wildtype.

Treatment of Akp2GW (−/−) mice with ALP201 showed a dose response of increasing percentage of mice with unaffected hind paw bone mineralization with increasing ALP201 dose on the Q2D dosing interval. All ALP201 dose groups demonstrated statistically significant improvement relative to PBS-treated Akp2GW (−/−) controls (p<0.001 by one-way ANOVA analysis). These data were used to inform model-based analyses and predicted human dose projections.

End-of-Study Trough Plasma Active Enzyme Concentration Outcomes

Figure 3:
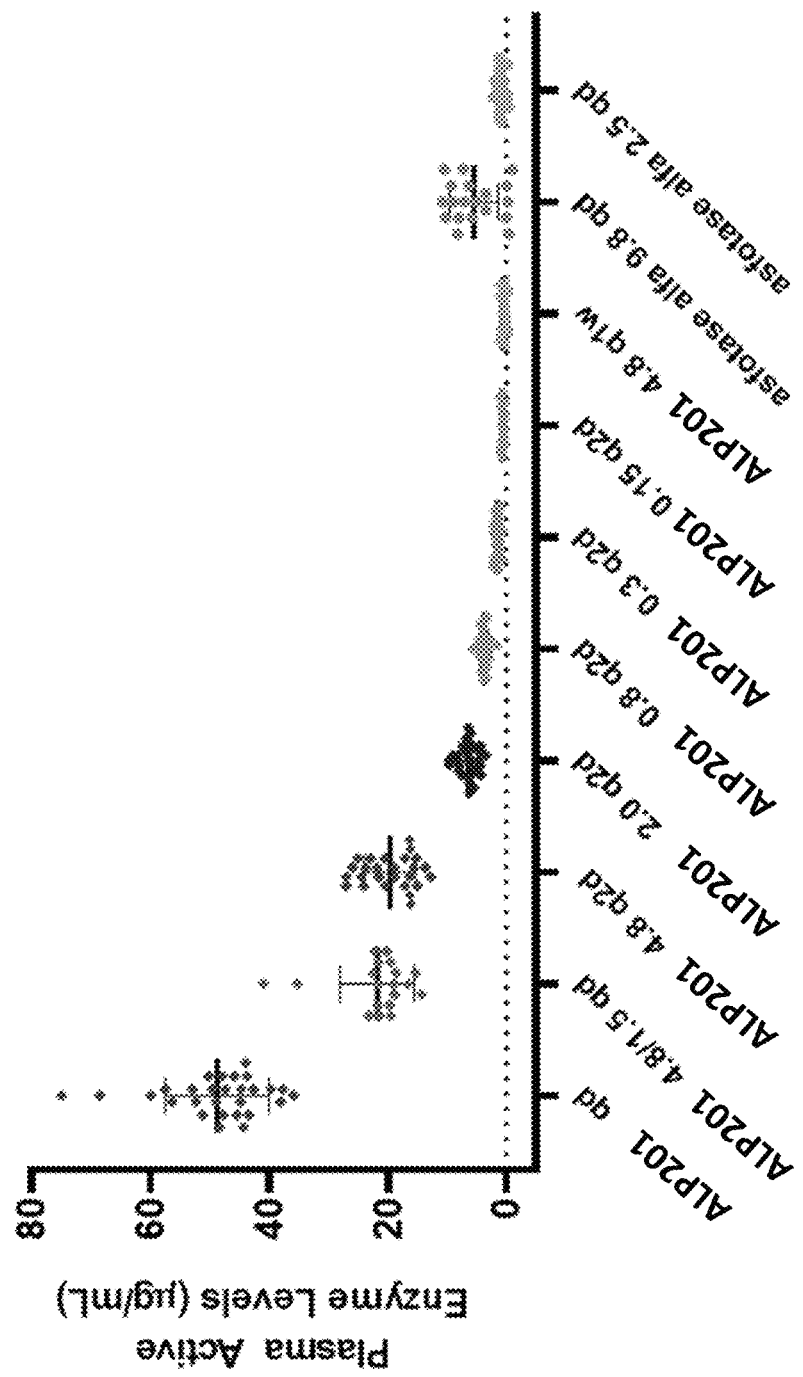
FIG. 3 is a graph showing active alkaline phosphatase enzyme concentrations in Akp2GW (−/−) mouse plasma at study end by dosing group. Abbreviations: q1w=once weekly; q2d=every 2 days; qd=every day.

Trough plasma active TNSALP enzyme concentrations were determined by measurement of TNSALP activity levels in Day 36/37 plasma samples. Measured TNSALP activity was fit to a standard curve of known enzyme activity and concentration to quantify active enzyme levels per unit volume of plasma. The distribution of EOS trough plasma active enzyme concentration is shown in FIG. 3. A tabulation of the mean EOS trough plasma active enzyme concentration by dose group is summarized in Table 8.

TABLE 8

Dose Grouped Mean End-of-Study Trough Plasma Active Enzyme Concentrations and Enzyme Activity Levels

| Study | Test Article | Dose (mg/kg) | Interval | Number of Doses in Study | Mean EOS Trough Plasma Activity Level (Units 4-MUP Hydrolysis/L) | Mean EOS Enzyme Concentration (μg/mL) | Day Collected |
|---|---|---|---|---|---|---|---|
| HPP-POC-01 | ALP201 | 4.8 | qd | 35 | 1805.2 ± 321.9 | 42.0[a] | 36 |
| HPP-POC-01 | ALP201 | 4.8/1.5 | qd | 35 | 805.8 ± 235.0 | 18.7[a] | 36 |
| HPP-POC-01 | ALP201 | 4.8 | q2d | 18 | 728.1 ± 162.4 | 16.9[a] | 37 |
| HPP-MED-01 | ALP201 | 2 | q2d | 18 | 235.4 ± 58.7 | 6.1[c] | 37 |
| HPP-MED-01 | ALP201 | 0.8 | q2d | 18 | 134.9 ± 27.6 | 3.5[c] | 37 |
| HPP-MED-01 | ALP201 | 0.3 | q2d | 18 | 54.5 ± 14.9 | 1.4[c] | 37 |
| HPP-MED-01 | ALP201 | 0.15 | q2d | 18 | 22.6 ± 9.4 | 0.6[c] | 37 |
| HPP-POC-01 | ALP201 | 4.8 | qw | 5 | 21.2 ± 13.7 | 0.5[a] | 36 |
| HPP-POC-01 | asfotase alfa | 9.8 | qd | 35 | 129.5 ± 81.9 | 6.2[b] | 36 |
| HPP-MED-01 | asfotase alfa | 2.5 | qd | 35 | 20.2 ± 13.9 | 0.9[d] | 36 |
| HPP-MED-01- | PBS - WT | NA | NA | NA | 1.7 ± 2.9 | NA | 36 |

Note:
Calculation of mean end-of-study enzyme concentration in (μg/mL) = Mean EOS Trough Plasma activity level (Units 4-MUP hydrolysis/L)/specific activity of protein (U/mg).
[a]Specific activity of ALP201 used in study = 43 U/mg
[b]Specific activity of asfotase alfa used in study = 21 U/mg
[c]Specific activity in ALP201 used in study = 38.8 U/mg
[d]Specific activity of asfotase alfa used in study = 21.5 U/mg
Abbreviations:
EOS = end-of-study;
4-MUP = 4-methylumbelliferyl phosphate;
NA = not applicable;
PBS = phosphate buffered saline;
qw = once weekly;
q2d = every 2 days;
qd = every day;
WT = wildtype.

Analysis of the EOS trough plasma active enzyme and corresponding enzyme activity levels in treated Akp2GW (−/−) mice after multiple doses clearly shows greater absolute accumulation and dose-normalized accumulation of ALP201 when compared to asfotase alfa, presumably owing to the superior PK profile of ALP201 following SC administration.

Day 36/37 Treated Akp2GW (−/−) Mouse End of Study Bone Enzyme Activity Levels

Figure 4:
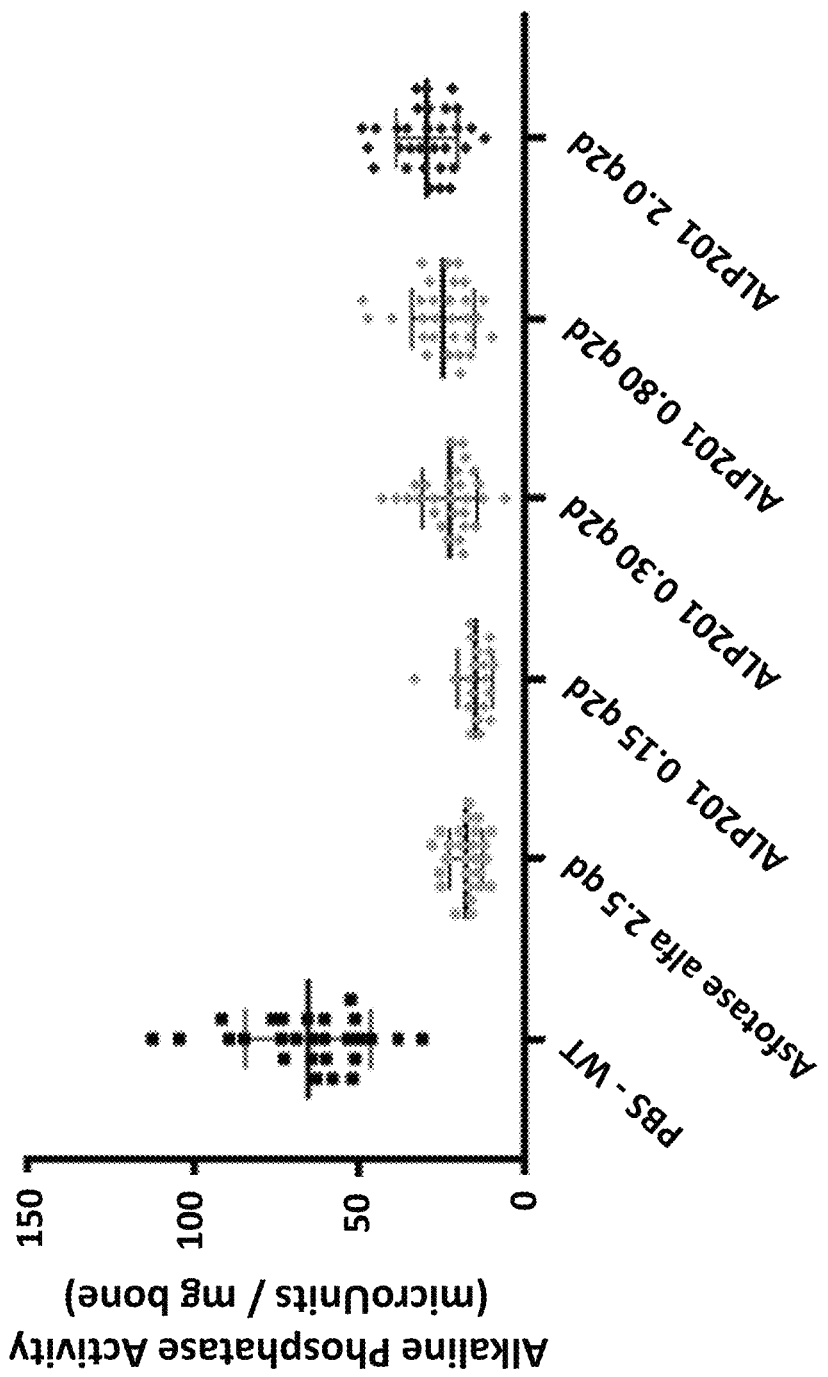
FIG. 4 is a graph showing Day 36/37 end-of-study mouse femur tissue alkaline phosphatase activity levels. Abbreviations: q2d=every 2 days; qd=every day.

Alkaline phosphatase activity levels in treated Akp2GW (−/−) mouse femur tissue was determined in an ex vivo assay at the end of the HPP-MED-01 study, using 4-MUP as a substrate. In this assay, only the mineralized portion of the femur was assayed for activity to avoid potential contamination with blood or highly perfused tissue that might still hold high levels of ALP201 or asfotase alfa. The distribution of enzyme activity levels attached to treated Akp2GW (−/−) mouse femurs is shown in FIG. 4, with data displayed in microunits of 4-MUP hydrolysis activity/mg of mineralized femur tissue.

TABLE 9

Dose Grouped Mean End-of-Study Femur Active Enzyme Concentrations

| Study | Test Article | Dose (mg/kg) | Interval | Number of Doses in Study | Mean EOS Femur Activity Level ± SD (microUnits 4-MUP hydrolysis/mg bone) | Day Collected |
|---|---|---|---|---|---|---|
| HPP-MED-01 | ALP201 | 2 | q2d | 18 | 26.5 ± 9.4 | 37 |
| HPP-MED-01 | ALP201 | 0.8 | q2d | 18 | 20.8 ± 6.6 | 37 |
| HPP-MED-01 | ALP201 | 0.3 | q2d | 18 | 18.6 ± 6.5 | 37 |
| HPP-MED-01 | ALP201 | 0.15 | q2d | 18 | 13.0 ± 5.9 | 37 |

TABLE 9-continued

Dose Grouped Mean End-of-Study Femur Active Enzyme Concentrations

| Study | Test Article | Dose (mg/kg) | Interval | Number of Doses in Study | Mean EOS Femur Activity Level ± SD (microUnits 4-MUP hydrolysis/mg bone) | Day Collected |
|---|---|---|---|---|---|---|
| HPP-MED-01 | asfotase alfa | 2.5 | qd | 35 | 14.8 ± 5.3 | 36 |
| HPP-MED-01 | PBS - WT | NA | NA | NA | 60.6 ± 19.6 | 37 |

Abbreviations:
4-MUP = 4-methylumbelliferyl phosphate;
PBS = phosphate buffered saline;
q1w = once weekly;
q2d = every 2 days;
qd = every day;
WT = wildtype;
mg = milligram;
SD = standard deviation;
NA = not applicable Bone activity data showed a dose response with increasing EOS bone tissue activity levels with increasing ALP201 dose. At study end, mice in the ALP201 0.15 mg/kg q2d group had 22.6% of wildtype alkaline phosphatase activity restored, compared to 26.9% for the asfotase alfa 2.5 mg/kg qd group. ALP201 doses of 0.3, 0.8, and 2.0 mg/kg q2d restored 34.4%, 37.6%, and 44.9% of wildtype activity, respectively. End-of-study bone activity level differences between ALP201 doses at 0.8 and 2.0 mg/kg q2d were statistically significant from the asfotase alfa 2.5 mg/kg q2d group when analyzed with a one-way ANOVA with adjusted p values of 0.0048 and <0.0001, respectively.

Treated Akp2GW (−/−) Mouse Survival Outcomes

Figure 5:
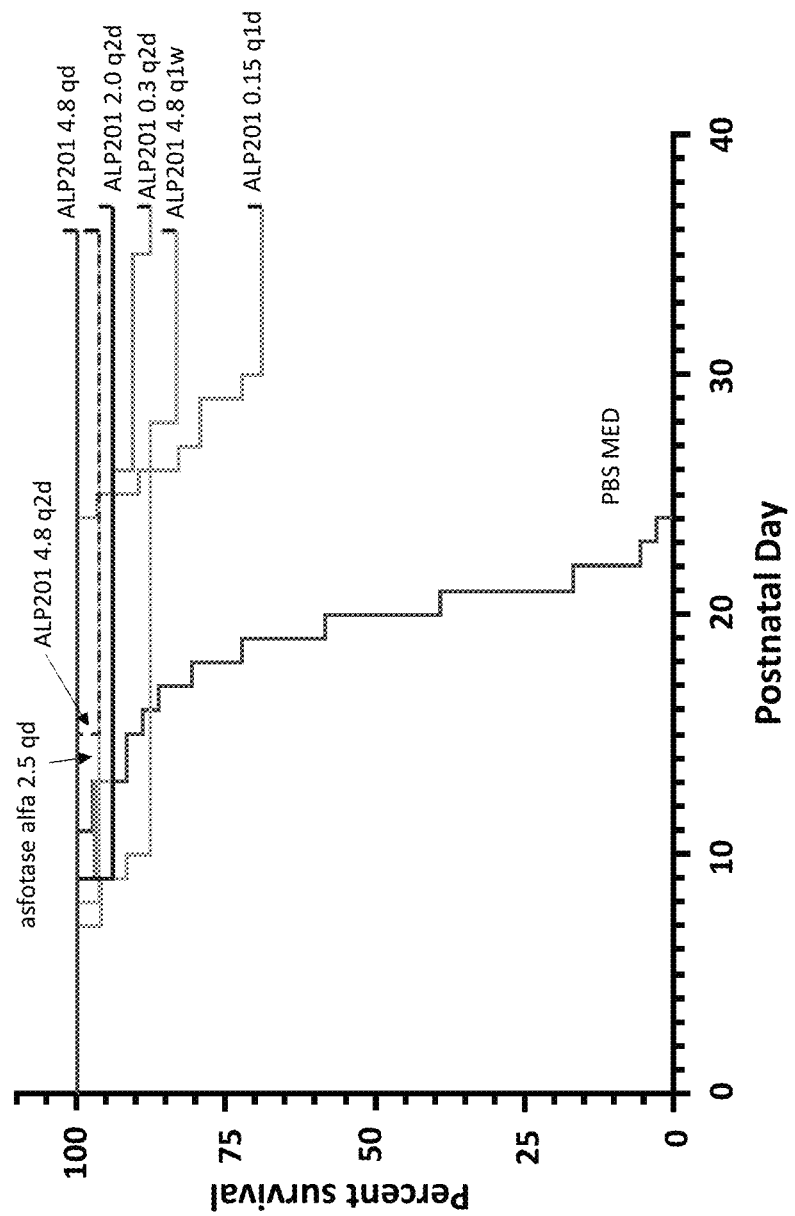
FIG. 5 is a set of representative survival curves for Akp2GW (−/−) mice treated with ALP201 and asfotase alfa in 36-day efficacy studies. Abbreviations: MED=minimum efficacious dose; PBS=phosphate buffered saline; q1w=once weekly; q2d=every 2 days; qd=every day.

All PBS-treated Akp2GW (−/−) died on or before Day 26 of the studies, with a median survival time of 20 days. ALP201 treatment of Akp2GW (−/−) mice significantly improved 36-day survival rates in all dose groups relative to the PBS vehicle control (FIG. 5 and Table 10). All ALP201 dosing groups reached EOS survival rates of at least 69%, with all qd and q2d interval dose groups above a dose of 0.15 mg/kg/day posting 88% or greater overall survival rates. Survival curves for ALP201 4.8 mg/kg q1w group and asfotase alfa 9.8 mg/kg qd group have highly similar outcomes.

TABLE 10

Survival Percentage Summary of Akp2GW (−/−) Mouse Groups Treated in 36-Day Efficacy Studies

| Study | Test Article | Dose (mg/kg) | Interval | End of Study Survival (%) |
|---|---|---|---|---|
| HPP-PoC-01 | ALP201 | 4.8 | qd | 100 |
| HPP-PoC-01 | ALP201 | 4.8/1.5 | qd | 100 |
| HPP-PoC-01 | ALP201 | 4.8 | q2d | 96 |
| HPP-MED-01 | ALP201 | 2 | q2d | 94 |
| HPP-MED-01 | ALP201 | 0.8 | q2d | 97 |
| HPP-MED-01 | ALP201 | 0.3 | q2d | 88 |
| HPP-MED-01 | ALP201 | 0.15 | q2d | 69 |
| HPP-PoC-01 | ALP201 | 4.8 | q1w | 83 |
| HPP-PoC-01 | asfotase alfa | 9.8 | qd | 81 |
| HPP-MED-01 | asfotase alfa | 2.5 | qd | 96 |
| HPP-PoC-01 | PBS | NA | NA | 0 |
| HPP-MED-01 | PBS | NA | NA | 0 |

Abbreviation:
MED = minimum efficacious dose;
PBS = phosphate buffered saline;
PoC = proof of concept;
qd = every day;
q2d = every 2 days;
q1w = once weekly;
NA = not applicable.

Body Weight Outcomes

Mean body weight of ALP201 and asfotase alfa treated Akp2GW (−/−) mice in all groups was consistently lower than that of their wild type littermates treated with PBS. End-of-study body weight for all ALP201 dosing groups was not statistically different from the asfotase alfa dosing groups.

Safety Pharmacology

Standalone safety pharmacology studies were not performed for ALP201. However, cardiovascular, respiratory, and blood pressure endpoints were measured as part of the pivotal GLP-compliant monkey toxicity study and neurofunctional endpoints were assessed as part of the rat GLP toxicity study. ALP201 treatment resulted in increases in heart rates (28% compared with the control group) only at the low dose group, with associated decreases in the RR, PR, QT intervals and without any notable changes in QRS duration; no biologically meaningful changes were observed in the mid and high dose groups. Therefore, there was no dose-response relationship between slight increases in heart rate and ALP201 dose. Since the heart rate increases were modest in magnitude, these findings are not considered to be adverse. Additionally, there were no ALP201-related findings on ECG, blood pressure, or respiratory parameters evaluated in monkeys following once every 3 days SC administration for 28-days up to the highest dose, 20 mg/kg, evaluated in the study. ALP201 had no effects on behavioral indices or motor activity in rats following once every 3 days SC administration for 28-days up to the highest dose, 30 mg/kg, evaluated in the study.

Pharmacokinetics and Drug Metabolism in Animals

Single dose PK studies were conducted in mice, rats, and monkeys. Data from these studies were used to assess the disposition (absorption, distribution, and elimination) of ALP201 in preclinical species.

Absorption

The PK of ALP201 was assessed in the Sprague-Dawley rat and the Cynomolgus monkey. Summaries of the non-GLP and GLP studies following single- and repeat-dose administration of ALP201 are presented herein.

The mean bioavailability was 96%, 58%, and 78% for mouse, rat, and monkey, respectively. The time to reach maximum concentration ($t_{max}$) ranged from 17 to 48 hours post-dosing, suggesting slow absorption of ALP201 from the SC injection site.

Distribution

Following single intravenous administration in mouse, rat, and monkey, ALP201 volume of apparent distribution ranged from 0.08 to 0.15 L/kg. This value was much greater (>2-fold) than the plasma volume in these species, indicating ALP201 distribution beyond the intra-vascular compartment.

Pharmacokinetics in Single-Dose Studies

Single Dose PK in Male C57BL/6 Mice (Study HPP-PK-01)

The PK of ALP201 was evaluated following single dose IV or SC administration to male C57BL/6 mice. Sixteen animals received a single IV or SC administration of ALP201 at a dose of 4 mg/kg. For each administration route, mice were randomly subdivided into 4 sampling cohorts of 4 mice each. Blood samples were collected using a semi-serial sampling design for up to 20 days after dose administration. PK parameters of ALP201 are summarized in Table 11.

TABLE 11

PK Parameters of ALP201 Following IV and SC Administration in C57BL/6 Mice

| Route | Dose (mg/kg) | $C_{max}$ (μg/mL) | $t_{max}$ (h) | $t_{1/2}$ (h) | $AUC_t$ (μg * h/mL) | $AUC_\infty$ (μg * h/mL) | $V_d$ or $V_d/F$ (L/kg) | CL or CL/F (L/h/kg) | F (%) |
|---|---|---|---|---|---|---|---|---|---|
| IV | 4 | 93.3 | 1 | 48.1 | 2070.1 | 2114.3 | 0.13 | 0.0019 | NA |
| SC | 4 | 15.2 | 48 | 85.2 | 1828.7 | 2030.3 | 0.24 | 0.0020 | 96 |

Abbreviations:
$AUC_\infty$ = area under the concentration time curve from time zero (dosing) extrapolated to infinity;
$AUC_t$ = area under the concentration time curve from time zero (dosing) to the last detectable concentration;
CL or CL/F = total clearance;
$C_{max}$ = maximum observed plasma concentration;
F = absolute bioavailability;
IV = intravenous;
NA = not applicable;
SC = subcutaneous;
$t_{max}$ = time to maximum observed plasma concentration;
$t_{1/2}$ = terminal elimination half-life;
$V_d$ or $V_d/F$ = apparent volume of distribution After IV administration, the concentration-time profile declined in a multi-exponential manner. The CL was 0.0019 L/h/kg and the apparent terminal t½ was 48 hours (Table 11 Tabl). The $V_d$ was 0.13 L/kg, which is greater than plasma volume in mouse indicating ALP201 distribution beyond the intra-vascular space. After SC administration, the time to reach maximum concentration ($t_{max}$) was 48 hours post dose, suggesting relatively slow absorption from the SC injection site. Absolute bioavailability following SC administration was 96%.

Single-Dose PK Study in Rats

Figure 14:
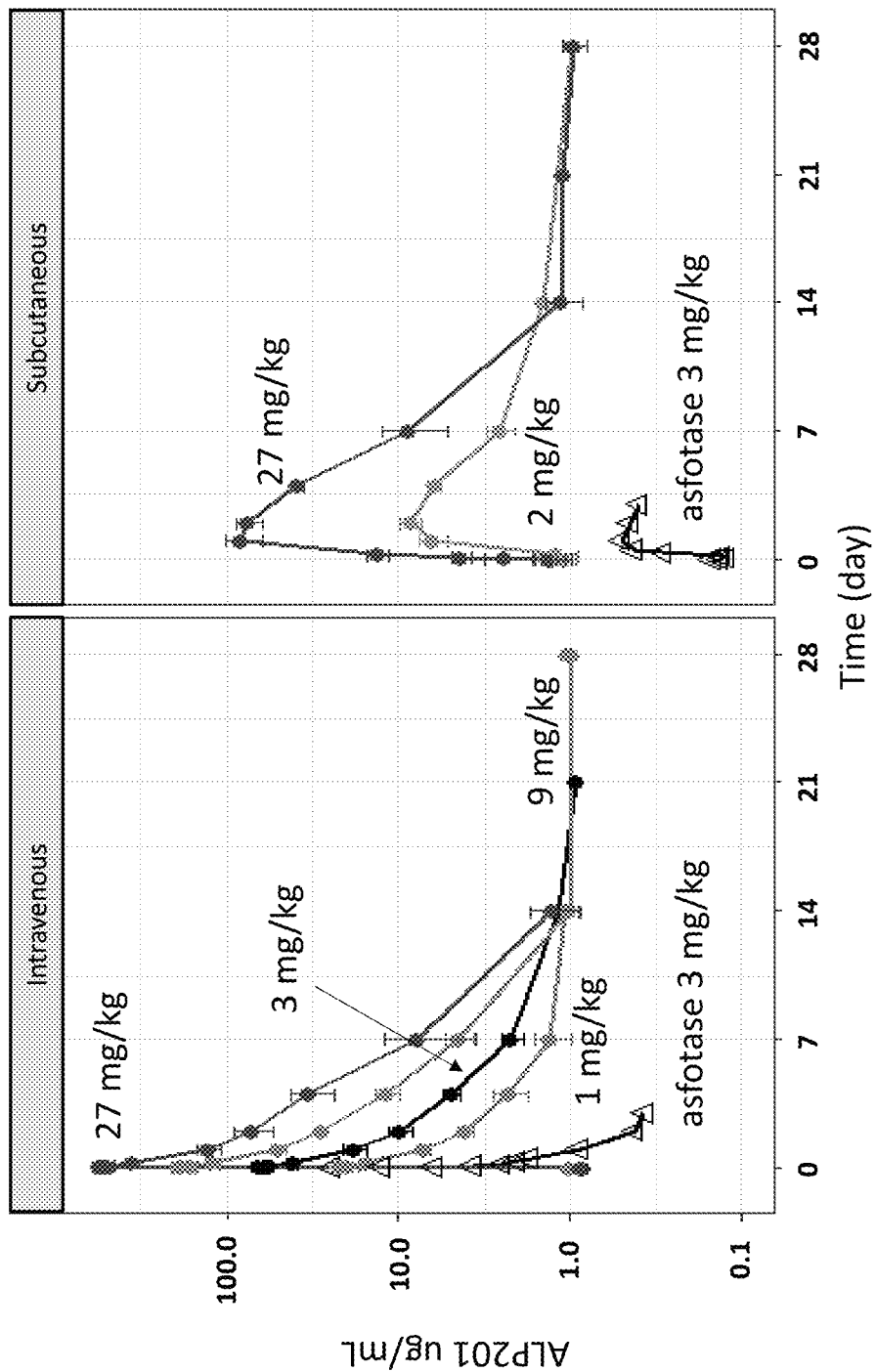
FIG. 14 is a graph showing a comparison of ALP201 and asfotase alfa mean (±SD) plasma concentration versus time profiles after single IV and SC administration in rats. Abbreviations: IV intravenous; SC=subcutaneous, SD=standard deviation. Asfotase alfa source data: pooled sex, IV and SC at 3 mg/kg.

The PK of ALP201 was evaluated following single IV or SC administration to rats. Four animals (2 per sex/dose) received a single IV or SC ascending dose (IV bolus at a dose of 1, 3, 9, or 27 mg/kg or SC at a dose of 2 or 27 mg/kg) of ALP201. ALP201 plasma concentrations were quantifiable for up to 28 days post dose. As no apparent sex-specific differences in ALP201 PK parameters were observed, pooled sex values are provided. Descriptive statistics for PK parameters of ALP201 are summarized for the pooled sex groups in Table 12. ALP201 mean plasma concentration versus time profiles are shown in FIG. 14; note that historical data for asfotase alfa are added to enable comparison.

TABLE 12

Mean (±SD) PK parameters of ALP201 following IV or SC Administration in Rats

| Route | Dose (mg/kg) | N | $t_{1/2}$ (h) | $t_{max}$ (h) | $C_{max}$ (μg/mL) | $AUC_t$ (h × μg/mL) | $AUC_\infty$ (h × μg/mL) | $V_d$ or $V_d/F$ (L/kg) | CL or CL/F (L/h/kg) |
|---|---|---|---|---|---|---|---|---|---|
| IV | 1 | 4 | 66.6 ± 5.6 | 0.5 ± 0.0 | 22.4 ± 0.8 | 716.5 ± 47.3 | 802.1 ± 60.1 | 0.12 ± 0.02 | 0.0012 ± 0.0001 |
| IV | 3 | 4 | 58.7 ± 14.0 | 0.6 ± 0.3 | 65.7 ± 1.5 | 1811.2 ± 142.3 | 1934.4 ± 196.0 (10.1) | 0.13 ± 0.04 | 0.0015 ± 0.0002 |
| IV | 9 | 4 | 63.7 ± 12.6 | 0.8 ± 0.3 | 194.1 ± 26.7 | 5299.7 ± 435.0 | 5374.1 ± 442.9 | 0.15 ± 0.03 | 0.0017 ± 0.0001 |
| IV | 27 | 4 | 43.6 ± 12.2 | 0.5 ± 0.0 | 559.1 ± 25.4 | 14089.0 ± 2003.9 | 14234.3 ± 2053.1 | 0.12 ± 0.03 | 0.0019 ± 0.0002 |

TABLE 12-continued

Mean (±SD) PK parameters of ALP201 following IV or SC Administration in Rats

| Route | Dose (mg/kg) | N | $t_{1/2}$ (h) | $t_{max}$ (h) | $C_{max}$ (µg/mL) | $AUC_t$ (h × µg/mL) | $AUC_\infty$ (h × µg/mL) | $V_d$ or $V_d/F$ (L/kg) | CL or CL/F (L/h/kg) |
|---|---|---|---|---|---|---|---|---|---|
| SC | 2 | 4 | 55.1 ± 6.7 | 48.0 ± 0.0 | 8.1 ± 1.9 | 869.0 ± 123.4 | 1007.7 ± 124.6 | 0.16 ± 0.03 | 0.0020 ± 0.0002 |
| SC | 27 | 4 | 38.3 ± 6.9 | 30.4 ± 11.7 | 82.2 ± 19.6 | 7188.2 ± 1201.9 | 7674.2 ± 1406.1 | 0.19 ± 0.03 | 0.0036 ± 0.0007 |

Abbreviations:
$AUC_\infty$ = area under the concentration time curve from time zero (dosing) extrapolated to infinity;
$AUC_t$ = area under the concentration time curve from time zero (dosing) to the last detectable concentration;
CL or CL/F = total clearance;
$C_{max}$ = maximum observed plasma concentration;
IV = intravenous;
SC = subcutaneous;
SD = standard deviation;
$t_{max}$ = time to maximum observed plasma concentration;
$t_{1/2}$ = terminal elimination half-life;
$V_d$ or $V_d/F$ = apparent volume of distribution.

For IV administration, ALP201 PK exposure ($C_{max}$ and $AUC_\infty$) increased in a slightly less than dose proportional manner over the studied dose range of 1 mg/kg to 27 mg/kg. The mean CL and $V_d$ of ALP201 remained consistent across doses. The mean CL values ranged from 0.0012 to 0.0019 L/h/kg and mean $V_d$ values ranged from 0.12 to 0.15 L/kg. Similarly, the t½ of ALP201, which remained relatively similar across IV doses, averaged about 2 days. For SC administration, the CL/F, $V_d/F$, and $t_{1/2}$ values were similar to those estimated from IV administration, except for the 27 mg/kg SC dose group, which appeared to be an outlier. The mean $t_{max}$ ranged from 30 to 48 hours post dose, suggesting relatively slow absorption from the SC injection site. Absolute bioavailability following SC administration was 61% and 54% for the 2 and 27 mg/kg dose, respectively.

Single-Dose PK Study in Monkeys

Figure 15:
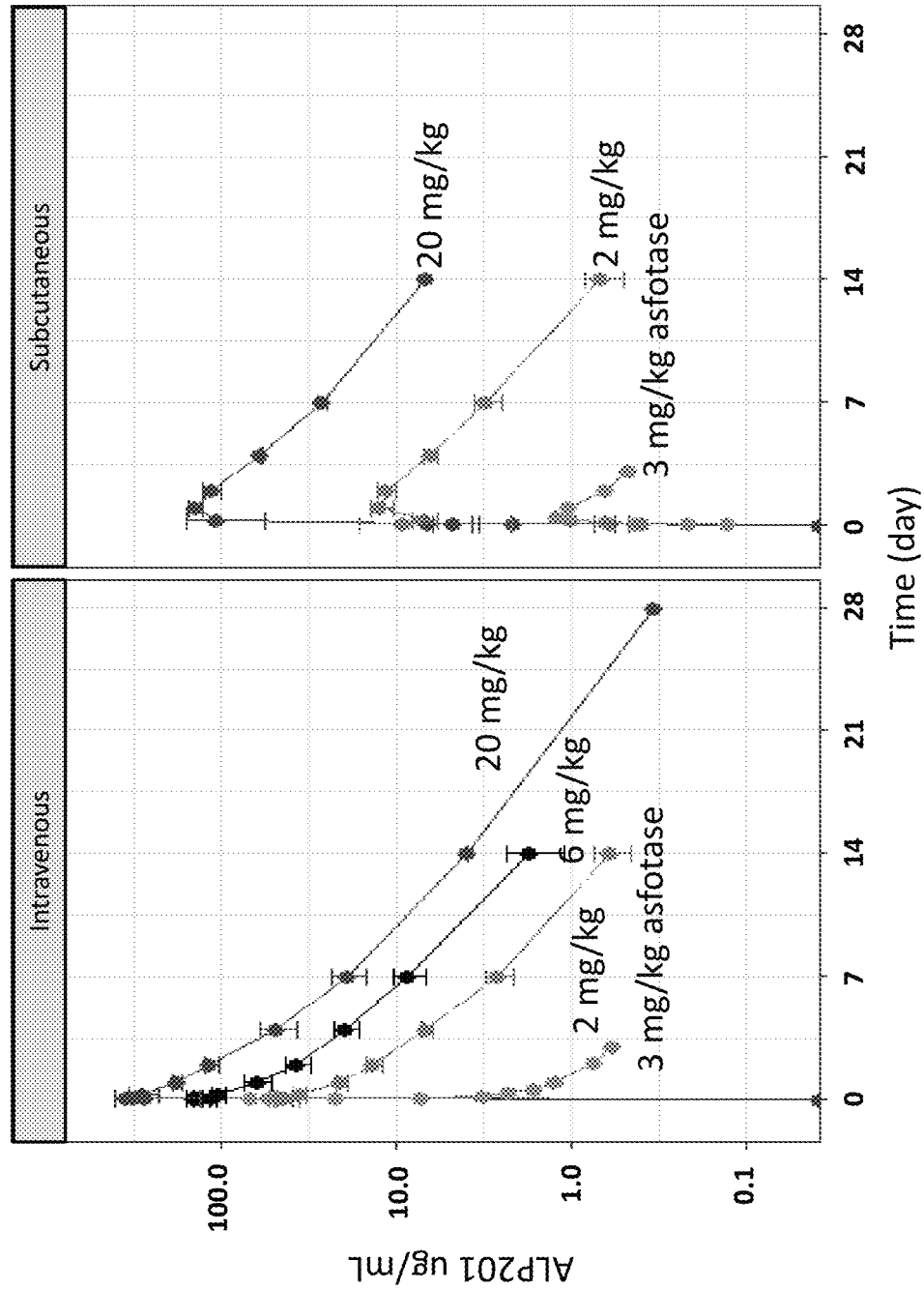
FIG. 15 is a graph showing a comparison of ALP201 and asfotase alfa mean (±SD) plasma concentration versus time profiles after single IV and SC administration in monkeys.

The PK of ALP201 was evaluated following single IV or SC administration to monkey. Three male monkeys received a single IV or SC ascending dose (IV bolus at a dose of 2, 6, or 20 mg/kg or SC at a dose of 2 or 20 mg/kg) of ALP201. ALP201 plasma concentrations were quantifiable for up to 28 days post dose. Descriptive statistics for PK parameters of ALP201 are summarized in Table 13Tabl. ALP201 mean plasma concentration versus time profiles are shown in FIG. 15. Note that historical data for asfotase alfa are added to enable comparison.

TABLE 13

Mean (±SD) PK parameters of ALP201 following single IV or SC Administration in Monkeys

| Route | Dose (mg/kg) | N | $T_{max}$ (h) | $C_{max}$ (µg/mL) | $t_{1/2}$ (h) | $AUC_t$ (h × µg/mL) | $AUC_\infty$ (h × µg/mL) | $V_d$ or $V_d/F$ (L/kg) | CL or CL/F (L/h/kg) |
|---|---|---|---|---|---|---|---|---|---|
| IV | 2 | 3 | 0.7 ± 0.3 | 48.0 ± 6.6 | 68.3 ± 5.7 | 2298.4 ± 212.5 | 2358.5 ± 232.5 | 0.08 ± 0.00 | 0.0008 ± 0.0001 |
| IV | 6 | 3 | 0.7 ± 0.3 | 146.5 ± 12.6 | 66.8 ± 8.4 | 6394.2 ± 519.0 | 6814.7 ± 885.3 | 0.09 ± 0.02 | 0.0009 ± 0.0001 |
| IV | 20 | 3 | 2.4 ± 3.2 | 416.7 ± 166.6 | 60.4 ± 20.8 | 17838.9 ± 2737.0 | 18248.2 ± 2530.2 | 0.10 ± 0.03 | 0.0011 ± 0.0002 |
| SC | 2 | 3 | 17.4 ± 13.3 | 13.7 ± 2.4 | 72.7 ± 5.8 | 1593.4 ± 168.5 | 1665.3 ± 187.9 | 0.13 ± 0.01 | 0.0012 ± 0.0001 |
| SC | 20 | 3 | 18.8 ± 10.9 | 149.9 ± 17.7 | 62.0 ± 13.2 | 14064.2 ± 835.3 | 15662.6 ± 189.0 | 0.11 ± 0.02 | 0.0013 ± 0.0 |

Abbreviations:
$AUC_\infty$ = area under the concentration time curve from time zero (dosing) extrapolated to infinity;
$AUC_t$ = area under the concentration time curve from time zero (dosing) to the last detectable concentration;
CL or CL/F = total clearance;
$C_{max}$ = maximum observed plasma concentration;
CV = coefficient of variation;
IV = intravenous;
SC = subcutaneous;
SD = standard deviation;
$t_{max}$ = time to maximum observed plasma concentration;
$t_{1/2}$ = terminal elimination half-life;
$V_d$ or $V_d$ = apparent volume of distribution.

For IV administration, the increases in $C_{max}$ and $AUC_\infty$ values were close to dose proportional over the studied dose range of 2 mg/kg to 20 mg/kg. The CL and $V_d$ of ALP201 remained consistent across doses, the mean CL values ranged from 0.0008 to 0.0011 L/h/kg and mean $V_d$ values ranged from 0.08 to 0.10 L/kg. The $t_{1/2}$ of ALP201, which remained relatively similar across doses as well, averaged about 3 days. For SC administration, the mean CL/F, $V_d/F$, and $t_{1/2}$ values were consistent with those estimated after the IV administration. The mean $t_{max}$ ranged from 17 to 19 hours post-dose, suggesting relatively slow absorption from the SC injection site. Absolute bioavailability was 69.6% and 86.9% for the 2 mg/kg and the 20 mg/kg dose, respectively.
Repeated Dose Toxicokinetics Studies with ALP201

Four-week SC Administration in Rats (1727-227): ALP201 was administered SC to rats at 2, 10 or 30 mg/kg/dose once every 3 days for 4 weeks. In addition, ALP201 was intravenously administered to rats with single dose at 10 mg/kg to compare IV and SC route bioavailability. Pharmacokinetic parameters were calculated using non-compartment analysis from ALP201 composite plasma concentrations following Day 0 and Day 24 dosing and are shown in Table 14.

Systemic exposure to ALP201 appeared to be independent of sex following SC administration of ALP201 on Days 0 and 24 and following a single IV bolus injection of ALP201 on Day 0. Following SC administration of ALP201 every 3 days, $C_{max}$ and $AUC_{0-72h}$ values for ALP201 increased with increasing dose in a slightly less than dose proportional manner on Days 0 and 24. Systemic exposure ($AUC_{0-72h}$) to ALP201 appeared to decrease following repeated SC administration. The exposure reduction appeared to be dose dependent with maximum reduction up to 2-fold following repeated SC administration of 30 mg/kg ALP201. Subcutaneous bioavailability for ALP201 (based on $AUC_{0-72h}$ values at 10 mg/kg) was approximately 44.2%.

TABLE 14

Toxicokinetic Parameters following 4-Week Repeated SC or Single IV Administration in Rats

| Route | Dose (mg/kg) | Day | $C_{max}$ (μg/mL) | $C_{max}$/Dose (μg/mL)/(mg/kg) | $T_{max}$ (hr) | $AUC_{0-72h}$ (hr × μg/mL) | $AUC_{0-72h}$/Dose (hr × μg/mL)/(mg/kg) | $AUC_{0-168h}$ (hr × μg/mL) | $R^a$ | $F^b$ (%) |
|---|---|---|---|---|---|---|---|---|---|---|
| SC | 2 | 0 | 7.94 | 3.97 | 48 | 429 | 214 | 1320 | NA | NA |
| SC | 2 | 24 | 6.13 | 3.06 | 24 | 338 | 169 | 841 | 0.789 | NA |
| SC | 10 | 0 | 30.4 | 3.04 | 24 | 1630 | 163 | 4810 | NA | 44.2 |
| SC | 10 | 24 | 22.5 | 2.25 | 24 | 1200 | 120 | 2760 | 0.735 | NA |
| SC | 30 | 0 | 79.9 | 2.66 | 24 | 4150 | 138 | 11600 | NA | NA |
| SC | 30 | 24 | 43.9 | 1.46 | 24 | 2120 | 70.7 | 4380 | 0.512 | NA |
| IV | 10 | 0 | 195 | 19.5 | 2 | 3690 | 4720 | NA | NA | NA |

$^a$R = $AUC_{0-72h}$ Day 24/$AUC_{0-72h}$ Day 0.
$^b$F = $AUC_{0-72h}$ from 10 mg/kg SC dose group Day 0/$AUC_{0-72h}$ 10 mg/kg IV dose group Day 0 * 100
Abbreviations:
$AUC_{0-72h}$ = Area under the plasma concentration-time curve from 0 to 72 hours;
$AUC_{0-168h}$ = Area under the plasma concentration-time curve from 0 to 168 hours;
$C_{max}$ = maximum observed plasma concentration;
IV = intravenous;
SC = subcutaneous;
NA = not applicable;
$T_{max}$ = time to maximum observed plasma concentration.

Four-week SC Administration in Monkeys: ALP201 was SC administered to monkeys at 1, 5 or 20 mg/kg/dose once every 3 days for 4 weeks. The PK parameters were calculated using non-compartment analysis from ALP201 plasma concentrations following Day 1 and Day 24 dosing and are shown in Table 15.

TABLE 15

ALP201 Toxicokinetic Parameters following 4-Week Repeated SC Administration in Monkeys

| Dose (mg/kg) | Day | $C_{max}$ (μg/mL) | $C_{max}$/Dose (μg/mL)/(mg/kg) | $T_{max}^a$ (hr) | $AUC_{0-72h}$ (hr × μg/mL) | $AUC_{0-72h}$/Dose (hr × μg/mL)/(mg/kg) | $AUC_{0-168h}$ (hr × μg/mL) | $R^b$ |
|---|---|---|---|---|---|---|---|---|
| 1 | 0 | 6.73 | 6.73 | 48 | 391 | 391 | 1440 | NA |
| 1 | 24 | 10.9 | 10.9 | NA | 787 | 787 | 2200 | 2.12 |
| 5 | 0 | 29.2 | 5.85 | 48 | 1720 | 345 | 6030 | NA |
| 5 | 24 | 38.1 | 7.62 | 24 | 2870 | 575 | 6970 | 1.83 |
| 20 | 0 | 125 | 6.25 | 48 | 7310 | 366 | 27900 | NA |
| 20 | 24 | 254 | 12.7 | 24 | 15400 | 772 | 36800 | 2.15 |

$^a$Median (minimum-maximum), median value only reported if actual collection interval
$^b$R = $AUC_{0-72h}$ Day 24/$AUC_{0-72h}$ Day 0.
Abbreviations:
$AUC_{0-72h}$ = Area under the plasma concentration-time curve from 0 to 72 hours;
$AUC_{0-168h}$ = Area under the plasma concentration-time curve from 0 to 168 hours;
$C_{max}$ = maximum observed plasma concentration;
IV = intravenous;
NA = Not applicable;
SC = subcutaneous;
$T_{max}$ = time to maximum observed plasma concentration.

Systemic exposure to ALP201 appeared to be independent of sex following SC administration of ALP201 on Days 0 and 24. Following subcutaneous administration of ALP201 every 3 days, $C_{max}$ and $AUC_{0-72h}$ values for ALP201 increased with increasing dose in an approximately dose proportional manner on Days 0 and 24. Systemic exposure ($AUC_{0-72h}$ values) to ALP201 appeared to increase following repeated subcutaneous administration of ALP201 on Day 24.

Pharmacokinetics, Pharmacodynamics, and Immunogenicity in Repeat-Dose Studies 28-Day Toxicity Study in Rats with a 28-Day Recovery Period The TK/ADA of ALP201 was evaluated in male and female rats following SC administration of 2, 10, or 30 mg/kg once every three days (10/sex/dose group, 5/sex/timepoint) for 4 weeks (a total of 10 doses) and a single IV dose of 10 mg/kg (total of 1 dose). Blood samples for TK analysis were collected over a 72-hour period from all animals starting on Days 0 and 24. PK parameters of ALP201 are summarized in Table 16.

pooled sex results were included Table 16. Following SC administration of ALP201 every 3 days (q3d), ALP201 exposure ($C_{max}$ and $AUC_{72h}$) increased with increasing dose in a slightly less than dose proportional manner on Days 0 and 24. Systemic exposure ($C_{max}$ and $AUC_{72h}$) on Day 24 appeared to decrease following repeated SC administration. The exposure reduction appeared to be dose dependent with maximum reduction up to 60% following repeated SC administration of 30 mg/kg ALP201. Subcutaneous bioavailability for ALP201 was approximately 44.2%.

The ADA response was negative for all pre-dose samples. The ADA incidence rate was 58% and 90% for D28 and D56 post-dose ADA samples, respectively. The exposure reduction on Day 24 (60%) for the 30 mg/kg dose was likely due to immunogenicity response.

28-Day Toxicity Study in Monkeys with a 28-Day Recovery Period

The TK/ADA of ALP201 was evaluated in male and female monkeys following SC administration of 1, 5, or 20 mg/kg once every three days (5/sex/dose group) for 4 weeks

TABLE 16

Mean PK parameters of ALP201 on Day 0 and Day 24 Following Repeated SC or Single IV Administration in Rats

| Route | Dose (mg/kg) | Day | $C_{max}$ (µg/mL) | $t_{max}$ (hr) | $AUC_{72h}$ (hr × µg/mL) | $AUC_{168h}{}^a$ (hr × µg/mL) | $R^b$ | $F^c$ (%) |
|---|---|---|---|---|---|---|---|---|
| SC | 2 | 0 | 7.94 | 48 | 429 | 1320 | NA | NA |
| SC | 2 | 24 | 6.13 | 24 | 338 | 841 | 0.789 | NA |
| SC | 10 | 0 | 30.4 | 24 | 1630 | 4810 | NA | 44.2 |
| SC | 10 | 24 | 22.5 | 24 | 1200 | 2760 | 0.735 | NA |
| SC | 30 | 0 | 79.9 | 24 | 4150 | 11600 | NA | NA |
| SC | 30 | 24 | 43.9 | 24 | 2120 | 4380 | 0.512 | NA |
| IV | 10 | 0 | 195 | 2 | 3690 | NA | NA | NA |

$^a AUC_{168h}$ values were calculated on day 0 and Day 18
$^b R = AUC_{72h}$ Day $24/AUC_{72h}$ Day 0.
$^c F = AUC_{72h}$ from 10 mg/kg SC dose group Day $0/AUC_{72h}$ 10 mg/kg IV dose group Day 0 * 100
Abbreviations:
$AUC_{72h}$ = area under the plasma concentration-time curve from 0 to 72 hours;
$AUC_{168h}$ = area under the plasma concentration-time curve from 0 to 168 hours;
$C_{max}$ = maximum observed plasma concentration;
F = bioavailability;
IV = intravenous;
SC = subcutaneous;
NA = not applicable;
$t_{max}$ = time to maximum observed plasma concentration;
R = accumulation ratio Systemic exposure to ALP201 appeared to be independent of sex following repeated SC administration of ALP201 and following a single IV bolus injection of ALP201. Therefore, (a total of 10 doses). Blood samples for TK analysis were collected on Day 0 and 24. Descriptive statistics for PK parameters of ALP201 are summarized in Table 17.

TABLE 17

Mean (±SD) PK parameters of ALP201 on Day 0 and Day 24 Following Repeated SC Administration in Monkeys

| Dose (mg/kg) | Day | Statistic | $C_{max}$ (µg/mL) | $t_{max}{}^a$ (hr) | $AUC_{72h}$ (hr * µg/mL) | $AUC_{168h}{}^b$ (hr * µg/mL) | $R^c$ |
|---|---|---|---|---|---|---|---|
| 1 | 0 | N | 10 | 10 | 10 | 10 | NA |
|   |   | Mean ± SD | 6.73 ± 1.44 | 48 (24-48) | 391 ± 99.9 | 1440 ± 298 | NA |
| 1 | 24 | N | 10 | 10 | 8 | 7 | 8 |
|   |   | Mean ± SD | 10.9 ± 7.48 | NA (8-24) | 787 ± 346 | 2200 ± 320 | 2.12 ± 1.11 |
| 5 | 0 | N | 10 | 10 | 10 | 10 | NA |
|   |   | Mean ± SD | 29.2 ± 4.44 | 48 (24-48) | 1720 ± 317 | 6030 ± 723 | NA |
| 5 | 24 | N | 10 | 10 | 8 | 8 | 8 |
|   |   | Mean ± SD | 38.1 ± 24.2 | 24 (8-24) | 2870 ± 1140 | 6970 ± 2600 | 1.83 ± 0.805 |
| 20 | 0 | N | 10 | 10 | 10 | 10 | NA |
|   |   | Mean ± SD | 125 ± 29.4 | 48 (24-48) | 7310 ± 1760 | 27900 ± 5130 | NA |

TABLE 17-continued

Mean (±SD) PK parameters of ALP201 on Day 0 and
Day 24 Following Repeated SC Administration in Monkeys

| Dose (mg/kg) | Day | Statistic | $C_{max}$ (µg/mL) | $t_{max}$[a] (hr) | $AUC_{72h}$ (hr * µg/mL) | $AUC_{168h}$[b] (hr * µg/mL) | R[c] |
|---|---|---|---|---|---|---|---|
| 20 | 24 | N | 10 | 10 | 8 | 10 | 8 |
|    |    | Mean ± SD | 254 ± 62 | 24 (8-24) | 15400 ± 4420 | 36800 ± 12300 | 2.15 ± 0.59 |

[a]Median (minimum-maximum), median value only reported if actual collection interval
[b]$AUC_{0-168hr}$ values were calculated on Day 0 and Day 18
[c]R = $AUC_{72hr}$ Day 24/$AUC_{72hr}$ Day 0.
Abbreviations:
$AUC_{72h}$ = Area under the plasma concentration-time curve from 0 to 72 hours;
$AUC_{168h}$ = Area under the plasma concentration-time curve from 0 to 168 hours;
$C_{max}$ = maximum observed plasma concentration;
NA = Not applicable;
$t_{max}$ = time to maximum observed plasma concentration;
R = accumulation ratio.

There were no sex differences in the systemic exposure to ALP201 on Days 0 and 24. Therefore, pooled sex results were included in Table 17. Following subcutaneous administration of ALP201 once every 3 days, ALP201 ($C_{max}$ and $AUC_{72h}$) increased with increasing dose in an approximately dose proportional manner on Days 0 and 24. Systemic exposure ($AUC_{72h}$ values) to ALP201 appeared to increase following repeated subcutaneous administration of ALP201 on Day 24, with mean accumulation $AUC_{72h}$ ratios of 2.12, 1.83, and 2.15 at 1, 5, and 20 mg/kg, respectively.

The ADA response was negative for pre-dose samples. The ADA incidence rate was 23% and 92% for D28 and D56 post-dose ADA samples, respectively. Although a direct correlation could not be made between positive ADA responses and systemic exposure concentration-time profiles as ADA samples were not sampled on TK collection days, following multiple doses, aberrant concentration-time profiles for some of the animals at mg/kg appeared to be impacted by anti ALP201 antibodies.

Model-Based Analyses and Predicted Human Dose Regimens
ALP201 Modelling
Population Pharmacokinetics (Pop-PK) Model To forecast ALP201 exposure in humans given mouse dose-response results, a Pop-PK model was developed using body weight-based allometric scaling and pooling mouse, rat, and monkey PK data to predict human PK parameter estimates. Mouse PK data included a single dose wild-type mouse study (HPP-PK-01) and single $C_{trough}$ measurements (D36/D37) from 2 multiple dose Akp2GW (−/−) mouse efficacy studies (HPP-PoC-01 and HPP-MED-01). For rat and monkey, single dose, dose range-finding studies in rats and cynomolgus monkeys, and multiple dose 4-week GLP toxicology studies in rat and cynomolgus monkeys were also included.

The current Pop-PK model was developed using the NONMEM software program, version 7.2 (ICON solutions) to simultaneously analyze the IV and SC PK data from 3 animal species accounting for body-weight differences using allometric principles, where animal body weight was centered to 70 kg and allometric exponents were fixed to 0.75 for clearance parameters and 1.0 for volume of distribution parameters. The impact of ADA on PK was assessed on CL based on the 4-week TK showing that rats, and to a lesser degree, monkeys appeared to have lower ALP201 concentrations for ADA+ animals. The current best Pop-PK model is a two-compartment model with linear elimination. The testing of ADA+ impact on ALP201 concentrations was inconclusive. The estimated bioavailability in humans was ~75% and the calculated effective half-life for humans was 7 to 9 days. The human PK simulations used the estimated variability from the human asfotase alfa Pop-PK model and mean (and standard deviation) adult baseline body weights of HPP subjects who took part in the clinical trials evaluating asfotase alfa as a treatment for HPP.

Dose-Response Model

Figure 6:
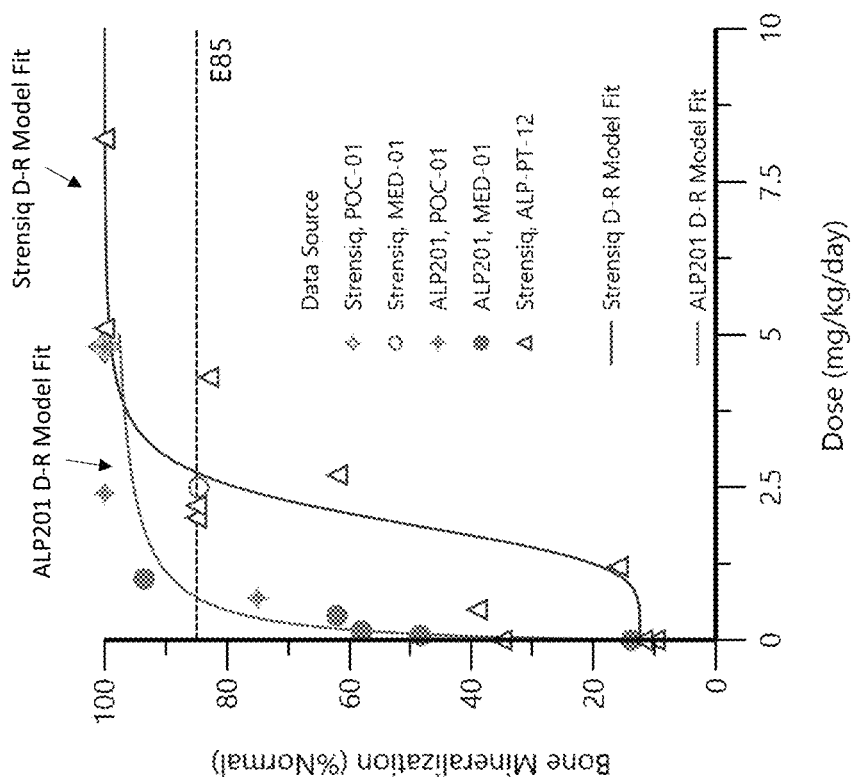
FIG. 6 is a graph showing a comparison of ALP201 and asfotase alfa dose-response modeling results. Abbreviations: ALP=alkaline phosphatase; D-R=dose response; MED=minimum efficacious dose; POC=proof of concept.

The developed dose-response model was selected by testing models from the $E_{max}$ family. Most dose-response relationships can be described by one of the $E_{max}$ model parameterizations. The current best dose-response characterization is using an $E_{max}+E_0$ (baseline) model. The efficacy endpoint, bone mineralization, was a radiographic assessment that was selected as it shared the same clinical definition of efficacy as that used for asfotase alfa nonclinical dose-response assessment. Bone mineralization after treatment with asfotase alfa or ALP201 from 2 efficacy studies (HPP-PoC-01 and HPP-MED-01) was plotted versus dose (FIG. 6). Asfotase alfa data from previous efficacy study was included for comparison. The y-axis was expressed as % Normal, which was defined as the percentage of mice in a dose group with bone mineralization scores of 4. The x-axis was expressed as dose normalized to mg/kg/day. The dose producing normal mineralization in 85% of the treated population (ED85) was chosen as the target effective dose.

Dose Translation from Mouse to Human and Proposed Human Starting Doses

Allometric scaling was applied to mouse target effective dose (ED85) to determine a human dose. The equation used to predict from mouse ED85 to human equivalent dose (HED, mg/kg/day) was ED85×(0.025 kg mouse/70 kg human)$^{0.25}$. The HED was translated into a weekly flat dose of 45 mg/week and will be used as the dose for the FIH study Cohort 2 (both IV and SC). Cohort 3 (IV and SC) will use 90 mg/week. Cohort 1 will use a NOAEL-based starting dose of 15 mg/week (both IV and SC).

Predicted Human Exposure and Safety PK Margins for ALP201

Figure 7:
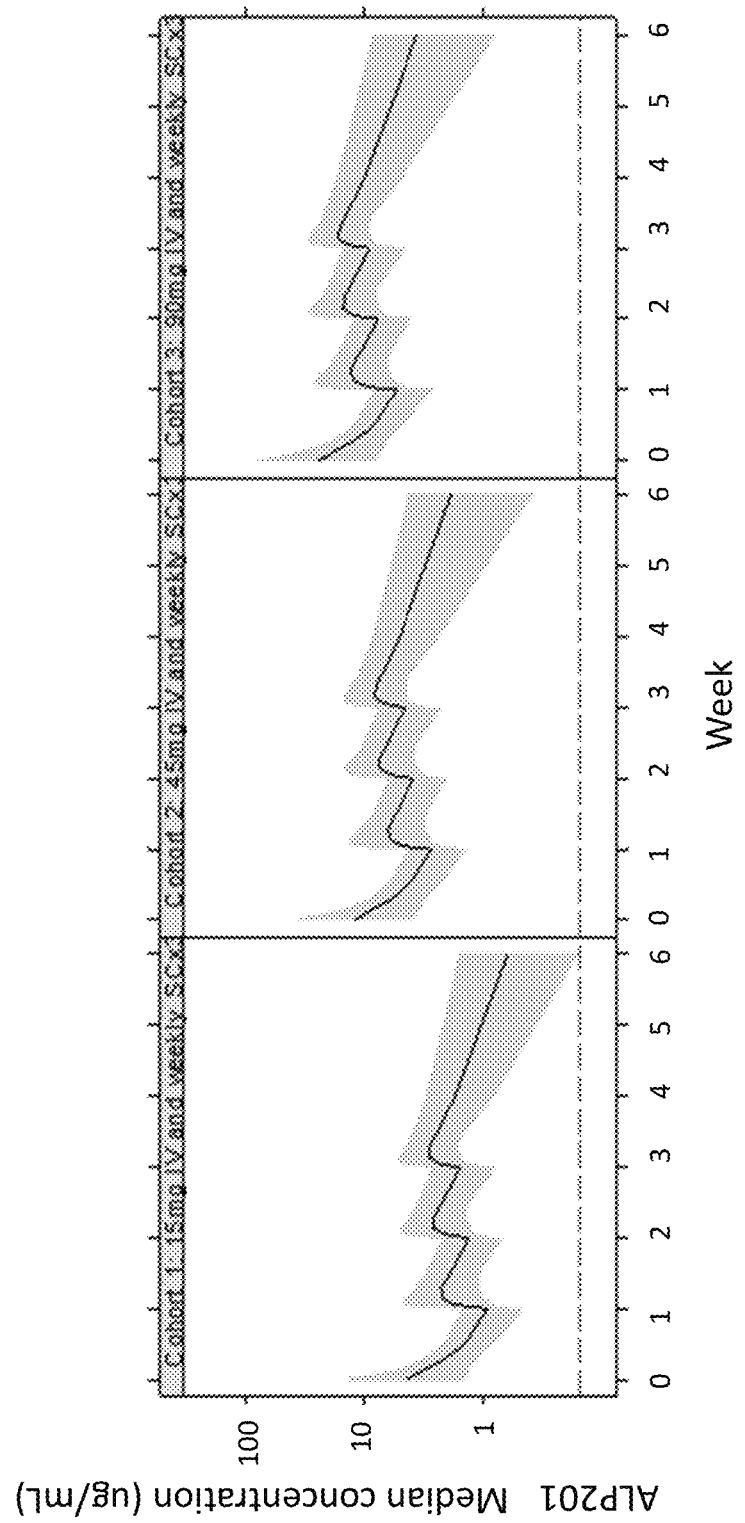
FIG. 7 is a graph showing simulated human ALP201 concentration-time profiles for each first-in-human (FIH) cohorts. Gray region represents the 90% prediction interval, i.e., 5% to 95% range; black solid line is the median of the simulated concentration-time profiles; LLOQ is the horizontal dashed line for the PK assay; Abbreviations: LLOQ=lower limit of quantitation (0.15 μg/mL).

The Pop-PK model was used to simulate rich PK profiles based on allometrically-scaled doses to human (FIG. 7). Using the simulated PK data, the exposure metrics $C_{max}$ and AUC were calculated.

The predicted human exposures ($C_{max}$ and $AUC_{168h}$) and expected safety PK margins for proposed FIH ALP201 doses are shown in Table 18. Safety PK margins were calculated for the proposed FIH ALP201 doses using predicted human exposure and observed NOAEL exposure from the 4-week GLP monkey toxicology study (NOAEL dose at 20 mg/kg/Q3D administered SC).

TABLE 18

Predicted ALP201 PK Exposure, Safety Margin, and % Normalized Mineralization Response

| Cohort | N | Dose | Predicted $AUC_{168h}$ (μg × hour/mL) | Predicted $C_{max}$ (μg/mL) | Expected Safety Margin for $AUC_{168h}$* | Expected Safety Margin for $C_{max}$* | % Normal Mineralization Response in Mouse HPP Model |
|---|---|---|---|---|---|---|---|
| 1 | 4 | 15 mg IV | 325 | 4.3 | 113 | 59 | NA |
|   |   | 15 mg SC biweekly × 3 | 441 | 3.2 | 83 | 79 | 66 |
| 2 | 4 | 45 mg IV | 1084 | 13.0 | 38 | 20 | NA |
|   |   | 45 mg SC biweekly × 3 | 1318 | 9.6 | 28 | 26 | 85 |
| 3 | 4 | 90 mg IV | 1951 | 26 | 19 | 10 | NA |
|   |   | 90 mg SC biweekly × 3 | 2645 | 19 | 14 | 13 | 91 |

Abbreviations:
$AUC_{168h}$ = the area under the concentration time curve from time zero to 168 hour;
$C_{max}$ = the maximum observed concentration measured after dosing;
HPP = hypophosphatasia;
IV = intravenous;
N = number of subjects;
SC = subcutaneous;
NA = not available
*NOAEL of 20 mg/kg/q3d from monkey 4-week SC toxicology study.

Toxicology Studies

Nonclinical safety studies were conducted in rat and monkeys to evaluate local tolerability, systemic toxicity, and safety pharmacology parameters following SC administration of ALP201 for up to 28 days. Nonclinical safety evaluation of single-dose IV administration of ALP201 was also evaluated in rat 28-day toxicity study to characterize the bioavailability of SC ALP201.

Single-Dose Toxicology Studies

Standalone single-dose tolerability studies were not conducted for ALP201. However, ALP201 tolerability in rats and monkeys was evaluated as part of single-dose PK studies. The tolerability of ALP201 was assessed by clinical observations, including site of injection reactions and clinical pathology data. No noteworthy ALP201-related injection site reactions, clinical observations, and clinical pathology observations were noted in rats or monkeys single-dose PK studies. In summary, single doses of ALP201 were well tolerated when administered via IV or SC in rats up to 27 mg/kg and in monkeys up to 20 mg/kg. The doses for ALP201 repeated dose definitive (GLP) toxicology studies were selected based on the tolerability and clinical pathology data obtained.

Repeat Dose Toxicology Studies

Definitive or GLP-compliant 28-day toxicity studies were conducted in Sprague-Dawley rats and Cynomolgus monkeys. In rat 28-day toxicity study, administration of ALP201 via subcutaneous injection once every 3 days for 28 days (Days 1, 4, 7, 10, 13, 16, 19, 22, 25, and 28) for a total of 10 doses to male and female CD® rats was well tolerated up to 30 mg/kg/dose, the highest SC dose evaluated in this study. Additionally, administration of ALP201 at 10 mg/kg IV was also well tolerated after a single injection. There were no ALP201-related changes in clinical observations, body weights, body weight gains, quantitative food consumption, ophthalmology, functional observational battery, hematology, urinalysis, gross pathology, and organ weights. At the end of the dosing phase, there were dose-related increases in alkaline phosphatase (ALP) activity (anticipated pharmacology effect) at mg/kg/dose ALP201 SC which were fully resolved following a 28-day recovery period. Non-adverse microscopic changes were related to the injection procedures with associated reactive changes in the draining lymph nodes. There was no discernible ALP201-associated alteration in the incidence, severity, or microscopic character of the changes at the injection sites or draining lymph nodes. Microscopic changes in the injection sites and draining lymph nodes of recovery animals were similar to those noted in the terminal necropsy animals, although less pronounced in the recovery group animals. In conclusion, the dose level of 30 mg/kg/dose is considered to be the no observed-adverse-effect-level (NOAEL) for subcutaneous administration; this corresponds to a Day 24 male and female combined $C_{max}$ value of 43.9 μg/mL and an $AUC_{0-72hr}$ value of 2120 hr*μg/mL.

Following a single IV bolus injection of 10 mg/kg ALP2-1 in rats resulted in an $AUC_{0-72hr}$, of 3690 h*μg/mL. The SC bioavailability for ALP201 (based on SC $AUC_{0-72hr}$ values at 10 mg/kg/dose) in rats was approximately 44.2%.

In monkey 28-day toxicity study, administration of ALP201 via SC injection once every 3 days for 28 days (a total of 10 days on Days 1, 4, 7, 10, 13, 16, 19, 22, 25, and 28), at doses of 1 mg/kg, 5 mg/kg, or 20 mg/kg to male and female cynomolgus monkeys was well tolerated up to 20 mg/kg/dose, the highest dose evaluated in this study. There were no ALP201-related changes in injection site reactions (dermal scoring), body weights, body weight gains, qualitative food consumption, ophthalmology, manual respiratory rates, indirect blood pressures, qualitative electrocardiography, hematology, urinalysis, gross pathology, and organ weights. At the end of the dosing phase, there were dose-related increases in alkaline phosphatase (ALP) activity (anticipated pharmacology effect), which were fully (1 mg/kg/dose) or mostly (5 mg/kg/dose) resolved following a 28-day recovery period. Non-adverse ALP201-related microscopic changes were confined to the injection sites and included minimal to mild degeneration/necrosis, mineralization, and mixed cell inflammation/infiltration. Partial recovery of degeneration/necrosis and mixed cell inflammation/infiltration of the injection site(s) were observed within the recovery groups, while minimal to mild mineralization persisted in recovery males at mg/kg/dose and females at 20 mg/kg/dose. Heart rate increases were observed in all animals at ≥1 mg/kg/dose and in some of the animals at mg/kg/dose. These heart rate increases were not considered to be adverse because, in addition to systemic exposure data incongruity, the heart rate and ECG values remained within the normal range of biological variation for monkeys of this age. In conclusion, the dose level of 20 mg/kg/dose is considered to be the no observed-adverse-effect-level (NOAEL), this corresponds to a Day 24 male and female combined mean $C_{max}$ value of 254 µg/mL and a mean $AUC_{0-72hr}$ value of 15400 hr*µg/mL respectively.

Local Tolerance

Standalone nonclinical studies were not conducted to evaluate local tolerability. However, evaluation of injection sites was performed in the SC ALP201 in rat and monkey general toxicology studies and IV ALP201 in rat general toxicology study. Subcutaneous and IV administrations of ALP201 was well tolerated locally in monkeys, with no adverse findings observed at the sites of injection Summary of Nonclinical Observations Relevant to Clinical Studies of ALP201

Safety Assessment

There were no ALP201-related changes in clinical observations, body weights, body weight gains, quantitative food consumption, ophthalmology, functional observational battery (CNS) observations, cardiovascular endpoints, respiratory endpoints, hematology, urinalysis, gross pathology, and organ weights 28-day toxicology studies. At the end of the dosing phase, there were significant dose-related increases in alkaline phosphatase (ALP) activity, an anticipated pharmacology effect in rats or monkeys. No noteworthy systemic organ toxicities were observed in rats or monkeys at any of the doses evaluated in respective studies.

ALP201 was well tolerated locally following SC administration to rats and monkeys. Non-adverse ALP201-related microscopic changes in monkey study were confined to the injection sites and included minimal to mild degeneration/necrosis in males and females. Degeneration/necrosis and mixed cell inflammation/infiltration of the injection site(s) were of lower incidence and severity or had features of chronicity (mineralization) within the recovery group, indicating partial recovery. Non-adverse microscopic changes in rat study were limited to the injection procedures with associated reactive changes in the draining lymph nodes. There was no discernible ALP201-associated alteration in the incidence, severity, or microscopic character of the changes at the injection sites or draining lymph nodes. Microscopic changes in the injection sites and draining lymph nodes of recovery animals were similar to those noted in the terminal necropsy animals, although less pronounced in the recovery group animals.

The observed exposure of the NOAEL at 20 mg/kg/dose from the GLP SC monkey toxicity study is approximately 113× (for IV) and 83× (for SC) higher than the projected AUC exposure of the proposed human starting single dose of 15 mg IV or 15 mg qw×3 SC (Table 18). Given the safety margin and the lack of systemic toxicity or local tolerability findings in the 28-day rat and monkey toxicology studies with ALP201, the safety risk for humans on the 15 mg starting dose is very low.

Immunogenicity

Immunogenicity potential of ALP201 was evaluated by measuring ALP201 Anti-drug antibodies (ADA) in serum collected from the GLP rat and monkey 28-day toxicology studies.

In the rat toxicity study, the ADA responses were positive with SC administration in 9 of 20 (6 males; 3 females) animals from the control group, 10 of 19 (6 males; 4 females) animals at 2 mg/kg/dose, 12 of 20 animals (7 males; 5 females) at 10 mg/kg/dose and 12 of 20 animals (6 males; 6 females) at 30 mg/kg/dose on PK Day 28. Additionally, the ADA responses were positive with single dose IV ALP201 administration in 14 of 20 animals (8 males; 6 females) at 10 mg/kg on PK Day 28. The positive ADA response did not appear to consistently impact the composite plasma concentration-time profiles of the 2 and 10 mg/kg/dose SC dose groups on Day 24 although the ADA may have contributed to the apparent decrease of systemic exposure at 30 mg/kg/dose on Day 24. The positive ADA responses in control animals are unlikely to be due to ALP201 mis-dosing based on the investigation conducted. A dose-dependent increase in ALP, an expected pharmacological effect of ALP201, was observed for the mg/kg SC dose groups prior to terminal necropsy, which were resolved at recovery necropsy. The ALP results of animals in the control groups were similar prior to both terminal and recovery necropsy. Moreover, there were no ALP201-related in-life findings during the dosing and recovery phase. Therefore, taken collectively, the positive ADA responses observed in the control animals on PK Days 28 and 56 (study dates Day 29 and Day 57) were mostly likely due to a blood collection contamination and were not considered to have an impact on the study.

In the monkey toxicity study, the anti-ALP201 antibodies responses were negative for all pre-dose samples on Day 0. The ADA responses were positive in 4 of 10 animals at 1 mg/kg/dose, 6 of 10 animals at 5 mg/kg/dose, and 5 of 10 animals at 20 mg/kg/dose on Day 28. Although a direct correlation could not be made between positive ADA responses and systemic exposure concentration-time profiles as ADA samples were not sampled on TK collection days, following multiple doses, the concentration-time profiles for some of the animals at mg/kg appeared to be impacted by anti-ALP201 antibodies. The animals impacted by anti-ALP201 antibodies were 3 animals (2 males and 1 female) at 1 mg/kg/dose, and 3 animals at 5 mg/kg/dose (3 females), with the days of impact on concentration-time profiles ranging from Day 18 to Day 24 for these animals.

Example 2

The pharmacokinetic profile of asfotase alfa in multiple species suggests that a combination of reduced absolute bioavailability and half-life necessitates frequent dosing. The catalytic domain of human TNSALP is a highly glycosylated molecule. The presence of asialylated glycans leads to clearance via the asialoglycoprotein receptor (ASGPR) in the liver.

ALP201 was developed as a Next Generation alkaline phosphatase ERT with these considerations in mind. ALP201 retains the TNSALP-IgG Fc-D10 architecture used in asfotase alfa and incorporates the removal of two non-essential N-linked glycans, a change in the human Fc isotype to IgG2/4, and numerous process improvements in the expression of the molecule that lead to higher TSAC incorporation. In this report, we present the pharmacokinetic parameters for ALP201 determined in single dose studies of male C57BL/6 mice by intravenous and subcutaneous administration. We also report the PK parameters of multiple lots of ALP201 expressed and purified with varying levels of TSAC incorporation to help determine which PK parameters are most strongly affected by asialylated glycan clearance.

Materials and Methods

Animal Strain

To maintain consistency between these studies and previous pharmacokinetic studies performed on asfotase alfa, this study was performed using male C57BL/6 mice aged approximately 11-12 weeks at the time of dosing. The information for the test molecules is shown in Table 19.

TABLE 19

Test Articles

| Molecule | Lot # | Specific Activity* | Total Sialic Acid Content (mol/monomer) | Concentration (mg/mL) | Formulation |
|---|---|---|---|---|---|
| ALP201 | 1 | 36.9 | 5.9 | 8.35 | PBS |
| ALP201 | 2 | 32.8 | 5.9 | 9.15 | PBS |
| ALP201 | 3 | 40.3 | 5.0 | 3.09 | PBS |
| ALP201 | 4 | 39.1 | 3.2 | 6.54 | PBS |

*Specific activity listed in U/mg of 4-MUP hydrolysis, where 1 U = enzyme needed to hydrolyze 1 micromole of 4-MUP in 1 minute under assay buffer conditions at 37° C.

Animal Dosing and Blood Sampling

Animals from 11-12 weeks of age were randomized by body weight and assigned to 4 groups. A 4 mg/kg dose of ALP201 was administered to 16 mice/group on day 0 by intravenous delivery (IV) (Group 1) or subcutaneously (SC) (Group 2). An equivalent weight-adjusted volume of PBS was administered on day 0 to 4 mice/group by IV (Group 3) or SC (Group 4). IV dosing was administered via tail vein. SC bolus dosing was administered in the scapular region above the shoulders.

A semi-serial sampling design was used, with 4 cohorts per group and n=4/per cohort+1 extra mouse per group. In the study run at Alexion, each mouse was bled 3 times, including the terminal bleed. Time-points (hours post-dose) are shown in Table 20 below for each cohort.

For non-terminal bleeds, 100 mL of whole blood was collected via submandibular collection into pre-coated lithium heparinized tubes to collect at least 50 µL of plasma per time point for each animal. At the terminal bleed, as much blood was collected as possible via cardiac puncture into lithium heparinized collection tubes. Blood was kept at 4° C. and processed for plasma by centrifugation as soon as feasible after collection. Each plasma sample was split into 2 equal volume aliquots prior to snap-freezing in $CO_2$/ethanol and storage at −80° C.

TABLE 20

Experimental Treatment Groups, Dose, Route of Administration and Blood Sampling Schedule for In House Study

| Group | No. of Mice | Test Article | Route | Dose (mg/kg) | Dose Conc. (mg/mL) | Dose (mL/kg) | Vehicle |
|---|---|---|---|---|---|---|---|
| 1 | 16 + 1[a] | ALP201 | IV bolus | 4 | 1 | 4 | PBS-without Ca/Mg |
| 2 | 16 + 1[a] | ALP201 | SC bolus | 4 | 1 | 4 | PBS-without Ca/Mg |
| 3 | 4 | PBS | IV bolus | — | — | — | — |
| 4 | 4 | PBS | SC bolus | — | — | — | — |

[a]N = 16 per group + 1 extra, which is used as a replacement animal in case of animal death or mis-dose

TABLE 21

Blood Sampling Schedule for In House Study, Cohorts of Groups 1 and 2

| Cohort | 0.25 h | 1 h | 6 h | 24 h (D1) | 48 h (D2) | 72 h (D3) | 96 h (D4) | 120 h (D5) | 192 h (D8) | 264 h (D11) | 336 h (D14) | 480 h (D21) |
|---|---|---|---|---|---|---|---|---|---|---|---|---|
| 1 | X | | | | | X | | | | X | | |
| 2 | | X | | | X | | | X | | | | | |
| 3 | | | X | | | | X | | | | X | | |
| 4 | | | | X | | | | X | | | | | X |

TABLE 22

Blood sampling Schedule for In House Study, Groups 3 and 4

| Group | 0.25 h | 1 h | 6 h | 24 h (D1) | 48 h (D2) | 72 h (D3) | 96 h (D4) | 120 h (D5) | 192 h (D8) | 264 h (D11) | 336 h (D14) | 480 h (D21) |
|---|---|---|---|---|---|---|---|---|---|---|---|---|
| 3 | X | | | | | | | | X | | | |
| 4 | X | | | | | | | | X | | | |

For lots 2, 3, and 4, groups of 32 mice were assembled for each route of administration into 8 cohorts of 4 animals/timepoint. In groups with IV administration, each cohort was bled twice (the first time point as a survival collection, and the second terminally) at approximately 0.5, 1, 3, 8, 12, 21, 26, 32, 45, 49, 72, 96, 120, 192, 264, and 336 hours post-dose. In groups of SC administration, each cohort was bled twice (the first as a survival collection, and the second terminally) at approximately 1, 3, 6, 8, 12, 21, 26, 32, 45, 49, 72, 96, 120, 192, 264, and 336 hours post-dose.

Determination of Active ALP201 Concentration in Plasma

Plasma samples were assayed for alkaline phosphatase activity using 4-methylumbelliferyl phosphate (4-MUP) as an artificial substrate. Hydrolysis of the phosphoester bond in 4-MUP releases the fluorescent compound 4-methylumbelliferone (4-MU), which is easily detected by a fluorimeter. Activity quantitation was performed via an enzyme activity standard curve.

Sample Analysis for in House PK Study

Activity quantitation was performed via an enzyme activity standard curve created using serial dilutions of an asfotase alfa protein reference standard with known activity in the 4-MUP assay on the same plate. Thawed plasma samples were diluted 100-fold to 2,000-fold into assay buffer (50 mM HEPES, 150 mM NaCl, 1 mM $MgCl_2$, pH 7.4 and 1 mg/mL BSA) and assayed to determine active ALP201 enzyme concentration. Final protein standard range on each plate was from 4-80 ng/mL.

The diluted samples were quantitated as follows: all diluted samples were brought to 37° C. prior to initiation of the assay by addition of 4-MUP to the protein sample, resulting in a final concentration of 10 mM 4-MUP. Production of 4-MU was measured at an excitation wavelength of 360 nm and an emission wavelength of 465 nm. Data was collected in a plate reader held at 37° C., with the plate read every 40 seconds for a total of 20 minutes. Rates of reaction for plasma and standard samples were calculated by linear regression of the reaction slope using Microsoft Excel in units of relative fluorescence units (RFU) per minute. Rates of reaction for standard samples were used to construct linear standard curve units in RFU/min/U. Comparison of measured rates of reaction in plasma samples were compared with the standard curve to determine plasma activity of ALP201 in U/mL. Sample activities in Units/mL were converted to mass units of mg/L by dividing the sample activities by the specific activity of the tested protein sample (in U/mg). Samples were run in duplicate twice to compile data for each independent sampling point.

Sample Analysis for PK Studies

The same 4-MUP hydrolysis assay was performed. On the day of the assay, standards, quality controls (QCs), dilution controls (DCs), and blanks were diluted 250-fold in assay buffer. Standards, QCs, DCs, and blanks were further diluted 2-fold with the substrate, 4-Methylumbelliferyl phosphate (4-MUP), for the total 500-fold minimum required dilution (MRD). Prior to performing the MRD, the DC was diluted 200-fold in mouse plasma. ALP201 was quantified based on the fluorescent product methylumbelliferone, which results from the hydrolysis of 4-MUP substrate used in the assay. The plate was placed in a plate reader and read once every 60 seconds with kinetic fluorescence settings at 360 nm (excitation), 455 nm (cutoff), and 465 nm (emission) for 25 minutes at 37° C. The enzyme activity was directly proportional to the rate of the substrate reaction. The Vmax (rate in fluorescence intensity/min) was determined from a line of best fit through the data. The blank was not included in the curve fit. Results were reported in mg/L. Values were corrected for differences in specific activity between the test article and the protein activity standard.

Pharmacokinetic Analysis

The PK analysis was performed using Phoenix WinNonlin v8.0 (Certara). Pharmacokinetic parameters were calculated using a noncompartmental analysis.

The following noncompartmental PK parameters were calculated: area under the concentration-time curve from time zero (dosing) to the last detectable concentration ($AUC_t$), dose-normalized area under the concentration-time curve from time zero (dosing) to the last detectable concentration ($AUC_t$/dose), area under the concentration-time curve from time zero (dosing) extrapolated to infinity ($AUC_{inf}$), dose-normalized area under the concentration-time curve from time zero (dosing) extrapolated to infinity ($AUC_{inf}$/dose), maximum observed plasma concentration ($C_{max}$), dose-normalized maximum observed plasma concentration ($C_{max}$/dose), time of maximum observed plasma concentration ($T_{max}$), terminal elimination half-life ($t_{1/2}$), total clearance (CL), apparent volume of distribution ($V_d$), and bioavailability (F). Actual sample collection times were used to calculate PK parameters. Actual doses were used to calculate dose-normalized PK parameters.

Results and Discussion

Pharmacokinetic Parameters of ALP201 Following IV and SC Administration in Mice

The PK of ALP201 was evaluated following single IV or SC administration to male C57BL/6 mice. 16 mice were dosed in each group, and blood was collected from subdivided cohorts of 4 mice within each group at the following time points post-administration: 0.25, 1, 6, 24, 48, 72, 96, 120, 192, 264, 336, and 480 hours.

Plasma ALP201 concentrations were measured using an enzymatic activity assay, which measured alkaline phosphatase catalytic activity of ALP201. The enzymatic activity of ALP201 was then converted to mass unit (mg/L) for reporting.

Figure 8B:
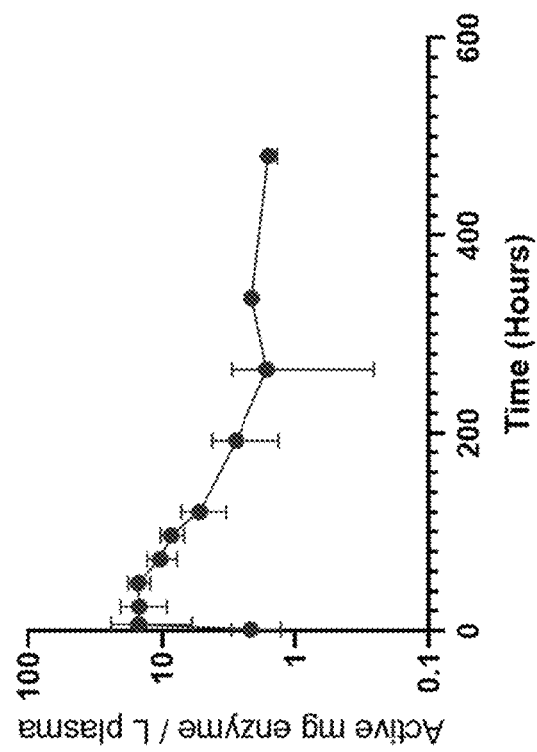
FIGS. 8A and 8B are graphs showing mean (SD) ALP201 active plasma concentration versus time profiles following intravenous (FIG. 8A) and subcutaneous (FIG. 8B) administration to male C57BL/6 mice.
Figure 8A:
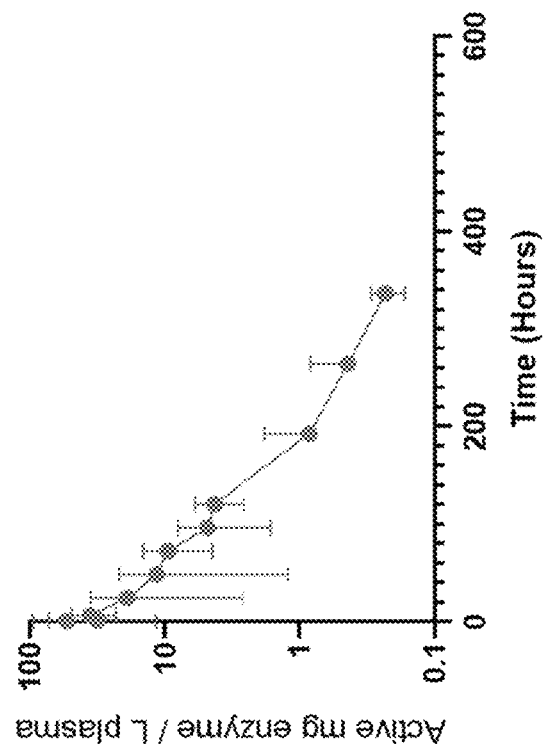
Figure 9A:
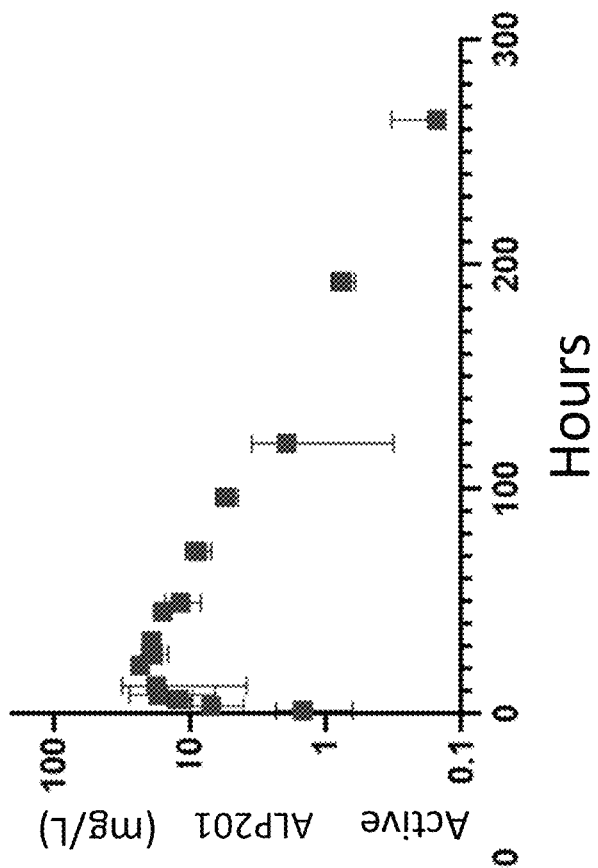
FIGS. 9A and 9B are graphs showing mean (SD) ALP201 active plasma concentration versus time profiles for ALP201 (lot with TSAC=5.9) following intravenous (FIG. 9A) and subcutaneous (FIG. 9B) administration to male C57Bl/6 mice.
Figure 9B:
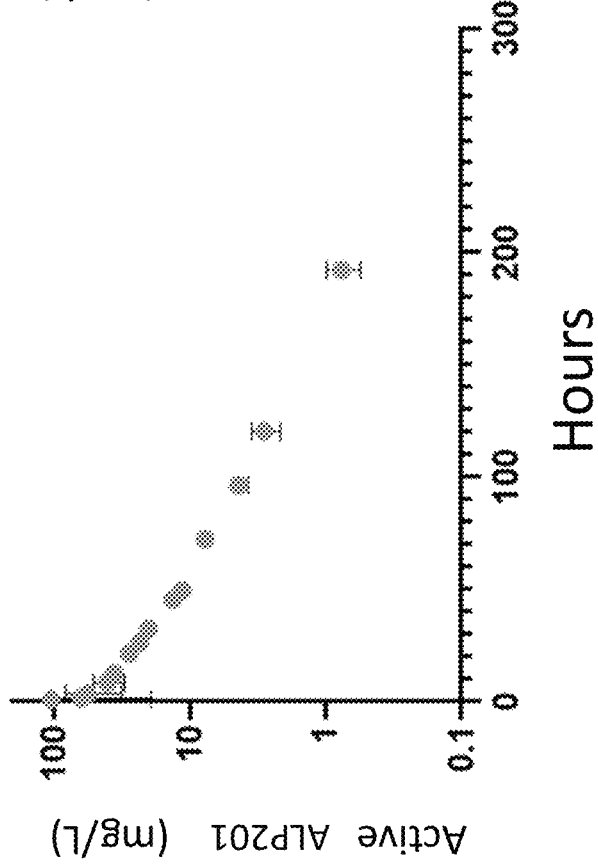
Figures 10A, 10B:
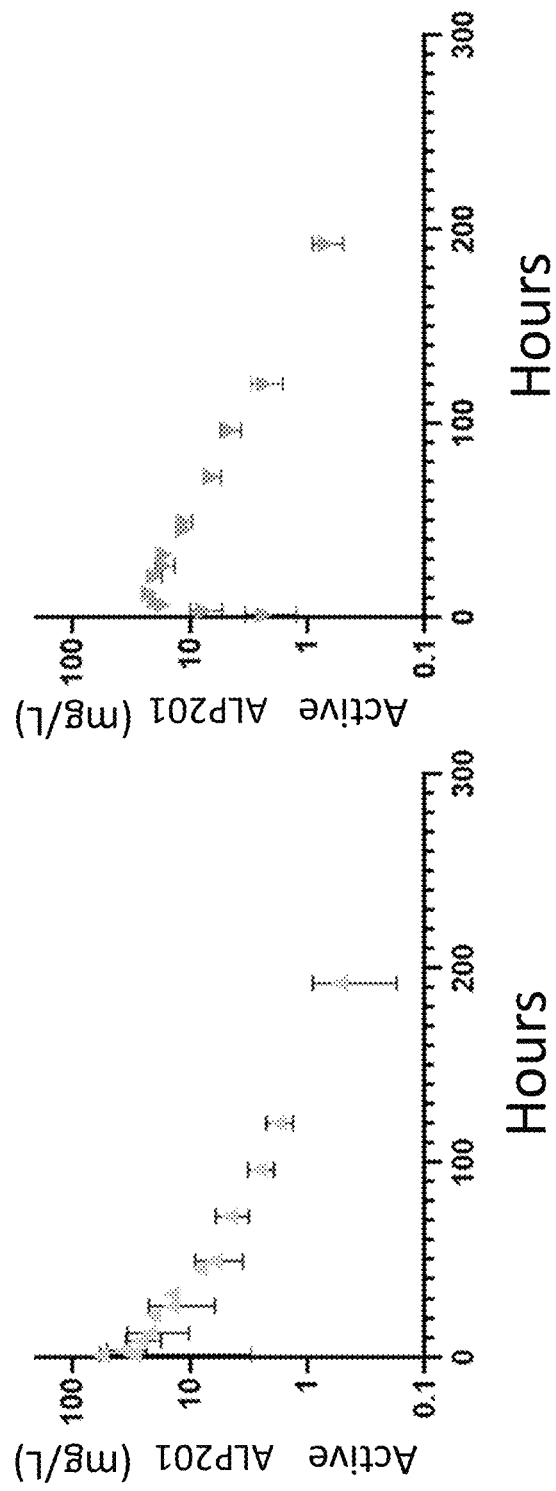
FIGS. 10A and 10B are graphs showing mean (SD) ALP201 active plasma concentration versus time profiles for ALP201 (lot with TSAC=5.0) following intravenous (FIG. 10A) and subcutaneous (FIG. 10B) administration to male C57Bl/6 mice.
Figure 11A:
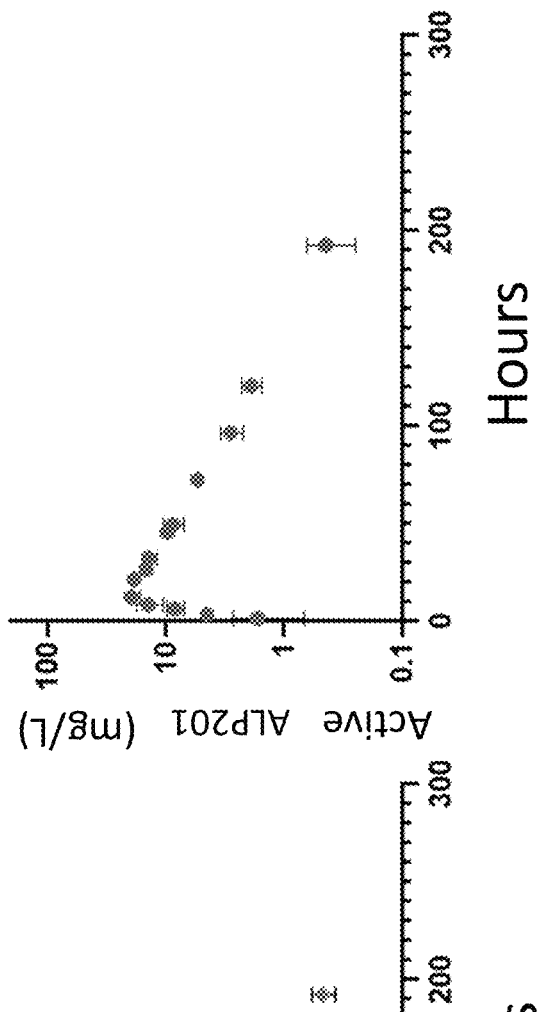
FIGS. 11A and 11B are graphs showing mean (SD) ALP201 active plasma concentration versus time profiles for ALP201 (lot with TSAC=3.2) following intravenous (FIG. 11A) and subcutaneous (FIG. 11B) administration to male C57Bl/6 mice.
Figure 11B:
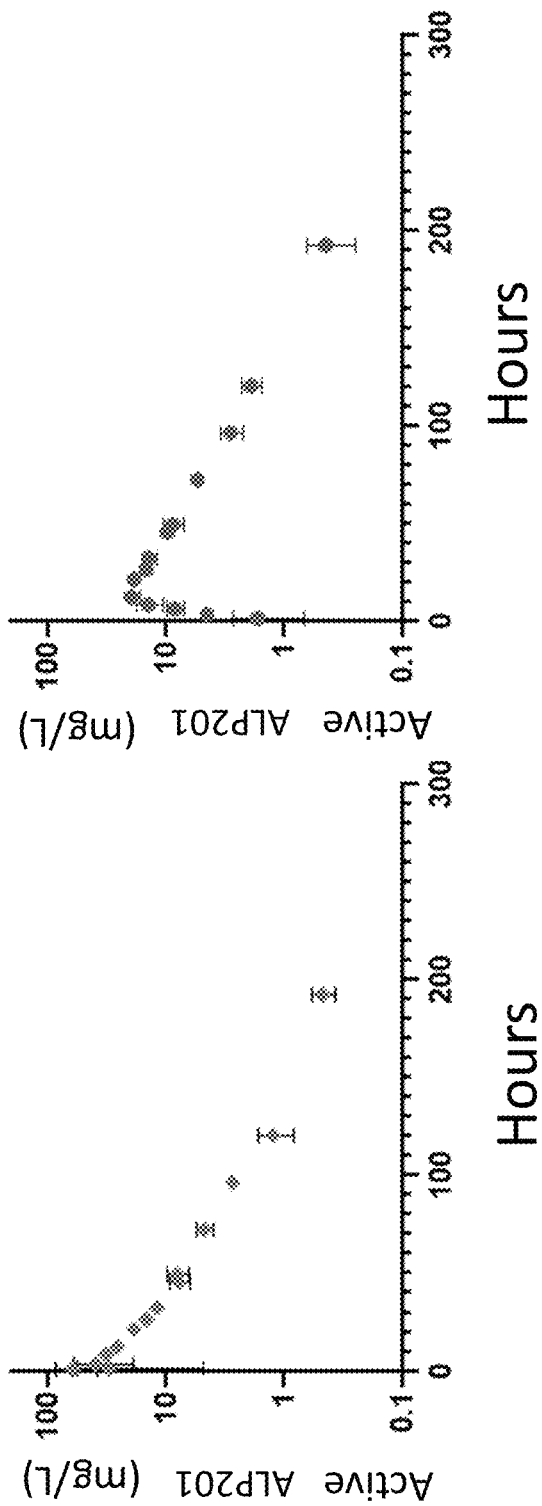

The mean active ALP201 plasma concentration versus time profiles following IV and SC administration are presented on semi-log scale in FIGS. 8A and 8B. PK parameters of ALP201 are summarized in Tables 7 and 11 above.

Individual mouse plasma activity profiles from some mice in the IV group appear to suggest that some of the dose may have been delivered subcutaneously, which may be responsible for the relatively high variability observed in early time points of the IV dosing profile. If this occurred, the calculated value of $C_{max}$ for the IV dosed group may also be artificially low. After IV administration, the concentration-time profile declined in a multi-exponential manner (FIGS. 8A and 8B). The CL was 0.0019 L/h/kg and the apparent terminal t½ was 48 hours. After SC administration, the time to reach maximum concentration ($t_{max}$) was 48 hours post-dose, suggesting relatively slow absorption from the SC injection site. Absolute bioavailability following SC administration was 96%.

Pharmacokinetic Parameters of ALP201 Lots with Varying Total Sialic Acid Content Values in Mice Three separate lots of ALP201, purified with measured TSAC values of 5.9, 5.0, and 3.2 moles sialic acid/mol of protein monomer, were dosed by IV and SC administration into 32 mice. Blood was collected from subdivided cohorts of 4 mice within each administration group at the following time points post-administration: 0.5, 1, 3, 8, 12, 21, 26, 32, 45, 49, 72, 96, 120, 192, 264, and 336 hours post dose for IV administration; and 1, 3, 6, 8, 12, 21, 26, 32, 45, 49, 72, 96, 120, 192, 264, and 336 hours post dose for SC administration with each mouse bled twice.

Plasma ALP201 concentrations were measured using an assay, which measured alkaline phosphatase catalytic activity of ALP201. The enzymatic activity of ALP201 was reported in mass units (mg/L) by Charles River.

Figure 12:
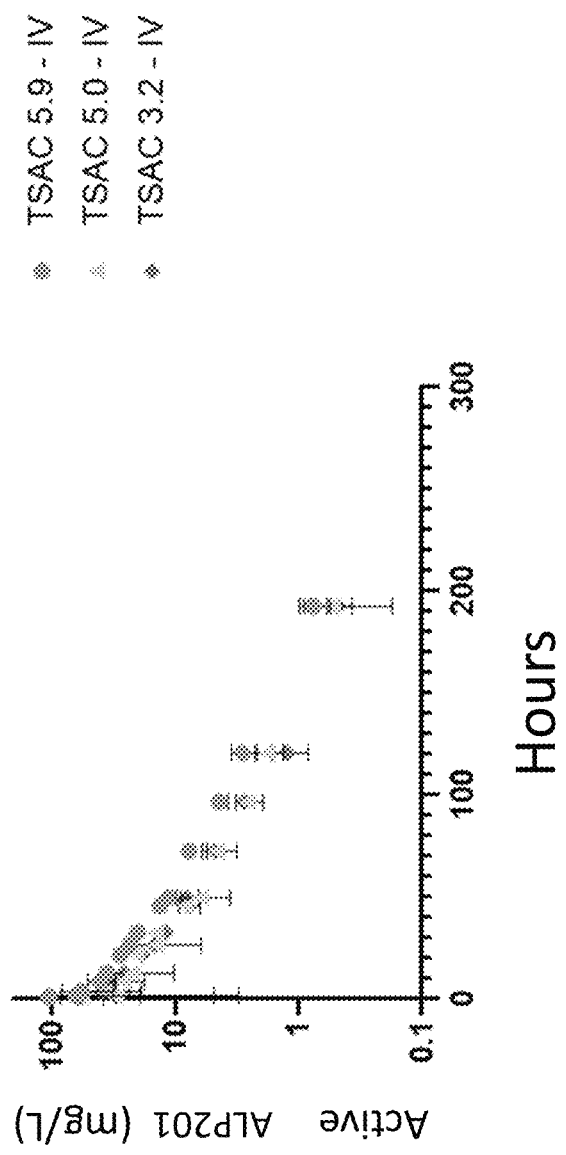
FIG. 12 is a graph showing mean (SD) ALP201 active plasma concentration versus time profiles for ALP201 TSAC values (3.2, 5.0, and 5.9) following intravenous administration to male C57BL/6 mice.
Figure 13:
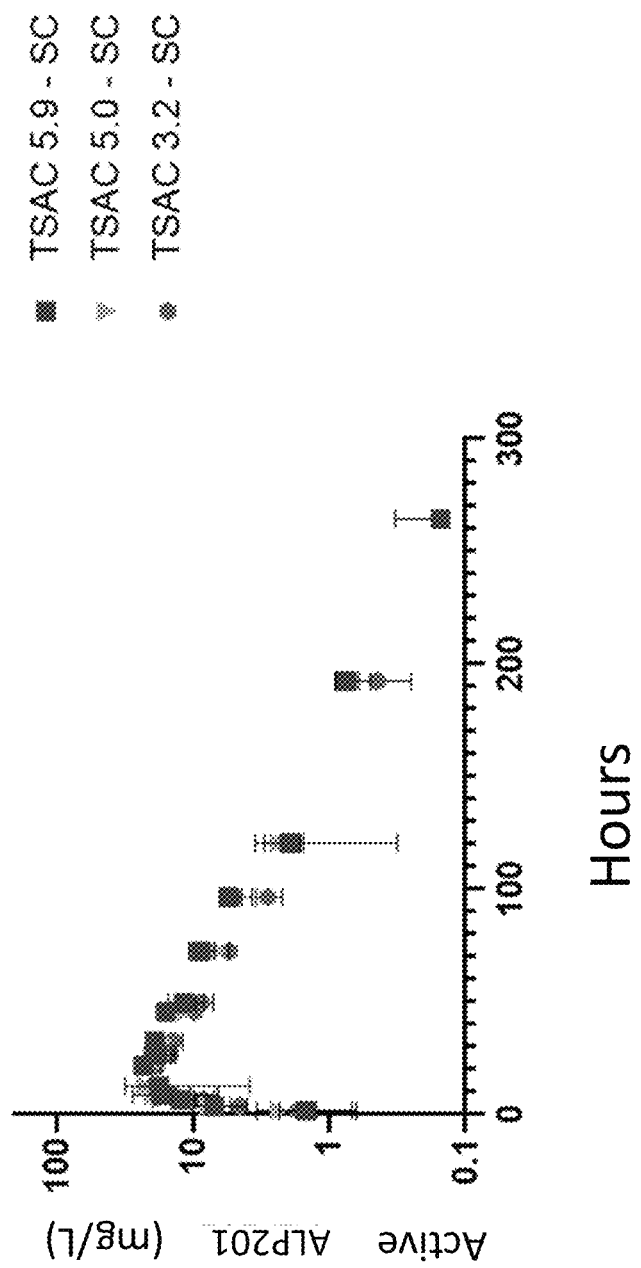
FIG. 13 is a graph showing mean (SD) ALP201 active plasma concentration versus time profiles for ALP201 TSAC variants following subcutaneous administration to male C57BL/6 mice.

The mean active ALP201 plasma concentration versus time profiles following IV and SC administration for each protein lot are presented on semi-log scale in FIGS. 9A and 9B, 10A and 10B, and 11A and 11B. A collection of the plasma concentration versus time profiles for IV administration of the TSAC value variants is presented in FIG. 12. A collection of the plasma concentration versus time profiles for SC administration is presented in FIG. 13. Tabulated summaries of mean PK parameters and mean dose normalized PK parameters following IV and SC administration can be found in Tables 21 and 22 respectively.

TABLE 23

Summary of ALP201 Pharmacokinetic Parameters For TSAC Value Variants Following Subcutaneous Administration in Male C57BL/6 Mice

| TSAC (mol/mol) | Route | Dose (mg/kg) | $C_{max}$ (mg/L) | $t_{max}$ (h) | $t_{1/2}$ (h) | $AUC_t$ (mg * h/L) | $AUC_\infty$ (mg * h/L) | $V_d$ or $V_d$/F (L/kg) | CL or CL/F (L/h/kg) | F (%) |
|---|---|---|---|---|---|---|---|---|---|---|
| 5.9 | IV | 4 | 105.3 | 0.5 | 29.9 | 2060.5 | 2063.8 | 0.08 | 0.0019 | NA |
| 5.9 | SC | 4 | 23.3 | 21 | 33.4 | 1480.3 | 1487.6 | 0.13 | 0.0027 | 72.1 |
| 5.0 | IV | 4 | 57.3 | 0.5 | 31.4 | 1319.6 | 1322.4 | 0.14 | 0.0030 | NA |
| 5.0 | SC | 4 | 22.4 | 12 | 34.9 | 1316.5 | 1351.4 | 0.15 | 0.0030 | 102.2 |
| 3.2 | IV | 4 | 61.4 | 0.5 | 32.8 | 1308.1 | 1330.4 | 0.14 | 0.0030 | NA |
| 3.2 | SC | 4 | 19.7 | 12 | 35.6 | 1058.7 | 1081.5 | 0.19 | 0.0037 | 81.3 |

Abbreviations:
$AUC_\infty$ = area under the concentration time curve from time zero (dosing) extrapolated to infinity;
$AUC_t$ = area under the concentration time curve from time zero (dosing) to the last detectable concentration;
CL or CL/F = total clearance;
$C_{max}$ = maximum observed plasma concentration;
F = absolute bioavailability;
IV = intravenous;
NA = not applicable;
SC = subcutaneous;
TSAC = total sialic acid content;
$t_{max}$ = time to maximum observed plasma concentration;
$t_{1/2}$ = terminal elimination half-life;
$V_d$ or $V_d$/F = apparent volume of distribution.

TABLE 24

Summary of Dose Normalized ALP201 Pharmacokinetic Parameters For TSAC Value Variants Following Subcutaneous Administration in Male C57BL/6 Mice

| TSAC (mol/mol) | Route | $C_{max}$/dose [(mg/L)/(mg/kg)] | $AUC_t$/dose [(mg * h/L)/(mg/kg)] | $AUC_\infty$/dose [(mg * h/L)/(mg/kg)] |
|---|---|---|---|---|
| 5.9 | IV | 26.3 | 515.1 | 516.0 |
| 5.9 | SC | 5.8 | 371.1 | 371.9 |
| 5.0 | IV | 14.3 | 329.9 | 330.6 |
| 5.0 | SC | 5.6 | 329.1 | 337.9 |
| 3.2 | IV | 15.4 | 327.0 | 332.6 |
| 3.2 | SC | 4.9 | 264.7 | 270.4 |

Abbreviations:
$AUC_{inf}$/dose = dose normalized area under the concentration time curve from time zero (dosing) extrapolated to infinity;
$AUC_t$/dose = dose normalized area under the concentration time curve from time zero (dosing) to the last detectable concentration;
$C_{max}$/dose = dose normalized maximum observed plasma concentration;
IV = intravenous;
SC = subcutaneous;
TSAC = total sialic acid content ALP201 protein lots with TSAC values of 5.9, 5.0, and 3.2 mol/mol, correspond to 1.48, 1.25, and 0.80 moles of sialic acid per consensus N-linked glycan site, and the PK profiles of all lots (for both IV and SC administration) were similar in shape, with similar $T_{max}$ and $t_{1/2}$ values. With increasing TSAC value, clearance slightly decreased, $C_{max}$ and AUC by both IV and SC routes increased, and volume of distribution decreased. All of these changes are consistent with the idea that lower TSAC values lead to higher levels of immature N-linked glycans, which can be quickly cleared by cellular receptors like ASGPR and cause higher clearance, lower $C_{max}$ and lower AUC for a protein sample. Changes in these parameters are relatively small, and maximally differ by 2-fold at most.

Comparison of ALP201 PK Parameters in Mice with Asfotase Alfa PK Parameters in Mice As a second-generation alkaline phosphatase ERT, ALP201 was designed to improve upon the PK parameters of asfotase alfa, which was previously tested in mouse PK studies using male C57BL/6 mice. A summary of the PK parameters for asfotase alfa is presented in Table 25.

TABLE 25

Previously Determined Pharmacokinetic Parameters of Asfotase Alfa
in C57BL/6 mice after a Single IV or SC Administration at 2 mg/kg

| Route | $C_{max}$ (mg/L) | Cmax/dose [(mg/L)/(mg/kg)] | $t_{1/2}$ (h) | $AUC_{t\,(0\text{-}49)}$ (mg * h/L) | $AUC_\infty$ (mg * h/L) | $AUC_\infty$/dose [(mg * h/L)/(mg/kg)] | CL (L/h/kg) | F (%) |
|---|---|---|---|---|---|---|---|---|
| IV | 26.4 | 13.2 | 15.6 | 258 | 286 | 143 | 0.007 | NA |
| SC | 3.07 | 1.54 | 31.1 | 100 | 161 | 81 | ND | 38.8 |

Abbreviations:
$AUC_\infty$ = area under the concentration time curve from time zero (dosing) extrapolated to infinity;
$AUC_t$ = area under the concentration time curve from time zero (dosing) to the last detectable concentration;
CL = total clearance;
$C_{max}$ = maximum observed plasma concentration;
F = absolute bioavailability;
IV = intravenous;
SC = subcutaneous;
$t_{1/2}$ = terminal elimination half-life In all PK data sets collected for ALP201 in male C57BL/6 mice, ALP201 demonstrates superior in vivo half-life (as measured by t112), in vivo exposure (as measured by $C_{max}$ and AUC), and bioavailability. For all tested samples, ALP201 also demonstrates significantly lower clearance in mice than asfotase alfa.

Because asfotase alfa release specifications limit the molecule to TSAC values of 1.2-3.0 mol/mol and the molecule has 6 N-linked glycosylation sites per monomer, sialic acid incorporation for asfotase alfa is only 0.20-0.50 moles sialic acid/glycan. This indicates that many glycans on asfotase alfa contain no sialic acid moieties and could be efficient substrates for ASPGR clearance. This could explain the higher clearance, and lower dose normalized $C_{max}$ and AUC observed for asfotase alfa relative to ALP201.

These samples of ALP201 all have much higher bioavailability than asfotase alfa, with the least bioavailable sample of ALP201 having roughly double the observed bioavailability of asfotase alfa (72.1% vs. 38.8%). Differences in the human IgG Fc domain isotype between the two constructs may be the cause of this observation. We have shown that the IgG2/4 Fc domain of ALP201 does not bind to a panel of common Fcg receptors, but the IgG1 Fc domain of asfotase alfa does bind strongly to at least two of them (Source: Research Technical Report 036). If these Fcg receptors are present in the subcutaneous space, asfotase alfa may be cleared before it even enters systemic circulation, lowering bioavailability and exposure.

Conclusion

The findings from these studies indicate that ALP201 has a significantly improved dose-adjusted pharmacokinetic profile in mice relative to asfotase alfa following either IV or SC administration, with higher bioavailability, dose-normalized $C_{max}$ and dose-normalized exposure. Additional PK studies using ALP201 samples with varying levels of TSAC incorporation indicated small increases in $C_{max}$ and in vivo exposure with increased TSAC levels. Elimination half-life, $T_{max}$, and bioavailability appeared to be relatively unaffected by changes in TSAC values.

Example 3

Overview of Single Dose PK Studies with ALP201

Two single dose PK studies were conducted as part of the asfotase alfa non-clinical development program, in Sprague-Dawley rat and Cynomolgus monkey, respectively (Table 26). These studies supported ALP201 single dose studies.

TABLE 26

Single Dose PK Studies Conducted with Asfotase Alfa

| Name of Study | Duration | Species | Route of Administration | Formulation |
|---|---|---|---|---|
| Single dose PK | 3 days | Rat | IV, SC | 25 mM sodium phosphate pH 7.4, 150 mM sodium chloride |
| Single dose PK | 3 days | Monkey | IV, SC | 25 mM sodium phosphate pH 7.4, 150 mM sodium chloride |

Note:
Unless otherwise stated, PK/TK parameters were characterized by the non-compartmental analysis (NCA) method.
Abbreviations:
IV = intravenous;
PK = pharmacokinetics;
SC = subcutaneous;
TK = toxicokinetics.

Following single dose IV administration, systemic clearance (CL) of asfotase alfa ranged from 0.0193-0.0492 L/h/kg with apparent half-life ranging from 27-34 hours. Volume of distribution at steady state ($V_{ss}$) ranged from 0.432-1.39 L/kg. Following single SC administration to rats and monkeys, the time to reach maximum concentration ($T_{max}$) ranged from 10-32 hours post-dosing, suggesting slow absorption of asfotase alfa from the SC injection site. The estimated bioavailability for the SC route of administration ranged from 26%-35% in rats and monkeys.

Conclusions from Single Dose PK Studies

ALP201 has been designed to improve upon the characteristics of the approved product, asfotase alfa, with improved efficacy/activity, systemic exposure, absolute bioavailability, and half-life. The Ig Fc domain isotype in ALP201 is G2/4 instead of the IgG1 Fc domain present in asfotase alfa. This alteration is designed to improve ALP201's pharmacokinetic properties including systemic PK exposure, half-life, and bioavailability.

Preclinical data from 3 animal species (mouse, rat, and monkey) provide supportive evidence that these objectives have been achieved. In comparison to asfotase alfa, ALP201 has demonstrated significant improvement in PK exposure (>10-fold), absolute bioavailability (2-fold), and half-life (2-fold) following IV/SC administration in 3 animal species. Preclinical population PK modeling also predicts that improved ALP201 PK properties are expected to extrapolate to human, which will facilitate treatment of patients with reduced injection volume, less frequent administration, and lower total amount on an annual basis, thereby reducing the burden of treatment for patients.

Nonclinical Safety Studies

Summary of Toxicology Studies to Support First-in-Human Study

Standalone single dose toxicology/tolerability studies were not conducted for ALP201. ALP201 doses for repeated dose definitive (GLP) toxicology studies were selected based on the data obtained from ALP201 single dose IV and SC PK studies in rats and monkeys. The tolerability of ALP201 was assessed in the single dose IV and SC PK studies in rats and monkeys by clinical observations, including site of injection reactions and clinical pathology data. In summary, ALP201 was well tolerated when a single dose was administered via either IV or SC in rats up to 27 mg/kg and in monkeys up to 20 mg/kg.

Definitive GLP-compliant ALP201 28-day toxicity studies in cynomolgus monkeys and Sprague-Dawley rats are ongoing. The in-life portion of rat and monkey studies, including the recovery phases, are complete and the reports are being prepared. Although audited draft reports of these studies are not yet available, all data from both studies except ADA data are available and the findings are summarized in Table 27. In summary, the results from ALP201 28-day toxicity studies in rats and monkeys indicate that ALP201 treatment did not result in any noteworthy/biologically meaningful treatment-related adverse effects from any of the toxicity endpoints evaluated in both the studies, including safety pharmacology endpoints.

TABLE 27

Comparison of Findings from ALP201 Rat and Monkey 28-Day GLP Toxicity Studies

|  | ALP201 Monkey GLP Toxicity Study[a] | ALP201 Rat GLP Toxicity Study[a] |
|---|---|---|
| Age of Animals | Approximately 2-3 years | Approximately 7-8 weeks |
| Duration of Study | 28-Days | 28-Days |
| Recovery Period | 28-Days | 28-Days |
| Route of Administration | Subcutaneous injection | Subcutaneous injection[b] |
| Frequency of Administration | Once every 3 days (Q3D) | Once every 3 days (Q3D) |
| Total number of doses administered | 10 doses | 10 doses |
| Doses administered | 0, 1, 5, or 20 mg/kg/dose | 0, 2, 10, or 30 mg/kg/dose |
| NOAEL | 20 mg/kg/dose | 30 mg/kg/dose |
| $AUC_{0-t}{}^c$ at NOAEL | Day 1: 27,900 µg · hr/mL Day 24: 36,800 µg · hr/mL | Day 1: 11,600 µg · hr/mL Day 24: 4,380 µg · hr/mL |
| $C_{max}$ at NOAEL[c] | Day 1: 125 µg/mL Day 24: 254 µg/mL | Day 1: 79.9 µg/mL Day 24: 43.9 µg/mL |
| Mortality | No mortality | No mortality |
| Clinical Observations | No treatment-related clinical observations | No treatment-related clinical observations |
| Body Weight | No treatment-related findings | No treatment-related findings |
| Food Consumption | No treatment-related findings | No treatment-related findings |
| Ophthalmology | No treatment-related findings | No treatment-related findings |
| Dermal Observations | No treatment-related findings at site of injections | No treatment-related findings at site of injections |
| ECG | No treatment-related findings based on quantitative parameters (heart rate, RR interval, PR interval, QRS duration, QT interval, and QTc interval) and qualitative review of the ECG | NA |
| Blood Pressure | No treatment-related findings | NA |
| Respiratory | No treatment-related findings | No treatment-related findings |
| CNS | NA | No treatment-related findings |
| Clinical Pathology Parameters | | |
| Hematology | No treatment-related findings | No treatment-related findings |
| Coagulation | No treatment-related findings | No treatment-related findings |
| Clinical Chemistry | No treatment-related findings apart from dose dependent increases in ALP levels, an expected pharmacological effect | No treatment-related findings apart from dose dependent increases in ALP levels, an expected pharmacological effect |
| Urinalysis | No treatment-related findings | No treatment-related findings |
| Organ Weights | No treatment-related findings | No treatment-related findings |
| Macroscopic Findings | No treatment-related findings | No treatment-related findings |
| Anatomic Pathology | Slight degeneration/necrosis and mineralization of injection sites were observed; but were concluded to be non-adverse. These findings were partially recovered at the end of recovery. | Sporadic injection site findings with associated reactive changes in the draining lymph nodes; these findings were not dose dependent and were concluded to be non-adverse; these findings were partially reversed at the |

TABLE 27-continued

Comparison of Findings from ALP201 Rat and Monkey 28-Day GLP Toxicity Studies

| | ALP201 Monkey GLP Toxicity Study[a] | ALP201 Rat GLP Toxicity Study[a] |
|---|---|---|
| | No other micro or macroscopic observations were noted in the study. | end of recovery. No other micro or macroscopic observations were noted in the study. |
| Immunogenicity | Data not available yet | Data not available yet |

[a]Rat and monkey 28-day toxicity studies are in reporting phase.
[b]In rat study single-dose of ALP201 was administered at 10 mg/kg intravenously to Group 5 animals, to determine the absolute bioavailability of ALP201 following SC administration.
[c]Gender-combined mean systemic exposure values are reported. AUC values for the IV and SC studies are reported as $AUC_{0\text{-}24.5}$ and $AUC_{0\text{-}168}$, respectively.
Abbreviations:
ALP = alkaline phosphatase;
AUC = area under the concentration-time curve;
$C_{max}$ = maximum observed plasma concentration;
CNS = central nervous system;
ECG = electrocardiogram;
GLP = good lab practices;
IV = intravenous;
NOAEL = no-observed adverse effect level;
Q3D = every 3 days
SC = subcutaneous.

Nonclinical Safety Strategy for ALP201 Late-Stage Clinical Development

ALP201 is an improved ERT relative to Alexion's marketed ERT product asfotase alfa (STRENSIQ®). The human TNSALP catalytic domain of ALP201 includes rationally designed changes at 3 positions to confer a higher enzymatic activity. The Fc part of ALP201 is a human immunoglobulin gamma 2/4 (IgG2/4), while the Fc portion of asfotase alfa is a human immunoglobulin IgG1. The C-terminal regions of ALP201 and asfotase alfa, which target the bone, are identical.

The available findings from ALP201 and selected asfotase alfa studies are as follows:
1. The toxicity findings from ALP201 GLP 28 days toxicology studies in rats and monkeys are very similar (Table 31)
2. The toxicity findings from ALP201 and asfotase alfa toxicology studies of similar duration (4 weeks/28 days) in monkeys and rats are very similar (Table 32 and Table 33, respectively)
3. The toxicity findings from the asfotase alfa complete nonclinical safety package are largely limited to transient local tolerability findings in rats, with no other noteworthy adverse asfotase alfa-treatment related findings.

ALP201 Chronic/6 Months General Toxicology Studies Strategy

A single species chronic toxicology study strategy is supported by the following observations:

4. No noteworthy systemic toxicity and/or local tolerability findings were observed in rat and monkey 28-day GLP toxicology studies, following 10 repeated administrations of SC ALP201 once every 3 days (Q3D), although the systemic exposures of ALP201 were significantly higher compared to asfotase alfa. The systemic exposures are summarized in Tables 31 and 32
5. The toxicity findings from ALP201 rat and monkey 28-day GLP toxicology studies were very similar. The findings from these studies are summarized in Table 28
6. If the toxicological findings from short term general toxicology studies are similar, then longer-term general toxicity studies in 1 species are usually considered sufficient.
7. Rat is the preferred species for chronic toxicity study with ALP201. Additionally, rat is the preferred species when only one species is used to conduct longer term general toxicity studies.

TABLE 28

Comparison of Findings From Asfotase Alfa and ALP201 Monkey GLP Toxicity Studies

| | Asfotase Alfa Monkey GLP Toxicity Study | Asfotase Alfa Monkey GLP Toxicity Study | ALP201 Monkey GLP Toxicity Study |
|---|---|---|---|
| Age of Animals | Approximately 1 year (Juvenile monkeys) | Approximately 1 year (Juvenile monkeys) | Approximately 2-3 years |
| Duration of Study | 4 Weeks | 6 Months (26 Weeks) | 4 Weeks |
| Recovery Period | 28 Days | 28 Days | 28 Days |
| Route of Administration | Intravenous injection | Subcutaneous injection | Subcutaneous injection |
| Frequency of Administration | Once weekly | Once daily | Once every 3 days (Q3D) |
| Total Number of Doses Administered | 4 doses (Days 1, 8, 15, and 22) | 182 doses | 10 doses |
| Doses administered | 0, 5, 15, or 45 mg/kg/dose | 0, 0.43, 2.14, or 10 mg/kg/day | 0, 1, 5, or 20 mg/kg/dose |
| NOAEL | 45 mg/kg/dose | 10 mg/kg/day | 20 mg/kg/dose |
| $AUC_{0\text{-}168h}$ at NOAEL | Day 1: 3,190 µg · hr/mL | Day 1: 50 µg · hr/mL[a] | Day 1: 27,900 µg · hr/mL |
| | Day 22: 2,670 µg · hr/mL | Week 26: 124 µg · hr/mL[a] | Day 24: 36,800 µg · hr/mL |
| $C_{max}$ at NOAEL | Day 1: 726 µg/mL | Day 1: 2.66 µg/mL | Day 1: 125 µg/mL |
| | Day 22: 691 µg/mL | Week 26: 6.68 µg/mL | Day 24: 254 µg/mL |
| Mortality | No mortality | No mortality | No mortality |

TABLE 28-continued

Comparison of Findings From Asfotase Alfa and ALP201 Monkey GLP Toxicity Studies

|  | Asfotase Alfa Monkey GLP Toxicity Study | Asfotase Alfa Monkey GLP Toxicity Study | ALP201 Monkey GLP Toxicity Study |
| --- | --- | --- | --- |
| Clinical Observations | No treatment-related clinical observations | No treatment-related clinical observations | No treatment-related clinical observations |
| Body Weight | No treatment-related findings | No treatment-related findings | No treatment-related findings |
| Food Consumption | No treatment-related findings | No treatment-related findings | No treatment-related findings |
| Ophthalmology | No treatment-related findings | No treatment-related findings | No treatment-related findings |
| Dermal Observations | No treatment-related findings | Injection site reaction at all doses include skin scabs, dry and/or red skin | No treatment-related findings at site of injections |
| ECG | No treatment-related findings based on quantitative parameters (heart rate, RR interval, PR interval, QRS duration, QT interval, and QTc interval) and qualitative review of the ECG | No treatment-related findings based on quantitative parameters (heart rate, RR interval, PR interval, QRS duration, QT interval, and QTc interval) and qualitative review of the ECG | No treatment-related findings based on quantitative parameters (heart rate, RR interval, PR interval, QRS duration, QT interval, and QTc interval) and qualitative review of the ECG |
| Blood Pressure | No treatment-related findings | No treatment-related findings | No treatment-related findings |
| Clinical Pathology | | | |
| Hematology | No treatment-related findings | No treatment-related findings | No treatment-related findings |
| Coagulation | No treatment-related findings | No treatment-related findings | No treatment-related findings |
| Clinical Chemistry | No treatment-related findings apart from dose dependent increases in ALP levels, a pharmacological effect | No treatment-related findings apart from dose dependent increases in ALP levels, a pharmacological effect | No treatment-related findings apart from dose dependent increases in ALP levels, a pharmacological effect |
| Urinalysis | No treatment-related findings | No treatment-related findings | No treatment-related findings |
| Organ Weights | No treatment-related findings | No treatment-related findings | No treatment-related findings |
| Macroscopic Findings | No treatment-related findings | No treatment-related findings | No treatment-related findings |
| Anatomic Pathology | No treatment-related findings | Injection sites had focal granulomatous inflammation and mononuclear infiltration at doses ≥0.43 mg/kg/dose that was partially to completely recovered at the end of recovery period; Slight degeneration or necrosis of muscle underneath the site of injection in one male monkey at 2.14 mg/kg/dose | Slight degeneration/necrosis and mineralization of injection sites were observed; but were concluded non-adverse. These findings were partially recovered at the end of recovery. No other micro or macroscopic observations were noted in the study. |

[a] AUC values for Study 670338 are reported as $AUC_{0-24h}$

Abbreviations:
ALP = Alkaline phosphatase;
AUC = area under the concentration-time curve;
ADA = anti-drug antibody;
$C_{max}$ = maximum observed plasma concentration;
ECG = electrocardiogram;
GLP = good lab practices;
NOAEL = no-observed adverse effect level;
Q3D = every 3 days.

TABLE 29

Comparison of Findings From Asfotase Alfa and ALP201 Rat GLP Toxicity Studies

|  | Asfotase Alfa Rat GLP Toxicity Study | Asfotase Alfa Rat GLP Toxicity Study | ALP201 Rat GLP Toxicity Study |
| --- | --- | --- | --- |
| Age of Animals | Approximately 21-24 days (Juvenile rats) | Approximately 21 days (Juvenile rats) | Approximately 7-8 weeks |
| Duration of Study | 4-Weeks | 6-Months | 4-Weeks |
| Recovery Period | 28-Days | 28-Days | 28-Days |
| Route of Administration | Intravenous injection | Intravenous injection | Subcutaneous injection |
| Frequency of Administration | Once weekly | Once daily | Once every 3 days (q3d) |
| Total Number of Doses Administered | 4 doses (Days 1, 8, 15, and 22) | 182 doses | 10 doses |
| Doses administered | 0, 3, 30, or 90 mg/kg/dose (Nominal doses) 0, 2.6, 26, or 77 mg/kg/dose (Actual measured doses) | 0, 1, 3, or 13 mg/kg/day | 0, 2, 10, or 30 mg/kg/dose |
| NOAEL | 26 mg/kg/dose | 13 mg/kg/day | 30 mg/kg/dose |
| $AUC_{0-168}$[a] at NOAEL | Day 23: NA | Week 1: 364 μg · hr/mL Week 26: 379 μg · hr/mL | Day 1: 11,600 μg · hr/mL Day 24: 4,380 μg · hr/mL |

TABLE 29-continued

Comparison of Findings From Asfotase Alfa and ALP201 Rat GLP Toxicity Studies

| | Asfotase Alfa Rat GLP Toxicity Study | Asfotase Alfa Rat GLP Toxicity Study | ALP201 Rat GLP Toxicity Study |
|---|---|---|---|
| $C_{max}$ at NOAEL | Day 23: 3.79 µg/mL | Week 1: 115 µg/mL<br>Week 26: 281 µg/mL | Day 1: 79.9 µg/mL<br>Day 24: 43.9 µg/mL |
| Mortality | 1 rat (concluded non treatment-related) | 9 rats (all 9 deaths were concluded non treatment-related) | No mortality |
| Clinical Observations | Acute/transient injection reactions (up to 60 minutes post-dose) at all doses; no injection reactions were observed during recovery period in all groups or vehicle control group during treatment period | Acute dose-dependent swelling of extremities (fore and hind paws and muzzle); these swelling subsided in <24 hours post-dose | No treatment-related clinical observations |
| Body Weight | Dose-dependent slight decreases (7.4-12.1%) in mean body weight gain in males during recovery period | No treatment-related findings | No treatment-related findings |
| Food Consumption | Dose-dependent slight decreases in food consumption in males correlating with decreases in bodyweight gains | No treatment-related findings | No treatment-related findings |
| Ophthalmology | No treatment-related findings | No treatment-related findings | No treatment-related findings |
| Dermal Observations | No treatment-related findings | Injection site reaction at all doses include skin scabs, dry and/or red skin | No treatment-related findings at site of injections |
| CNS | No treatment-related findings | No treatment-related findings | No treatment-related findings |
| Estrous Cycle | No treatment-related findings | No treatment-related findings | No treatment-related findings |
| Clinical Pathology | | | |
| Hematology | At high dose slight decreases in neutrophils, monocytes and eosinophils; slight increases in lymphocytes, platelets, and reticulocytes relative to control group | No treatment-related findings | No treatment-related findings |
| Coagulation | No treatment-related findings | No treatment-related findings | No treatment-related findings |
| Clinical Chemistry | No treatment-related findings apart from dose dependent increases in ALP levels, a desired pharmacological effect | No treatment-related findings apart from dose dependent increases in ALP levels, a desired pharmacological effect | No treatment-related findings apart from dose dependent increases in ALP levels, a desired pharmacological effect |
| Urinalysis | No treatment-related findings | No treatment-related findings | No treatment-related findings |
| Organ Weights | No treatment-related findings | No treatment-related findings | No treatment-related findings |
| Macroscopic Findings | No treatment-related findings | No treatment-related findings | No treatment-related findings |
| Anatomic Pathology | No treatment-related findings | No treatment-related findings | Sporadic injection site findings with associated reactive changes in the draining lymph nodes; these findings were not dose dependent and were concluded to be non-adverse; these findings were partially reversed at the end of recovery. No other micro or macroscopic observations were noted in the study. |
| Immunogenicity | The screening ADA assay demonstrated ADA in all dose groups including vehicle (Day 1 67% and Day 28 100%) and treatment groups (Day 1 56 to 89% and Day 28 100%); no confirmatory ADA assay was conducted due to low sample volume availability. | No noteworthy ADA response observed | Data not available yet |

[a]Gender-combined mean systemic exposure values are reported. AUC values are reported as $AUC_{0-168}$ Abbreviations:
ALP = Alkaline phosphatase;
AUC = area under the concentration-time curve;
ADA = anti-drug antibody;
$C_{max}$ = maximum observed plasma concentration;
CNS = central nervous system;
GLP = good lab practices;
IV = intravenous;
MTD = maximum tolerated dose;
NOAEL = no-observed adverse effect level;
Q3D = every 3 days;
SC = subcutaneous.

Model-Based Analyses and Predicted Human Dose Regimens
ALP201 Modeling
Data Used in Current Models To perform dose extrapolation from mouse (disease model species) to human, sufficient PK analysis is required to simulate human exposures from allometrically-scaled doses. Limited mouse PK data was available; a single dose wildtype mouse study (HPP-PK-01) and single $C_{trough}$ measurements (D36/D37) from 2 multiple dose Akp2GW −/− mouse efficacy studies (HPP-PoC-01 and HPP-MED-01). To create a robust PK characterization of ALP201, the mouse data was enriched with PK data from dose range-finding studies in rats and cynomolgus monkeys. Table 30 shows the data (47 animals and 387 PK concentrations), to date, analyzed using a population pharmacokinetic (Pop-PK) modeling approach. For the dose-response modeling, efficacy (bone mineralization) data from 2 Akp2GW −/− mouse efficacy studies (HPP-PoC-01 and HPP-MED-01) were used.

TABLE 30

ALP201 Single Dose PK Data Used to Develop the Pop-PK Model

ALP201 Single Dose, mg/kg; N (measurements)

| Species | Route | 1 | 2 | 3 | 4 | 6 | 9 | 20 | 27 | Total |
|---|---|---|---|---|---|---|---|---|---|---|
| Mouse | IV | . | . | . | 4 (30) | . | . | . | . | . |
|  | SC | . | . | . | 4 (37) | . | . | . | . | . |
| Rat | IV | 4 (33) | . | 4 (33) | . | . | 4 (36) | . | 4 (35) | . |
|  | SC | . | 4 (24) | . | . | . | . | . | 4 (35) | . |
| Monkey | IV | . | 3 (27) | . | . | 3 (26) | . | 3 (24) | . | . |
|  | SC | . | 3 (24) | . | . | . | . | 3 (24) | . | . |
| Total | | . | . | . | . | . | . | . | . | 47 (387) |

Abbreviations:
IV = intravenous;
N = number of animals;
PK = pharmacokinetic(s);
Pop-PK = population-pharmacokinetics;
SC = subcutaneous.

Current Pop-PK Model

The current Pop-PK model was developed using the NONMEM software program, version 7.2 (ICON solutions) to simultaneously analyze PK data from 3 animal species accounting for species differences in PK disposition using bodyweight based allometric principles, where animal body weight was centered to 70 kg and allometric exponents were fixed to 0.75 for clearance parameters and 1.0 for volume of distribution parameters. The IV and SC data were also fit simultaneously to estimate extravascular parameters, e.g., absolute bioavailability, following SC injection. The current model is a two-compartment model with linear elimination and model parameter estimates are in Table 31.

TABLE 31

Parameter Estimates for the Interim Pop-PK Model

| Parameter, Units | Typical Value | RSE (%) | BSV (%) | RSE (%) | Shrinkage (%) |
|---|---|---|---|---|---|
| Clearance, CL, L/h/70 kg | 0.025 | 5 | 27 | 24 | 10 |
| Central Volume, V2, L/70 kg | 3.48 | 5 | . | . | . |
| Periph Volume, V3, L/70 kg | 2.71 | 13 | . | . | . |
| Periph CL, Q, L/h/70 kg | 0.027 | 36 | . | . | . |
| Absorption Rate, Ka, 1/h | 0.031 | 25 | 86 | 41 | 40 |
| Bioavailability, F, % | 74.6 | 11 | 76 | 76 | 59 |
| Proportional residual error; RAT, % | 24.6 | 38 | . | . | 7 |
| Additive residual error; RAT, ug/mL | 0.707 | 29 | . | . | 7 |
| Proportional residual error; CYNO, % | 30.4 | 36 | . | . | 7 |
| Proportional residual error; MOUSE, % | 47 | 31 | . | . | 5 |

Abbreviations:
BSV = between subject variability;
RSE = relative standard error (parameter precision from $COV step)

The typical value or mean parameter estimates for the PK parameters were sufficiently estimated. The variability (BSV) for CL was acceptable and well estimated; however, the variability for Ka and F was large (86% and 76%, respectively) and not well estimated. Shrinkage is an assessment of how the data informed the estimation of PK parameters with a value of <30% being good. Given the high shrinkage values for Ka and F (40% and 59%, respectively), additional data from the 4-week GLP toxicology studies should improve the estimation of the Ka and F parameters. Overall, the current Pop-PK model should provide reasonable dose simulations given the good mean parameter estimates; although, the variability region may be overly wide.

Current Dose-Response Model

Figure 16:
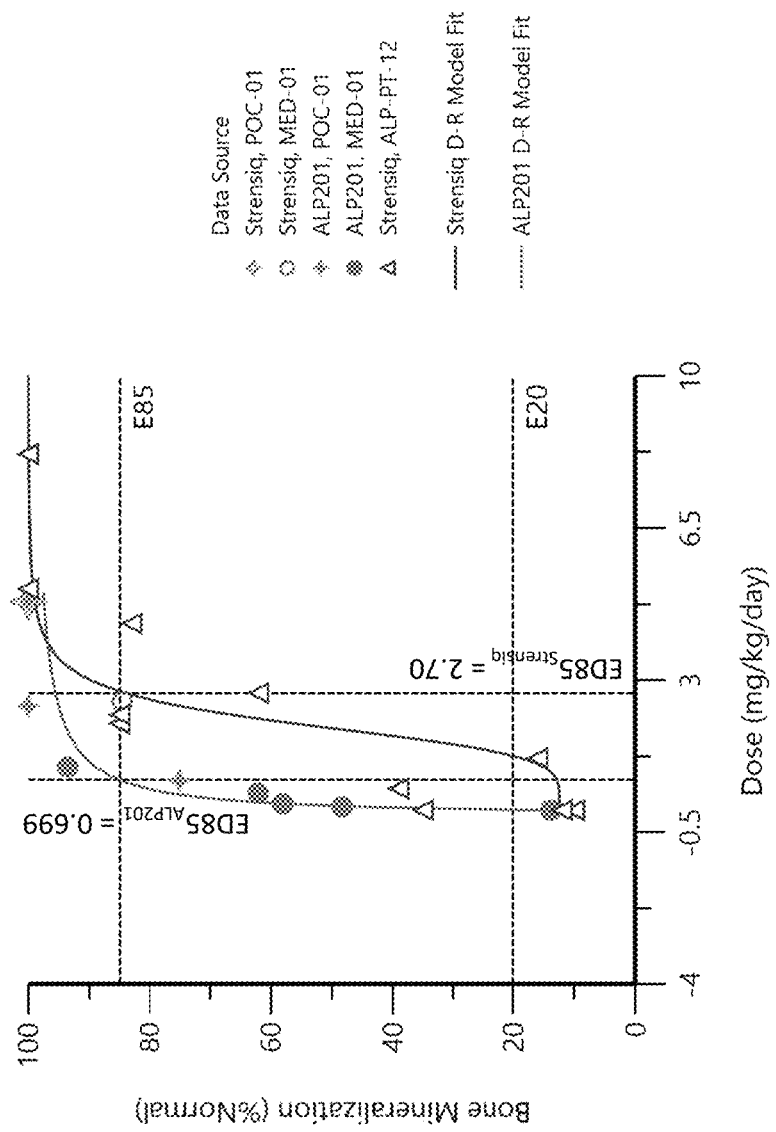
FIG. 16 is a graph showing a comparison of ALP201 and asfotase alfa (STRENSIQ®) dose-response modeling. Abbreviations: ALP=alkaline phosphatase; D-R=dose response; MED=minimum efficacious dose; POC=proof of concept.

The developed dose-response model was selected by testing models from the $E_{max}$ family. Most dose-response relationships can be described by one of the $E_{max}$ model parameterizations. The current best dose-response characterization is using an $E_{max}+E_0$ (baseline) model. The efficacy endpoint, bone mineralization, was a radiographic assessment, and was selected as it shared the same clinical definition of efficacy as that used for asfotase alfa nonclinical dose-response assessment. Bone mineralization after treatment with asfotase alfa or ALP201 from 2 efficacy studies (HPP-PoC-01 and HPP-MED-01) was plotted versus dose (FIG. 16). Asfotase alfa data from previous efficacy study ALP-PT-12 was included for comparison. The y-axis was expressed as % Normal, which was defined as the percentage of mice in a dose group with bone mineralization scores of 4. The x-axis was expressed as dose normalized to mg/kg/day. The dose producing normal mineralization in 85% of the treated population (ED85) was chosen as the target effective dose.

Dose Translation from Mouse to Human and Proposed Human Starting Doses

Allometric scaling was applied to mouse target effective dose (ED85) to determine a human dose. The equation to predict from mouse ED85 to human equivalent dose (HED, mg/kg/day) was ED85×(0.025 kg mouse/70 kg human)$^{0.25}$. The HED was translated into a weekly flat dose of 45 mg/week and used as the starting dose for the MAD arm of the FIH study. The maximum recommended starting dose (MRSD) for the SAD arm was selected after considering results from the NOAEL and MABEL methods. It was decided that the studied dose that produced the minimum on-target pharmacological response would be selected and translated to a flat human dose (5 mg).

Other Embodiments

The foregoing detailed description and examples have been given for clarity of understanding only. No unnecessary limitations are to be understood therefrom. The disclosure is not limited to the exact details shown and described, for variations apparent to one skilled in the art will be included within the scope defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The disclosure is not limited to the exact details shown and described, for variations apparent to one skilled in the art will be included within the embodiments defined by the claims.

The invention claimed is:

1. A pharmaceutical composition comprising a dimer comprising a first polypeptide and a second polypeptide, each polypeptide comprising the amino acid sequence of SEQ ID NO: 5, wherein the dimer is linked by a first disulfide bond between C494 of the first polypeptide and C494 of the second polypeptide and a second disulfide bond between C497 of the first polypeptide and C497 of the second polypeptide, wherein the pharmaceutical composition comprises a pharmaceutically acceptable carrier comprising one or more of phosphate, proline, and sucrose.

2. The pharmaceutical composition of claim 1, wherein the composition comprises from about 1 mM to about 100 mM phosphate.

3. The pharmaceutical composition of claim 2, wherein the composition comprises from about 5 mM to about 20 mM phosphate.

4. The pharmaceutical composition of claim 3, wherein the composition comprises about 10 mM phosphate.

5. The pharmaceutical composition of claim 1, wherein the phosphate is sodium phosphate.

6. The pharmaceutical composition of claim 1, wherein the composition comprises from about 1 mM to about 500 mM proline.

7. The pharmaceutical composition of claim 6, wherein the composition comprises from about 50 mM to about 200 mM proline.

8. The pharmaceutical composition of claim 7, wherein the composition comprises about 140 mM proline.

9. The pharmaceutical composition of claim 1, wherein the composition comprises from about 1 mM to about 500 mM sucrose.

10. The pharmaceutical composition of claim 9, wherein the composition comprises from about 50 mM to about 200 mM sucrose.

11. The pharmaceutical composition of claim 10, wherein the composition comprises about 140 mM sucrose.

12. The pharmaceutical composition of claim 3, wherein the composition comprises about 10 mM phosphate, about 140 mM proline, and about 140 mM sucrose.

13. The pharmaceutical composition of claim 1, wherein the composition comprises from about 0.01% to about 0.5% polyoxyethylene (20) sorbitan monooleate.

14. The pharmaceutical composition of claim 13, wherein the composition comprises from about 0.01% to about 0.1% polyoxyethylene (20) sorbitan monooleate.

15. The pharmaceutical composition of claim 14, wherein the composition comprises about 0.05% polyoxyethylene (20) sorbitan monooleate.

16. The pharmaceutical composition of claim 15, wherein the composition comprises about 140 mM proline, about 140 mM sucrose, and about 0.05% polyoxyethylene (20) sorbitan monooleate.

17. The pharmaceutical composition of claim 1, wherein the polypeptide comprises a total sialic acid content (TSAC) from about 1.0 mol/mol to about 6.0 mol/mol.

18. The pharmaceutical composition of claim 17, wherein the TSAC is from about 3.0 mol/mol to about 6.0 mol/mol.

19. The pharmaceutical composition of claim 18, wherein the TSAC is about 3.2 mol/mol, 5.0 mol/mol or about 5.9 mol/mol.

20. The pharmaceutical composition of claim 1, wherein the composition comprises a pH of about 7.3.

21. The pharmaceutical composition of claim 1, wherein the dimer is formulated at a concentration of about 0.1 mg/mL to about 200 mg/mL.

22. The pharmaceutical composition of claim 21, wherein the dimer is formulated at a concentration of about 100 mg/mL in a volume of about 1 mL.

23. The pharmaceutical composition of claim 1, wherein the composition is formulated in a volume of about 0.1 mL to about 50 mL.

24. The pharmaceutical composition of claim 1, wherein the first polypeptide comprises disulfide bonds between C122 and C184, C472 and C480, C528 and C588, and C634 and C692, and the second polypeptide comprises disulfide bonds between C122 and C184, C472 and C480, C528 and C588, and C634 and C692.

25. The pharmaceutical composition of claim 1, wherein C102 of the first polypeptide and the second polypeptide is a free cysteine.

26. The pharmaceutical composition of claim 1, wherein the first polypeptide and the second polypeptide is glycosylated at N123, N254, N413, and N564.

27. The pharmaceutical composition of claim 1, wherein each of the first polypeptide and the second polypeptide coordinates two zinc ions, one magnesium ion, and one calcium ion.

28. A vial comprising the pharmaceutical composition of claim 1.

29. A method of treating a bone mineralization disorder in a subject in need thereof comprising administering a dose of the pharmaceutical composition of claim 1 to the subject.

* * * * *